US008957042B2

(12) United States Patent
Safe et al.

(10) Patent No.: US 8,957,042 B2
(45) Date of Patent: Feb. 17, 2015

(54) CANCER TREATMENT TARGETING NON-CODING RNA OVEREXPRESSION

(71) Applicant: The Texas A&M University System, College Station, TX (US)

(72) Inventors: Stephen Safe, College Station, TX (US); KyoungHyun Kim, Houston, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 13/789,546

(22) Filed: Mar. 7, 2013

(65) Prior Publication Data

US 2013/0267575 A1 Oct. 10, 2013

Related U.S. Application Data

(60) Provisional application No. 61/607,984, filed on Mar. 7, 2012.

(51) Int. Cl.

| | |
|---|---|
| ***A61K 48/00*** | (2006.01) |
| ***C07H 21/02*** | (2006.01) |
| ***C07H 21/04*** | (2006.01) |
| ***C12N 15/85*** | (2006.01) |

(52) U.S. Cl.

USPC ............ 514/44; 536/23.1; 536/24.5; 435/325

(58) Field of Classification Search

None

See application file for complete search history.

(56) References Cited

U.S. PATENT DOCUMENTS

| | | | | |
|---|---|---|---|---|
| 2006/0293267 | A1 | 12/2006 | Zamore | |
| 2007/0259829 | A1 | 11/2007 | Abdelrahim | |
| 2008/0261911 | A1 | 10/2008 | Safe | |
| 2009/0099123 | A1 | 4/2009 | Safe | |
| 2009/0203661 | A1 | 8/2009 | Safe | |
| 2010/0099760 | A1 | 4/2010 | Safe | |
| 2012/0004278 | A1 | 1/2012 | Chang | |
| 2013/0267443 | A1 * | 10/2013 | Chinnaiyan et al. ............ | 506/39 |

OTHER PUBLICATIONS

Abdelrahim, M., et al., "Regulation of Vascular Endothelial Growth Factor Receptor-1 Expression by Specificity Proteins 1, 3, and 4 in Pancreatic Cancer Cells," Cancer Research 67(7):3286-3294, Apr. 2007.

Abdelrahim, M., et al., "RNAi and Cancer: Implications and Applications," Journal of RNAi and Gene Silencing 2(1):136-145, Feb. 2006.

Abdelrahim, M., et al., "Tolfenamic Acid and Pancreatic Cancer Growth, Angiogenesis, and Sp Protein Degradation," Journal of the National Cancer Institute 98(12):855-868, Jun. 2006.

Badea, L., et al., "Combined Gene Expression Analysis of Whole-Tissue and Microdissected Pancreatic Ductal Adenocarcinoma Identifies Genes Specifically Overexpressed in Tumor Epithelia," Hepato-Gastroenterology 55(88):2015-2026, Nov.-Dec. 2008.

Chadalapaka, G., et al., "Curcumin Decreases Specificity Protein (Sp) Expression in Bladder Cancer Cells," Cancer Research 68(13):5345-5354, Jul. 2008.

Chadalapaka, G., et al., "Drugs That Target Specificity Proteins Downregulate Epidermal Growth Factor Receptor in Bladder Cancer Cells," Molecular Cancer Research 8(5):739-750, May 2010.

Chintharlapalli, S., et al., "Betulinic Acid Inhibits Prostate Cancer Growth Through Inhibition of Specificity Protein Transcription Factors," Cancer Research 67(6):2816-2823, Mar. 2007.

Chintharlapalli, S., et al., "Inhibition of Pituitary Tumor-Transforming Gene-1 in Thyroid Cancer Cells by Drugs That Decrease Specificity Proteins," Molecular Carcinogenesis 50(9):655-667, Sep. 2011.

Chintharlapalli, S., et al., "Oncogenic microRNA-27a Is a Target for Anticancer Agent Methyl 2-Cyano-3,11-dioxo-18β-olean-1,12-dien-30-oate in Colon Cancer Cells," International Journal of Cancer 125(8):1965-1974, Oct. 2009.

Chisholm, K.M., et al., "Detection of Long Non-Coding RNA in Archival Tissue: Correlation With Polycomb Protein Expression in Primary and Metastatic Breast Carcinoma," PLoS One 7(10):e47998, Oct. 2012, 8 pages.

Collisson, E.A., et al., "Subtypes of Pancreatic Ductal Adenocarcinoma and Their Differing Responses to Therapy," Nature Medicine 17(4):500-504, Apr. 2011.

Giovannetti, E., et al., "MicroRNA-21 in Pancreatic Cancer: Correlation With Clinical Outcome and Pharmacologic Aspects Underlying Its Role in the Modulation of Gemcitabine Activity," Cancer Research 70(11):4528-4538, Jun. 2010.

Gupta, R.A., et al., "Long Noncoding RNA HOTAIR Reprograms Chromatin State to Promote Cancer Metastasis," Nature 464(7291):1071-1076, Apr. 2010.

Hingorani, S.R., et al., "Trp53R172H and KrasG12D Cooperate to Promote Chromosomal Instability and Widely Metastatic Pancreatic Ductal Adenocarcinoma in Mice," Cancer Cell 7(5):469-483, May 2005.

Huarte, M., and J.L. Rinn, "Large Non-Coding RNAs: Missing Links in Cancer?" Human Molecular Genetics 19(R2):R152-R161, Oct. 2010.

International Search Report mailed Jun. 25, 2013, issued in corresponding International Application No. PCT/US2013/029709, filed Mar. 7, 2013, 4 pages.

(Continued)

*Primary Examiner* — Amy Bowman

(74) *Attorney, Agent, or Firm* — Christensen O'Connor Johnson Kindness PLLC

(57) ABSTRACT

Provided herein are methods directed to modulating the pro-oncogenic effects of noncoding RNAs (ncRNAs) through their interactions with specificity protein transcription factors (SpTFs). In one aspect, the disclosure provides a method of inhibiting growth of a cell, such as a transformed or cancer cell, characterized by overexpression of at least one specificity protein (Sp)-regulated ncRNA and expression of at least one Sp transcription factor (SpTF), the method comprising contacting the cell with an effective amount of an SpTF agent. In some embodiments, the ncRNA is a long noncoding RNA (lncRNA). In some embodiments, the ncRNA is a microRNA (miR). Also provided are methods of treating a cell proliferative disease, predicting the response of a subject to SpTF agent-based treatment, and monitoring the efficacy of a SpTF agent-based treatment in a subject.

14 Claims, 25 Drawing Sheets

(56) References Cited

OTHER PUBLICATIONS

Ji, P., et al., "Malat-1, a Novel Noncoding RNA, and Thymosin β4 Predict Metastasis and Survival in Early-Stage Non-Small Cell Lung Cancer," Oncogene 22(39):8031-8041, Sep. 2003.
Jutooru, I., et al., "Arsenic Trioxide Downregulates Specificity Protein (Sp) Transcription Factors and Inhibits Bladder Cancer Cell and Tumor Growth," Experimental Cell Research 316(13):2174-2188, Aug. 2010.
Jutooru, I., et al., "Inhibition of $Nf_k$ B and Pancreatic Cancer Cell and Tumor Growth by Curcumin Is Dependent on Specificity Protein Down-Regulation," Journal of Biological Chemistry 285(33):25332-25344, Aug. 2010.
Jutooru, I, et al., "Methyl 2-Cyano-3, 12-dioxooleana-1,9-dien-28-oate Decreases Specificity Protein Transcription Factors and Inhibits Pancreatic Tumor Growth: Role of MicroRNA-27a," Molecular Pharmacology 78(2):226-236, Aug. 2010.
Khalil, a.M., et al., "Many Human Large Intergenic Noncoding RNAs Associate With Chromatin-Modifying Complexes and Affect Gene Expression," Proceedings of the National Academy of Sciences of the United States of America (PNAS) 106(28):11667-11672, Jul. 2009.
Konduri, S., et al., "Tolfenamic Acid Enhances Pancreatic Cancer Cell and Tumor Response to Radiation Therapy by Inhibiting Survivin Protein Expression," Molecular Cancer Therapeutics 8(3):533-542, Mar. 2009.
Li, L. et al "Role of Human Noncoding RNAs in the Control of Tumorigenesis," Proceedings of the National Academy of Sciences of the United States of America (PNAS) 106(31):12956-12961, Aug. 2009.
Mendell, J.T., "miRiad Roles for the miR-17-92 Cluster in Development and Disease," Cell 133(2):217-222, Apr. 2008.
Mertens-Talcott, S.U., et al., "The Oncogenic microRNA-27a Targets Genes That Regulate Specificity Protein Transcription Factors and the $G_2$ -M Checkpoint in MDA-MB-231 Breast Cancer Cells," Cancer Research 67(22):1101-11011, Nov. 2007.
Morris, K.R., "Structural Aspect of Hydrates and Solvates," in H.G. Brittain (ed.), "Polymorphism in Pharmaceutical Solids," vol. 95 of "Drugs and the Pharmaceutical Sciences," Marcel Dekker, New York, 1999, Chap. 4, pp. 125-481.
Nielsen, B.S., et al., "High Levels of microRNA-21 in the Stroma of Colorectal Cancers Predict Short Disease-Free Survival in Stage II Colon Cancer Patients," Clinical & Experimental Metastasis 28(1):27-38, Jan. 2011.
Papineni, S., et al., "Tolfenamic Acid Inhibits Esophageal Cancer Through Repression of Specificity Proteins and c-Met," Carcinogenesis 30(7):1193-1201, Jul. 2009.
Perez, D.S., et al., "Long, Abundantly Expressed Non-Coding Transcripts Are Altered in Cancer," Human Molecular Genetics 17(5):642-655, Mar. 2008.
Rinn, J.L., et al., "Functional Demarcation of Active and Silent Chromatin Domains in Human HOX Loci by Noncoding RNAs," Cell 129(7):1311-1323, Jun. 2007.
Stratford, J.K., et al., "A Six-Gene Signature Predicts Survival of Patients With Localized Pancreatic Ductal Adenocarcinoma," PLoS Medicine 7(7):e1000307, Jul. 2010, 9 pages.
Tsai, M.-C., et al., "Long Intergenic Noncoding RNAs: New Links in Cancer Progression," Cancer Research 71(1):3-7, Jan. 2011.
Wang, B., et al., "TGFβMediated Upregulation of Hepatic miR-181b Promotes Hepatocarcinogenesis by Targeting TIMP3," Oncogene 29(12)1787-1797, Mar. 2010.
Wang, K.C., et al., "A Long Noncoding RNA Maintains Active Chromatin to Coordinate Homeotic Gene Expression," Nature 472(7341):120-124, Apr. 2011.
Yang, F., et al., "Long Noncoding RNA High Expression in Hepatocellular Carcinoma Facilitates Tumor Growth Through Enhancer of Zeste Homolog 2 in Humans," Hepatology 54(5):1679-1689, Nov. 2011.
Zhang, X., et al., "A Myelopoiesis-Associated Regulatory Intergenic Noncoding RNA Transcript Within the Human HOXA Cluster," Blood 113(11)2526-2534, Mar. 2009.
Abdelrahim, M., et al., "RNAi and Cancer: Implications and Applications," Journal of RNAi and Gene Silencing 2(1):136-145, Feb. 2006, 10 pages.
International Search Report and Written Opinion mailed Jun. 25, 2013, issued in corresponding International Application No. PCT/US2013/029709, filed Mar. 7, 2013, 10 pages.
Mertens-Talcott, S.U., et al., "The Oncogenic microRNA-27a Targets Genes That Regulate Specificity Protein Transcription Factors and the $G_2$ -M Checkpoint in MDA-MB-231 Breast Cancer Cells," Cancer Research 67(22):1101-11011, Nov. 2007, 11 pages.

* cited by examiner

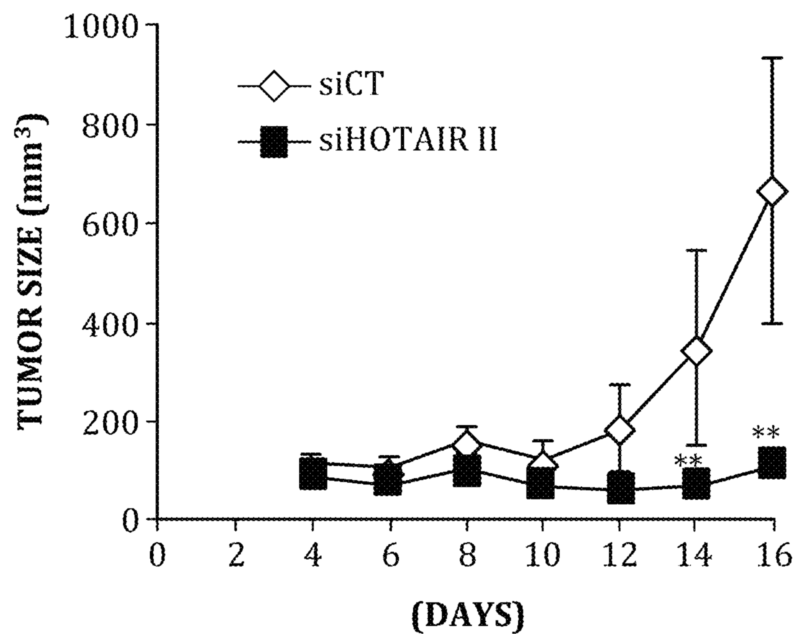
FIG.4A.
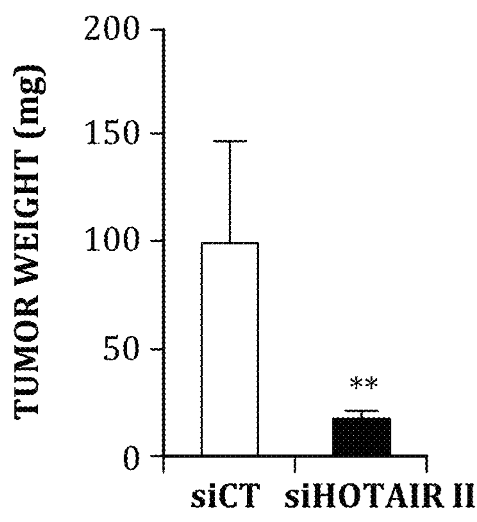
FIG.4B.
1.5
1
0.5
0
RELATIVE HOTAIR LEVEL
**
siCT (N=5)
siHOTAIR II (N=5)
FIG.4C.

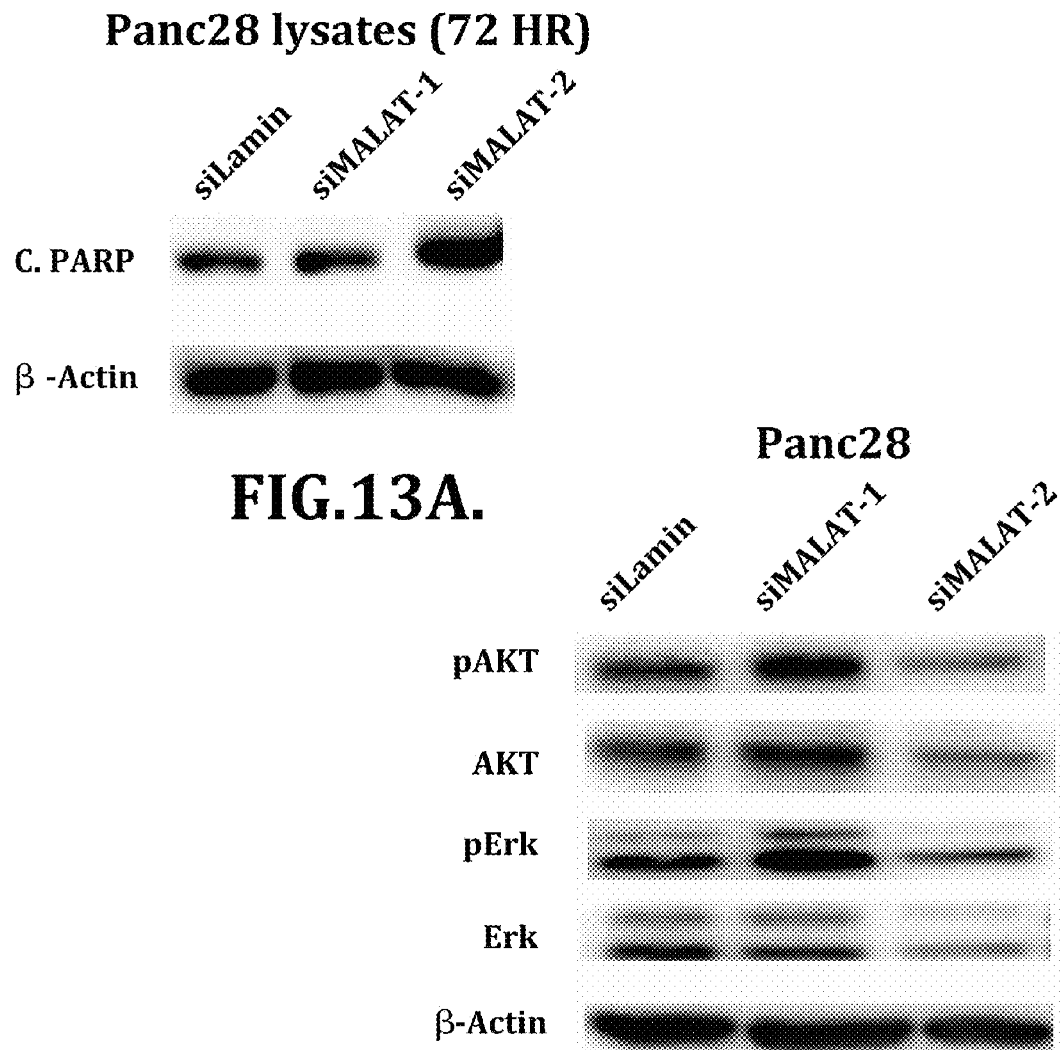
FIG.13A.
FIG.13B.
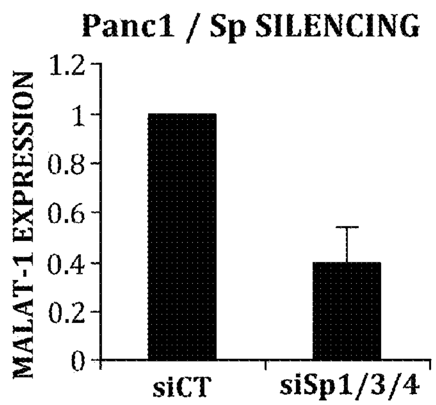
FIG.14.

CANCER TREATMENT TARGETING NON-CODING RNA OVEREXPRESSION

CROSS REFERENCE TO RELATED APPLICATION

This application claims the benefit of U.S. Provisional Application No. 61/607,984, filed Mar. 7, 2012, which is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 40872_SEQ_Final_2013-03-07.txt. The text file is 8 KB; was created on Mar. 7, 2013; and is being submitted via EFS-Web with the filing of the specification.

BACKGROUND

The progression of a normal cell cycle and the transition to subsequent development of transformed cancer cells that exhibit uncontrolled growth, survival and metastasis/angiogenesis involves multiple genetic and epigenetic changes. For most cancers, several critical genes and pathways are responsible for the noted "characteristics" of individual tumors and cancer cells, and development of mechanism-based anticancer agents that target only one gene or pathway have had limited clinical success. In contrast, drug combinations directed to multiple targets in the various pro-oncogenic pathways have been more efficacious.

During the past decade, the discovery of non-coding RNAs (ncRNAs) and the characterization of their functions in both normal and cancer tissues has added to the complexity of cell biology and cell signaling, providing another key element that regulates genes and is associated with, if not influences, cancer cell phenotype. For example, among the different classes of ncRNAs, microRNAs (miRs) have been the most extensively investigated. Functionally, miRs are small ncRNAs (21-23 bp) that exhibit sequence-specific interactions with 3'-UTR sequences in target mRNAs and these interactions generally result in gene repression due to decreased translation and/or mRNA stability. It is estimated that >1000 miRs regulate up to 30% of all protein encoding genes. Several miRs exhibit overexpression that is associated with some different tumors. Functional pro-oncogenic activity of some miRs has been associated with their inhibition of multiple genes with tumor suppressor-like activity.

Despite the advances in the art, there remains a recognized need for improved cancer therapies, including methods of identifying optimal treatments, and methods of monitoring the efficacy of such treatments. Specifically, there is a need to identify additional cancer targets, and drugs that can influence them, to provide additional mechanisms to influence a variety targets in one or more pathways. The invention set forth in this disclosure addresses this need and provides further advantages related thereto.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, this disclosure provides a method of inhibiting growth of a cell characterized by overexpression of at least one specificity protein (Sp)-regulated non-coding RNA (ncRNA) and expression of at least one Sp transcription factor (SpTF). The method comprises contacting the cell with an effective amount of an SpTF agent.

In some embodiments, the cell is a transformed cell. In some embodiments, the transformed cell is a cancer cell. In some embodiments, the cancer cell is derived from a solid tumor or non-solid tumor. In some embodiments, the cancer cell is selected from the group consisting of a breast cancer cell, a pancreatic cancer cell, a liver cancer cell, a lung cancer cell, a prostate cancer cell, and a follicular lymphoma cancer cell.

In some embodiments, the overexpression of the at least one Sp-regulated ncRNA in the cancer cell can be determined by comparing the expression level in the cancer cell to a reference standard. In some embodiments, the expression level in the cancer cell to a reference standard comprises comparing the expression level of the at least one Sp-regulated ncRNA to the expression level of the at least one Sp-regulated ncRNA in a noncancerous cell derived from the same tissue.

In some embodiments, the at least one Sp-regulated ncRNA is a long non-coding RNA (lncRNA). In some embodiments, the lncRNA is selected from the group consisting of HOTAIR, HOTAIRM, HOTTIP, MALAT-1, linc-HEIH, HULC, and AY12907. In other embodiments, the at least one Sp-regulated ncRNA is a microRNAs (miR).

In some embodiments, the at least one SpTF is Sp1, Sp3, Sp4 or other Sp/KLF transcription factor. In some embodiments, the SpTF agent comprises: a phytochemical or derivative that induces reactive oxygen species (ROS) or phosphatase activity; a naturally-occurring or synthetic triterpenoid; a non-steroidal anti-inflammatory drug (NSAID); an antisense microRNA oligonucleotide; an agent that causes overexpression of ZBTB10, ZBTB4, or related transcriptional repressor, or that induces proteasome/caspase-dependent degradation of Sp transcription factors; a thiazolidinedione; a nitro-aspirin; an isothiocyanate; aspirin; arsenic trioxide; metformin; silibinin; or a cannabinoid. In some embodiments, the Sp transcription factor agent comprises an NSAID. In further embodiments, the NSAID is a diphenyl/diphenylamine carboxylic acid. In some embodiments, the Sp transcription factor agent comprises an phytochemical. In further embodiments, the phytochemical is betulinic acid or a derivative or analog thereof. In other embodiments the phytochemical is curcumin or a derivative thereof. In some embodiments, the Sp transcription factor agent comprises a naturally-occurring triterpenoid. In further embodiments, the naturally-occurring triterpenoid is celastrol. In other embodiments, the Sp transcription factor agent comprises a synthetic triterpenoid. In some embodiments, the synthetic triterpenoid is a glycyrrhetinic acid derivative. In some embodiments, the glycyrrhetinic acid derivative is methyl 2-cyano-3,12-dioxooleana-1,9-dien-28-oate or methyl 2-cyano-3,11-dioxo-18β-olean-1,12-dien-30-oate.

In some embodiments, the method further comprises contacting the cell with one or more small interfering RNA (siRNA) molecules that hybridize with the mRNA encoding an SpTF under physiological or cell-culture conditions. In some embodiments, the cell is in vivo in a subject. In other embodiments, the cell is in vitro. In some embodiments, the cell is derived from or comprised in a sample obtained from a subject having a cell proliferative disease or suspected of having a cell proliferative disease, such as a cancer.

In another aspect, the disclosure provides a method of reducing the expression of at least one specificity protein (Sp)-regulated non-coding RNA (ncRNA) in a cell that also expresses at least one Sp transcription factor (SpTF), the method comprising contacting the cell with an effective amount of an SpTF agent.

In another aspect, the disclosure provides a method of treating a cell proliferative disease, the method comprising administering to a subject in need a therapeutically effective amount of an specificity protein transcription factor (SpTF) agent, wherein the subject has at least one transformed cell characterized by the overexpression of at least one specificity protein (Sp)-regulated non-coding RNA (ncRNA) and the expression of at least one SpTF. In some embodiments, the SpTF agent is comprised in a pharmaceutically acceptable composition. In some embodiments, the subject is a mammal, such as selected from the group consisting of: human, monkey, horse, cow, sheep, goat, dog cat, mouse, rat, and guinea pig.

In another aspect, the disclosure provides a method of predicting the response of a subject with a cell proliferative disease to a specificity protein transcription factor (SpTF) agent-based treatment. The method comprises (i) determining the expression level of at least one specificity protein (Sp)-regulated non-coding RNA (ncRNA) in a cell sample obtained from the subject, (ii) determining the expression status of at least one specificity protein transcription factor (SpTF) in the same or similar cell sample obtained from the subject, and (iii) predicting a positive response of the subject with a cell proliferative disease to treatment with an SpTF agent when the at least one Sp-regulated ncRNA is overexpressed in the cell sample and the SpTF is expressed in the same or similar cell sample. In some embodiments, the overexpression of the at least one Sp-regulated ncRNA is determined by comparing the expression of the Sp-regulated ncRNA in the cell sample to a reference standard. In some embodiments, comparing the expression of the Sp-regulated ncRNA in the cell sample to a reference standard comprises comparing the expression level of the at least one Sp-regulated ncRNA to the expression level of the at least one Sp-regulated ncRNA in a noncancerous cell derived from the same tissue. In some embodiments, the method further comprises administering an SpTF agent to the subject that is predicted to have a positive response to treatment.

In another aspect, the disclosure provides a method of monitoring the efficacy of a specificity protein transcription factor (SpTF) agent-based treatment in a subject with a cell proliferative disease. The method comprises: (i) determining the expression level of at least one specificity protein (Sp)-regulated non-coding RNA (ncRNA) in a first cell sample obtained from the subject, (ii) administering at least one SpTF agent to the subject, and determining the expression level of the at least one Sp-regulated ncRNA in a second cell sample obtained from the subject. In this method, the second cell sample is obtained from the same or similar cell source within the subject, and the second cell sample is obtained from the subject at a time after the first cell sample is obtained and after the at least one SpTF agent is administered to the subject. The treatment is determined to be effective when the expression level of the Sp-regulated ncRNA is lower in the second sample than in the first sample.

In another aspect, the disclosure provides a method of evaluating a candidate specificity protein transcription factor (SpTF) agent for use in treatment of a cell proliferative disease. The method comprises: contacting a candidate SpTF agent to a cell characterized by (a) overexpression of at least one specificity protein (Sp)-regulated non-coding RNA (ncRNA), and (b) expression of an SpTF. The method further comprises determining the expression level of the at least one Sp-regulated ncRNA subsequent to the contacting step, and comparing the expression level of the at least Sp-regulated ncRNA to a reference standard, wherein a reduced expression level of the at least Sp-regulated ncRNA in comparison to the reference standard is indicative of the efficacy of the candidate SpTF agent for treatment of a cell proliferative disease. In some embodiments, the cell is obtained from a plurality of similar cells, and wherein the reference standard comprises one or more cells obtained from the same plurality of similar cells, such as a plurality of cells obtained from a tumor mass, that are not contacted with the SpTF agent. In some embodiments, the cell is a cancer cell and the reference standard comprises a noncancerous cell derived from the same tissue as the cancer cell.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 1A illustrates HOTAIR expression in normal pancreas and pancreatic tumors from patients as determined from a data mining analysis from patient array data. FIG. 1B illustrates the relative expression of HOTAIR in pancreatic cancer patients with tumor localized in the pancreas (NO) or those with tumors already spread to regional lymph nodes (NO). FIG. 1C illustrates the relative expression of HOTAIR in pancreatic cancer patients in patients with tumor detected only in the pancreas (T2) and tumors extending beyond the pancreas (T3). FIG. 1D illustrates HOTAIR expression in pancreatic cancer cells from different cell lines as determined by real time RT polymerase chain reaction (PCR). N indicates the number of patients.

FIGS. 4A-4C illustrate the effects of HOTAIR on in vivo tumor development in a murine xenograft model. siHOTAIR or siCT was transfected into L3.6pL cells, which were then used in a xenograft model in athymic nude mice (six per group), and tumor volumes were determined over 16 days (FIG. 4A). Tumor weights and relative HOTAIR RNA levels were determined at the end of the study (FIG. 4B). Quantitative results are means±s.e. for at least three replicate determinations for each data point, and significant (**inhibition, $p>0.05$) response by siHOTAIR (compared with siCT) is indicated.

FIG. 6A illustrates that the siSp1, siSp3, and siSp4 oligonucleotides knockdown their respective target transcripts. FIG. 6B illustrates that each indicated siRNA also significantly reduces the expression of lncRNAs HOTAIR, HOTTIP, and HOTARM in Panc1 cells.

FIG. 8A illustrates the induction of ZBTB10 expression by CDODA-Me and $CF_3$CDODA with or without DDT. FIG. 8B illustrates the reduction of miR27a by CDODA-Me and $CF_3$CDODA, which effect is negated by DDT. FIG. 8C illustrates the reduction of SpTFs by CDODA-Me and $CF_3$CDODA, which effect is negated by DDT. FIG. 8D illustrates the reduction of HOTAIR RNA abundance by CDODA-Me and $CF_3$CDODA, which effect is negated by DDT.

FIG. 9A illustrates the reduction of HOTAIR RNA expression with increasing doses of TA. FIG. 9B illustrates decreased cell proliferation with increasing dose over time. FIG. 9C illustrates downregulation of several Sp-regulated genes (EZH2, cyclin D1 and cyclin E) in MDA-MB-231 breast cancer cells with increasing doses of TA. FIG. 9D illustrates that Sp1 knockdown by RNAi results in decreased expression of oncogenic miRNAs that form the miR-17-92, miR-106b-25 and miR-106a-363 clusters. ** decreased with significance of $p<0.05$.

FIGS. 13A and 13B illustrate the effect of MALAT-1 knockdown using two siRNAs (I and II) on Panc28 cells. MALAT-1 knockdown induces PARP cleavage (FIG. 13A) and inhibits phosphorylation of AKT/Erk (FIG. 13B). Similar results were observed in Panc1 cells (data not shown). siMALAT-2 was the most effective agent for knockdown in Panc28 cells.

FIG. 14 illustrates the reduction of MALAT-1 expression (RNA abundance) caused by knockdown of Sp1/3/4 TFs with a combined siSp1/3/4.

FIG. 19A illustrates the reduction of tumor growth caused by the knockdown as a function of time (days). FIG. 19B illustrates the reduction in tumor weight caused by the knockdown.

FIG. 20A illustrates the significant suppression of AY1239027 and HULC expression in HepG2 cells at 72 hours after transfection with siSp1. FIG. 20B illustrates the significant suppression of AY1239027 and HULC expression in HeLa cells at 72 hours after transfection with siSp1. FIG. 20C illustrates the significant suppression of AY1239027, linc-HEIH, HOTAIR, and HULC expression in HepG2 cells at 72 hours after transfection with siSp1.

FIG. 24A illustrates the significant reduction of Sp1, AY1239027, and HULC expression 48 hours after administration of 2.5 μM $CF_3$DODA-Me. FIG. 24B illustrates the significant reduction of Sp1, AY1239027, and HULC expression 48 hours after administration of 1 μM $CF_3$DODA-Me.

DETAILED DESCRIPTION

Figure 1A:
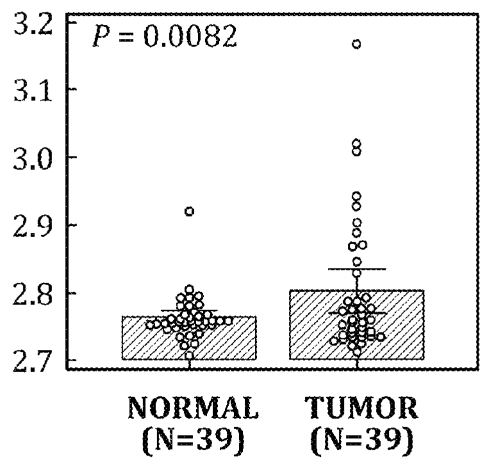
FIGS. 1A-1D illustrate HOTAIR expression and prognostic significance in pancreatic cancer.

Protein-encoding genes make up only a small fraction of the human genome. Recent studies show that other regions encode for short, medium or long non-coding RNA (ncRNAs), which are largely uncharacterized, although there has been some effort to explore their role in cancer (Cancer Res 71:3 (2011)). Recently ~3000 human long intervening non-coding RNAs (lncRNAs) have been identified and biological characterization studies suggest that lncRNAs have important functions in both normal and cancer tissues. There is evidence that many lncRNAs act as molecular scaffolds that regulate molecular (protein, RNA, DNA) interactions required for various signaling networks and this is accomplished, in part, by association with chromatin-modifying complexes. HOTAIR is a 2,158 bp lncRNA localized to a boundary in the HOXC gene cluster, and HOTAIR is a negative prognostic factor for breast and liver cancer patient survival (and enhanced breast cancer metastasis) (Rinn et al., Cell (2007) 129:1311-132). RNA interference and overexpression studies demonstrate the pro-oncogenic activity of HOTAIR. Increased HOTAIR expression in breast cancer patients, for example, predicts decreased patient survival and increased metastasis, and overexpression of HOTAIR increased breast cancer cell and tumor invasion in animal models and cell culture (Nature 464:1071 (2010)). The activity of HOTAIR is due, in part, to HOTAIR interactions with Polycomb Repressive Complex 2 (EZH2, SUZ12 and EED) which enhances H3K27 trimethylation to decrease expression of multiple genes. Other lncRNAs also associate with PRC2 and chromatin complexes, suggesting potential activity similar to that described for HOTAIR.

Specificity protein 1 (Sp1) is a member of the Sp/Kruppel-like factor (KLF) family of transcription factors. These proteins are characterized by their C-terminal domains which contain three C2H2-type zinc fingers that recognize GC/GT boxes in promoters of target genes. The N-terminal domains of Sp/KLF proteins are highly variable in both structure and function and many KLF proteins are truncated in this region. Some Sp/KLF members are critical for embryonic development. Knockout of Sp1, Sp3 and Sp4 genes in mice results in embryo lethality or multiple developmental deficits. Sp and KLF proteins cooperatively interact with one another and other transcription factors on GC-rich promoters to activate or inhibit diverse classes of mammalian and viral genes that play a critical role in regulating cellular homeostasis.

The tissue- and age-dependent expression of Sp proteins in humans and laboratory animal models has not been extensively investigated, however, several studies report that Sp1, Sp3 and Sp4 proteins are overexpressed in tumor vs. non-tumor tissues. For example, in gastric cancer Sp1 expression was observed in tumor cells; whereas in stromal and normal glandular cells, Sp1 expression was either weak or non-detectable. Moreover, survival of gastric cancer patients increased with decreasing Sp1 protein expression. Malignant transformation of human fibroblasts resulted in an 8- to 18-fold increase in Sp1 expression and the transformed cells formed tumors in athymic nude mouse xenografts, whereas Sp1 knockdown gave cells that were non-tumorigenic in the same mouse xenograft model. Using RNA interference, it was shown that Sp1 knockdown using a small inhibitory RNA (siRNA) for Sp1 (iSp1) inhibited G0/G1 to S phase progression in MCF-7 breast cancer cells. siRNAs for Sp3 (iSp3) and Sp4 (iSp4) were used along with iSp1 to show that in pancreatic cancer cells, Sp1, Sp3 and Sp4 proteins regulated expression of vascular endothelial growth factor (VEGF), VEGF receptor 1 (VEGFR1 or Flt) and VEGFR2 (KDR) (20-22). Moreover, Sp3 acted as a repressor of p27 in pancreatic cancer cells, indicating that overexpression of Sp proteins in cancers contribute to their proliferative and angiogenic phenotype. However, underlying factors associated with high expression of Sp proteins, such as Sp1, Sp3 and Sp4 in tumors are not well understood.

As described in more detail below, the inventors have discovered that SpTFs regulate many ncRNAs, and drugs that downregulate SpTFs also downregulate several pro-oncogenic ncRNAs. Because these ncRNAs are often overexpressed in cancer cells, this novel discovery presents additional target for cancer therapies. Additionally, this discovery provides novel opportunities to identify cancer patients exhibiting overexpression of ncRNAs as better candidates for therapy with SpTF drugs than those patients exhibiting expression of Sp TF alone, to predict the response of subject to such therapy, and to monitor efficacy of treatments using such therapies.

In accordance with the foregoing, in one aspect the disclosure provides a method of inhibiting growth of a cell characterized by overexpression of at least one specificity protein (Sp)-regulated non-coding RNA (ncRNA) and expression of at least one Sp transcription factor (SpTF). The method comprises contacting the cell with an effective amount of an SpTF agent.

In some embodiments, the cell is a transformed cell. As used herein, the term "transformed" means a cell that comprises an alteration from a healthy, normal state, for example, loss of an aspect of control over a normal, regulated cell-cycle. The cells can be a neoplastic cell, a precancerous cell, or malignant neoplasm (cancer) cell. Consequent to a loss of normal cell-cycle regulation, the cell can develop and/or proliferate at an enhanced rate, thus potentially giving rise to a cell-proliferative disease, such as cancer.

Cancers (or cancer cells) discussed herein can be any type of cancer, such as a carcinoma, sarcoma, lymphoma, leukemia, melanoma, mesothelioma, multiple myeloma, or seminoma. A cancer can be a metastatic cancer. The cancer cells can be derived from solid or non-solid tumors. A cancer can be a recurrent cancer, such as recurrent liver cancer following liver transplant therapy. Cancers and cancer cell types contemplated herein include, but are not limited to: adrenal cancer, anal cancer, bladder cancer, blood cancer, bone cancer, brain cancer, breast cancer, cervical cancer, chronic or acute leukemia, CNS cancer, colon cancer, cutaneous or intraocular melanoma, endocrine cancer, endometrial carcinoma, esophageal cancer, fallopian tube carcinoma, follicular lymphoma and other non-Hodgkin's lymphomas, head or neck cancer, Hodgkin's disease, kidney cancer, larynx cancer, large intestinal cancer, liver cancer, lung cancer, lymphocytic lymphoma, ovarian cancer, pancreatic cancer, parathyroid cancer, penile cancer, pituitary adenoma, primary CNS lymphoma, prostate cancer, rectal cancer, renal cell carcinoma, renal pelvic cancer, skin cancer, small cell lung cancer, small intestinal cancer, soft tissue tumor, spleen cancer, stomach cancer, testicular cancer, thyroid cancer, ureter cancer, urethral cancer, uterine cancer, vaginal cancer, and vulval cancer, or a combination thereof. In some embodiments, as described in more detail below, the cancer cells are pancreatic cancer, hepatic (liver) cancer, breast cancer, or cervical cancer.

As used herein, "inhibiting the growth" means slowing or reducing the overall rate of cell growth and/or proliferation (i.e., division). While in many embodiments, the ideal scenario is to completely arrest cell proliferation, including killing the cell(s), it will be understood that inhibition encompasses all intermediate degrees of slowing or reducing the rates of cell growth and/or proliferation.

As used herein, "overexpress" and grammatical variants thereof refer to an expression level (of a gene) in cell or sample of cells (e.g., cell, tissue) that is greater than the level in a reference standard. One will appreciate that a reference standard can vary depending on the situation. For example, the reference standard can include a cell or sample of cells that provide a reference expression level of the same gene. The reference standard cell(s) can be healthy cells from the same source tissue as the target cell(s). In other embodiments, the reference standard cell(s) can of the same type, but from a different source subject(s) or determined to be healthy. In other embodiments, the reference standard can be a particular threshold established in the art that is considered to be a normal, or typical gene expression level. Often, expression levels for any specific gene are conveyed in relative terms in relation to control genes that are known to have relatively constant expression rates, such as GAPDH and Actin. Levels of expression can be determined according to any of many acceptable protocols known in the art that measure the abundance of encoding RNA (e.g., mRNA), such as quantitative or semi-quantitative polymerase chain reaction (PCR), northern blot. In other embodiments applicable to protein-coding genes, the expression can be quantified in terms of amount of target protein detected, such as by western blot. In some embodiments, overexpression is at least twice, three, four, five, or ten times or more the expression level of the reference standard. In some embodiments, overexpression is merely some fraction over one times the expression level of the reference standard. In some embodiments, overexpression refers to the average expression level of several control samples.

As described above, the genome contains many regions, or genes, that encode RNA that is not used as a template for translation to create a polypeptide. These RNA products, called "non-coding RNAs," or "ncRNAs," are widely variable in length and have been found to be involved in gene regulation. Accordingly, in some embodiments, the ncRNA is a large non-coding RNA (lncRNA). Nonlimiting examples of lncRNAs include HOTAIR, HOTAIRM, HOTTIP, MALAT-1, linc-HEIH, HULC, and AY12907, all of which are known in the art. In other embodiments, the ncRNA is a microRNA (miR). Nonlimiting examples of miRs include miR-27a, miR-21, and miR-181b. See, e.g., *Cell* 133:217 (2008). ncRNAs encompassed by the present invention are regulated by specificity protein transcription factors (SpTFs), which are described in more detail below. ncRNAs thus regulated can be identified using arrays for ncRNAs and comparing their expression in untreated cells and cells in which specificity proteins are knocked down by RNA interference (illustrative methods are demonstrated in more detail below). Many of the arrays are commercially available (e.g., Applied Biosystems) and can be used for screening large numbers of ncRNAs at the same time.

As indicated, HOTAIR is an exemplary a large ncRNA (lncRNA) (*Cell* 129:1311 (2007); *Nature* 464:1071 (2010)). Expression determinations of lncRNAs, such as HOTAIR, can be routinely carried out by RT-PCR in patient tissue or cells. See, e.g., FIG. 1D. (See also Yang et al., *Ann. Surg. Oncol*., published online February 2011; *Nature* 464:1071 (2010)). One can examine the relevancy of HOTAIR expression in other cancers, such as in tumors or cell lines. For example, to examine HOTAIR expression as it relates to prognostic significance, one can perform data mining of cancer patient arrays and correlate low vs. high HOTAIR expression and patient survival. See, additional descriptions below and *Nature* 464:1071 (2010). To examine the functional significance of HOTAIR expression, one can knock down HOTAIR in cells. If the cells exhibit decreased growth and growth promoting genes and decreased invasion, then HOTAIR functions as a tumor growth promoter and facilitates invasion. See FIGS. 2A-2D and 3A-3C herein and the accompanying descriptions. See also Yang et al., *Ann. Surg. Oncol*., published online February 2011.

As used herein, an "Sp transcription factor" or "SpTF" refers to a member of the specificity protein (Sp)/Kruppel-like factor (KLF) family of zinc finger transcription factors. Non-limiting examples of Sp transcription factors include Sp1, Sp2, Sp3, Sp4, Sp5, Sp6, Sp7, and Sp8. In some embodiments, the SpTF is one of Sp1, Sp3, and Sp4. Any standard method of detection expression of an SpTF can by used. Such methods of are well-known in the art. See, e.g., U.S. patent application Ser. No. 2010/0099760, incorporated herein by reference in its entirety. In some embodiments, an Sp transcription factor can be overexpressed, as defined above.

The term "contact," when applied to a cell, is used herein to describe the process by which an agent or composition described herein is delivered to a target cell or is placed in direct juxtaposition with the target cell.

In some embodiments, a small inhibitory RNA (siRNA) or combination thereof can be used in addition to an Sp transcription factor agent described herein. Non-limiting examples of siRNAs include iSp1, iSp3, and iSp4, and combinations thereof. See, e.g., below and *Mol. Cancer. Ther.* 8:739 (2010).

In any embodiment herein, a cell can be in vitro, such as a cell in culture, or in vivo within a living subject. Accordingly, in some embodiments, the cell is derived from or comprised in a sample obtained from a subject having a cell proliferative disease or suspected of having a cell proliferative disease, such as a cancer. For example, the cell can be comprised in a sample obtained from a subject by a biopsy procedure, and the method can be performed on it. In other embodiments, the cell can be a progeny (by cell division) of a progenitor cell obtained from a subject.

In another aspect, the disclosure provides a method of reducing the expression of at least one specificity protein (Sp)-regulated non-coding RNA (ncRNA) in a cell that also expresses at least one Sp transcription factor (SpTF), the method comprising contacting the cell with an effective amount of an SpTF agent. As above, the cell can be in vitro, such as a cell in culture, or in vivo within a living subject.

In another aspect, the disclosure provides a method of treating a cell proliferative disease, the method comprising administering to a subject in need a therapeutically effective amount of an specificity protein transcription factor (SpTF) agent, wherein the subject has at least one transformed cell characterized by the overexpression of at least one specificity protein (Sp)-regulated non-coding RNA (ncRNA) and the expression of at least one SpTF.

As used herein, the term "treating" includes, but is not limited to, inhibiting, slowing, or arresting the growth of cells (e.g., transformed or cancer cells), or killing the cells, or a slowing, stopping or reducing the volume or weight of a mass comprising the same. This also encompasses reducing the number of cells in a mass, such as a tumor. Inhibiting the growth refers to slowing or halting any increase in the size or the number of transformed (e.g., cancer) cells or a mass comprising the same, or to halting the division of the cancer cells. Reducing the size refers to reducing the size (in terms of volume or weight) of a mass comprising the cells, or reducing the number of or size of the same cells.

As used herein, the term "patient" or "subject" refers to a living mammalian organism, such as a human, monkey, cow, sheep, goat, dog, cat, mouse, rat, guinea pig, or transgenic species thereof. In some embodiments, the patient or subject is a primate. Non-limiting examples of human subjects are adults, juveniles, infants, and fetuses. A patient can be a patient having cancer. A patient or subject can be suspected of having cancer.

In some embodiments, the specificity protein transcription factor (SpTF) agents comprised in a pharmaceutically acceptable composition. "Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

An "effective amount" of an agent or composition, generally, is defined as that amount sufficient to detectably and repeatedly achieve the stated desired result, for example, to ameliorate, reduce, minimize or limit the extent of a disorder (e.g., a cell proliferative disease such as cancer) or its symptoms or to increase, stimulate, or promote a desirable physiological response.

A "therapeutically effective amount" or a "pharmaceutically effective amount" or a "pharmacologically effective amount" means that amount which, when administered to a subject or patient for treating a disease, is sufficient to effect such treatment or therapy for the disease.

In another aspect, the disclosure provides a method of predicting the response of a subject with a cell proliferative disease to a specificity protein transcription factor (SpTF) agent-based treatment. The method comprises (i) determining the expression level of at least one specificity protein (Sp)-regulated non-coding RNA (ncRNA) in a cell sample obtained from the subject, (ii) determining the expression status of at least one specificity protein transcription factor (SpTF) in the same or similar cell sample obtained from the subject, and (iii) predicting a positive response of the subject with a cell proliferative disease to treatment with an SpTF agent when the at least one Sp-regulated ncRNA is overexpressed in the cell sample and the SpTF is expressed in the same or similar cell sample.

As used herein, the term "positive response" means that the result of treatment includes some benefit, such the prevention, or reduction of severity, of symptoms, or a slowing of the progression of the disease. This can include the reduction of growth, replication and/or development of a transformed (e.g., cancer) cell.

In some embodiments, the overexpression of the at least one Sp-regulated ncRNA is determined by comparing the expression of the Sp-regulated ncRNA in the cell sample to a reference standard, as defined above. In some embodiments, comparing the expression of the Sp-regulated ncRNA in the cell sample to a reference standard comprises comparing the expression level of the at least one Sp-regulated ncRNA to the expression level of the at least one Sp-regulated ncRNA in a noncancerous cell derived from the same tissue. In some embodiments, the method further comprises administering an SpTF agent to the subject that is predicted to have a positive response to treatment.

The term "cell sample" is intended to convey that expression levels of the can be determined from one cell or a plurality of cells obtained in aggregate. In the latter case, the cells can have been obtained from a single location in the subject's body, such as a biopsy sample. Thus a cell sample can comprise one or more cells, or consist of a single cell.

The term "same or similar" as used in connection with cell sample is intended to mean that the cell sample can be used to determine the expression levels of both the SpTF-regulated ncRNA and the SpTF, or the expression levels can be determined from distinct cell samples that are similar. The term "similar" is intended to mean that the expression level determined from one sample is understood to be meaningful to infer the expression level of the same gene in the other sample, and vice versa. In some embodiments, the separate but similar cell samples are from the same tissue, and possibly from the proximate locations from the body of the subject. In other embodiments, the cells comprising the similar samples are the same types of cells or are derived from the same progenitor cells.

The term "determining" or grammatical equivalents thereof refers to performing a quantitative analysis.

In another aspect, the disclosure provides a method of monitoring the efficacy of a specificity protein transcription factor (SpTF) agent-based treatment in a subject with a cell proliferative disease. The method comprises: (i) determining the expression level of at least one specificity protein (Sp)-regulated non-coding RNA (ncRNA) in a first cell sample obtained from the subject, (ii) administering at least one SpTF agent to the subject, and determining the expression level of the at least one Sp-regulated ncRNA in a second cell sample obtained from the subject. In this method, the second cell sample is obtained from the same or similar cell source within the subject, and the second cell sample is obtained from the subject at a time after the first cell sample is obtained and after the at least one SpTF agent is administered to the subject. The treatment is determined to be effective when the expression level of the Sp-regulated ncRNA is lower in the second sample than in the first sample.

An SpTF agent-based treatment is one that comprises administration of an agent that modifies, i.e., suppresses, expression or action of an SpTF. These are described in more detail below.

In this method a subject can be monitored at multiple time points including before, during initiation of treatment, and at one or more time points after the initiation of treatment. Accordingly, at least a first and second cell samples are obtained from the subject. In some embodiments, the at least first and second cell samples are obtained from the same or similar cell source from within the body. It will be understood that the similarity of the cell sources (e.g., locations within the body) will provide cell(s) that provide a meaningful comparison of expression levels in a temporal context. Thus, in some embodiments, the cell(s) comprising the cell samples are of the same type, from the same location or tissue, or are derived from the same progenitor cells. When a determination of reduced expression levels in a second (or further subsequent), an inference is made that the administration of the SpTF agents have resulted in a suppression of ncRNAs, and thus, a reduction or amelioration in their pro-oncogenic effects.

In another aspect, the disclosure provides a method of evaluating a candidate specificity protein transcription factor (SpTF) agent for use in treatment of a cell proliferative disease. The method comprises: contacting a candidate SpTF agent to a cell characterized by (a) overexpression of at least one specificity protein (Sp)-regulated non-coding RNA (ncRNA), and (b) expression of an SpTF. The method further comprises determining the expression level of the at least one Sp-regulated ncRNA subsequent to the contacting step, and comparing the expression level of the at least Sp-regulated ncRNA to a reference standard, wherein a reduced expression level of the at least Sp-regulated ncRNA in comparison to the reference standard is indicative of the efficacy of the candidate SpTF agent for treatment of a cell proliferative disease. In some embodiments, the cell is obtained from a plurality of similar cells, and wherein the reference standard comprises one or more cells obtained from the same plurality of similar cells, such as a plurality of cells obtained from a tumor mass, that are not contacted with the SpTF agent. In some embodiments, the cell and the reference standard comprises a non-cancerous cell derived from the same tissue as the cancer cell.

Also provided are compositions comprising one or more Sp transcription factor agents. For example, provided herein is a composition comprising an amount of an Sp transcription factor agent that is effective to downregulate expression of both (i) HOTAIR, other Sp-regulated ncRNA(s), or combination thereof, and (ii) an Sp transcription factor. Such downregulation can result in alteration of a pro-oncogenic response in an assay system (e.g., growth, migration, invasion, and metastasis). A composition can comprise a therapeutically effective amount of an Sp transcription factor agent. Any composition described herein can be further defined as a pharmaceutical composition.

The term "alkyl", when used alone or in combination with other groups or atoms, refers to a saturated straight or branched chain consisting solely of 1 to 6 hydrogen-substituted carbon atoms, such as 1 to 4 hydrogen-substituted carbon atoms, and includes methyl, ethyl, propyl, isopropyl, n-butyl, sec-butyl, isobutyl, t-butyl, 2,2-dimethylbutyl, n-pentyl, 2-methylpentyl, 3-methylpentyl, 4-methylpentyl, n-hexyl and the like.

The term "alkenyl" refers to a partially unsaturated straight or branched chain consisting solely of 2 to 6 hydrogen-substituted carbon atoms that contains at least one double bond, and includes vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

The term "alkynyl" refers to a partially unsaturated straight or branched chain consisting solely of 2 to 8 hydrogen-substituted carbon atoms that contains at least one triple bond, and includes ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl, 4-methylpent-2-ynyl, 1-hexynyl and the like.

The term "aryl" refers to an aromatic mono- or bicyclic group containing from 6 to 14 carbon atoms that can be optionally fused with a fully or partially saturated carbocyclic ring and can optionally be substituted with one or more substituents, such as one to three substituents, independently selected from $C_{1\text{-}4alkyl}$, fluoro-substituted $C_{1\text{-}4alkyl}$, halo, $OC_{1\text{-}4alkyl}$, fluoro-substituted $OC_{1\text{-}4alkyl}$, $NO_2$ and CN. Examples of aryl groups include phenyl, naphthyl, indanyl and the like.

The term "heteroaryl" refers to an aromatic mono- or bicyclic group containing from 5 to 14 carbon atoms, of which one to five is replaced with a heteroatom selected from N, S, and O, that can optionally be substituted with one or more substituents, such as one to three substituents, independently selected from $C_{1\text{-}4alkyl}$, fluoro-substituted $C_{1\text{-}4alkyl}$, halo, $OC_{1\text{-}4alkyl}$, fluoro-substituted $OC_{1\text{-}4alkyl}$, $NO_2$ and CN. Examples of aryl groups include thienyl, benzimidazolyl, benzo[b]thienyl, furanyl, benzofuranyl, pyranyl, isobenzofuranyl, chromenyl, xanthenyl, pyrrolyl, imidazolyl, pyrazolyl, pyridyl, pyrazinyl, pyrimidinyl, pyridazinyl, indolizinyl, isoindolyl, indolyl, indazolyl, purinyl, quinolizinyl, isoquinolyl, quinolyl, and the like.

The term "fluoro-substituted" means that, in the group being described, one or more, including all, of the hydrogen atoms has been replaced by F. For example, a fluoro-substituted alkyl includes trifluoromethyl, trifluoroethyl, pentafluoroethyl and the like.

The terms "halogen" and "halo" refer to F, Cl, Br, or I.

Under standard nomenclature rules used throughout this disclosure, the point of attachment of the designated side chain is described first followed by the adjacent functionality toward the terminal portion. A substituent's point of attachment can also be indicated by a dashed line to indicate the point(s) of attachment, followed by the adjacent functionality and ending with the terminal functionality.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

In some embodiments, the Sp transcription factor agent is selected from the group consisting of: (i) a phytochemical or derivative thereof that induces reactive oxygen species (ROS) or phosphatase activity; (ii) a naturally occurring (e.g., celastrol) or synthetic triterpenoid; (iii) an non-steroidal anti-inflammatory drug (NSAID); (iv) an antisense microRNA oligonucleotide; (v) an agent that causes overexpression of ZBTB10, ZBTB4, or related transcriptional repressor; (vi) a thiazolidinedione; (vii) a nitro-aspirin; (viii) an isothiocyanate; (ix) aspirin; (x) arsenic trioxide; (xi) metformin; (xii) silibinin; and (xiii) a cannabinoid. In some embodiments, the Sp transcription factor agent is selected from the group consisting of: (i) an NSAID further defined as a diphenyl/diphenylamine carboxylic acid; (ii) a phytochemical further defined as betulinic acid or derivative or analog thereof, or curcumin or a derivative thereof; and (iii) a naturally-occurring triterpenoid further defined as celastrol or a synthetic triterpenoid further defined as a glycyrrhetinic acid derivative. In some embodiments, the glycyrrhetinic acid derivative is further defined as methyl 2-cyano-3,12-dioxooleana-1,9-dien-28-oate or methyl 2-cyano-3,11-dioxo-18β-olean-1,12-dien-30-oate.

The Sp transcription factor agent can be administered as a pharmaceutically acceptable salt. The term "pharmaceutically acceptable salt" includes both pharmaceutically acceptable acid addition salts and pharmaceutically acceptable basic addition salts. The term "pharmaceutically acceptable acid addition salt" as used herein means any non-toxic organic or inorganic salt of any base compound of the disclosure, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts can exist in either a hydrated, solvated or substantially anhydrous form. In general, the acid addition salts of the compounds of the disclosure are more soluble in water and various hydrophilic organic solvents, and generally demonstrate higher melting points in comparison to their free base forms. The selection of the appropriate salt will be known to one skilled in the art. Other non-pharmaceutically acceptable acid addition salts, e.g., oxalates, can be used, for example, in the isolation of the compounds of the disclosure, for laboratory use, or for subsequent conversion to a pharmaceutically acceptable acid addition salt. The term "pharmaceutically acceptable basic salt" as used herein means any non-toxic organic or inorganic basic addition salt of any acid compound of the invention, or any of its intermediates, which are suitable for or compatible with the treatment of animals, in particular humans. Illustrative inorganic bases that form suitable salts include lithium, sodium, potassium, calcium, magnesium, or barium hydroxide. Illustrative organic bases that form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, can be used, for example, in the isolation of the compounds of the invention, for laboratory use, or for subsequent conversion to a pharmaceutically acceptable acid addition salt. The formation of a desired compound salt is achieved using standard techniques. For example, the neutral compound is treated with a base in a suitable solvent and the formed salt is isolated by filtration, extraction or any other suitable method.

Sp transcription factor agents can exist in a continuum of solid states ranging from fully amorphous to fully crystalline. The term "amorphous" refers to a state in which the material lacks long range order at the molecular level and, depending upon temperature, can exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs that is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Sp transcription factor agents can also exist in unsolvated and solvated forms. The term "solvate" is used herein to describe a molecular complex comprising the agent and one or more pharmaceutically acceptable solvent molecules, for example, ethanol. The term "hydrate" is employed when said solvent is water. A currently accepted classification system for organic hydrates is one that defines isolated site, channel, or metal-ion coordinated hydrates (see *Polymorphism in Pharmaceutical Solids* by K. R. Morris, ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The present invention includes radiolabeled forms of Sp transcription factor agents, for example, compounds of the invention labeled by incorporation within the structure $^{3}H$, $^{11}C$ or $^{14}C$ or a radioactive halogen such as $^{125}I$ and $^{18}F$. A radiolabeled compound of the invention can be prepared using standard methods known in the art. For example, tritium can be incorporated into a compound of the invention using standard techniques, for example by hydrogenation of a suitable precursor to a compound of the invention using tritium gas and a catalyst. Alternatively, a compound of the invention containing radioactive iodo can be prepared from the corresponding trialkyltin (suitably trimethyltin) derivative using standard iodination conditions, such as [$^{125}I$] sodium iodide in the presence of chloramine-T in a suitable solvent, such as dimethylformamide. The trialkyltin compound can be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, such as 50-100° C. Further, a compound of the invention containing a radioactive fluorine can be prepared.

In some embodiments, a "derivative" refers to a chemically modified agent that still retains the desired effects of the agent prior to the chemical modification. As such, "derivatives," therefore, can refer to chemically modified agents that still retain the desired effects of the parent agent prior to its chemical modification. Such effects can be enhanced (e.g., slightly more effective, twice as effective, etc.) or diminished (e.g., slightly less effective, 2-fold less effective, etc.) relative to the parent agent, but can still be considered an Sp transcription factor agent derivative. Such derivatives can have the addition, removal, or substitution of one or more chemical moieties on the parent molecule. Non-limiting examples of the types of modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, imide, and azo groups; sulfate, sulfonate, sulfono, sulfhydryl, sulfenyl, sulfonyl, sulfoxido, sulfonamide, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Any agent or genus of agents discussed herein can be specifically excluded from any embodiment discussed herein. The following is a description of Sp transcription factor (SpTF) agents useful in aspects of this disclosure.

As used herein, a "Sp transcription factor agent" is a molecule that causes downregulation or repression of an Sp transcription factor. Downregulation can occur by increasing expression of an Sp repressor gene in the cell, such as by decreasing expression of a microRNA through contact with the agent. The microRNA can be miR-27a. The Sp repressor gene can be ZBTB10. An agent can also induce Sp transcription factor degradation in proteasome-dependent and caspase-dependent manners. In some embodiments, downregulation or repression results in an alteration of a pro-oncogenic response in an assay system (e.g., growth, migration, invasion, metastasis). Any agent that downregulates or represses an Sp transcription factor can be employed in embodiments herein. Sp transcription factor agents include all polymorphs and crystal forms thereof, salts, prodrugs and isomers thereof (including optical, geometric and tautomeric isomers) and isotopically-labeled agents. In some embodiments, the molecular weight of the agent is 10,000 g/mol or less.

Numerous agents that downregulate or repress Sp transcription factors that are overexpressed in tumors and cancer cells have been identified, including arsenic trioxide, NSAIDs (tolfenamic acid and related compounds), phytochemicals (curcumin and betulinic acid), and synthetic triterpenoids. See, e.g., *Int. J. Cancer* 125:1965 (2009); *Cancer Res.* 68:5345 (2008); *Carcinogenesis* 30:1193 (2009); *Can-*

*cer Res.* 67:2816 (2007); *Cancer Res.* 67:11001 (2007); *Mol. Cancer. Res.* 8:739 (2010); *Exper. Cell Res.* 316:2174 (2010); *Mol. Pharmacol.* 78:226 (2010); *J. Biol. Chem.* 285:25332 (2010); *J. Nat'l Cancer Inst.* 98:855 (2006); *Cancer Res.* 67:3286 (2007); *Mol. Cancer. Ther.* 8:533 (2009). Categories of Sp transcription factor agents are not necessarily mutually exclusive: that is, a particular agent can be a member of one or more agent categories.

In some embodiments, the Sp transcription factor agent is a non-steroidal anti-inflammatory drug, such as diphenyl/diphenylamine carboxylic acid (e.g., tolfenamic acid, diclofenac sodium, diflunisal), as disclosed in U.S. Publ. Appl. Nos. 2007/0259829 2008/0261911, each of which is incorporated herein by reference in its entirety. In some embodiments, the agent is betulinic acid or an analog or derivative thereof as disclosed in U.S. Publ. Appl. No. 2009/0203661, incorporated herein by reference in its entirety. The agent can act as a PPARγ agonist as well as degrade Sp transcription factor(s), such as the glycyrrhetinic acid derivatives disclosed in U.S. Publ. Appl. No. 2010/0099760, incorporated herein by reference in its entirety. In some embodiments, the agent is a microRNA antisense oligonucleotide, such as those described in U.S. Publ. Appl. No. 2009/0099123, incorporated herein by reference in its entirety. In some embodiments, the agent is methyl 2-cyano-3,11-dioxo-18β-olean-1,12-dien-30-oate (CDODA-Me), such as described in U.S. Publ. Appl. Nos. 2010/0099760 and 2009/0099123, noted above. In some embodiments, the agent is methyl 2-cyano-3,12-dioxooleana-1,9-dien-28-oate (CDDO), as described in *Mol. Pharmacol.* 78:226 (2010). In some embodiments, the agent is curcumin, such as described in *Cancer Res.* 68:5345 (2008) and *J. Biol. Chem.* 285:25332 (2010). In some embodiments, the agent is arsenic trioxide, such as described in *Exper. Cell Res.* 316:2174 (2010).

In some embodiments, the Sp transcription factor agent is a betulinic acid analog or derivative having the following formula:

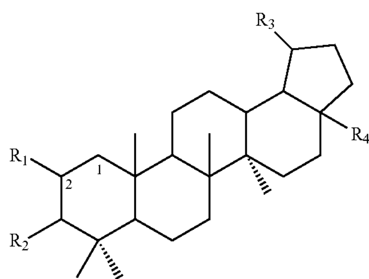

wherein a bond between C1 and C2 is a single bond or a double bond; R1 is H, CN, Cl, Br, F, I, CH3, CF3, OCH3, N(CH3)2, or phenyl; R2 is OH or ═O; R3 is COOH, $COOC_{1\text{-}4alkyl}$, COONH2, $COONH(C_{1\text{-}4alkyl})$, $COON(C_{1\text{-}4alkyl})_2$, or CHO; and R4 is CH(CH3)2 or C(CH3)═CH2; or a pharmacologically effective salt or hydrate thereof. In some embodiments, a bond between C1 and C2 is a single bond or a double bond, R1 is H, CN, Cl, Br, F, 1, CH3, CF3, OCH3, $N(CH3)_2$, or phenyl; R2 is OH or ═O; R3 is COOH, COOCH3, COOCH2CH3, or CHO; and R4 is CH3, CH(CH3)2 or C(CH3)═CH2; or a pharmacologically effective salt or hydrate thereof. In one aspect R1 can be Cl, Br or CN. In another aspect R2 can be ═O. In yet another aspect R3 can be COOH or COOCH3. In yet another aspect C1-C2 is a double bond, R1 can be CN, R2 can be ═O and R3 can be COOH or COOCH3. In yet another aspect R1 can be Cl or Br, R2 can be ═O, and R3 can be COOCH2CH3 or CHO. In some embodiments, a bond between C1 and C2 is a single bond or a double bond, R1 is CN, CH3, CF3, OCH3, $N(CH3)_2$, or phenyl, R2 is OH or ═O, R3 is COOH, COOCH3, COOCH2CH3, or CHO, and R4 is CH(CH3)2 or C(CH3)═CH2 or comprises a pharmacologically effective salt or hydrate thereof. In some embodiments, R1 can be CN, R2 can ═O and R3 can be COOH or COOCH3. Also, the substituent R3 can be COOCH2CH3 or CHO where R1 further comprises Cl, Br, F, or I. In some embodiments, a single or a double bond can be formed between carbons C1 and C2. R1 can be hydrogen, a cyano group, a halide, i.e., chlorine, bromine, fluorine or iodine, an alkyl group, e.g., methyl, a haloalkyl group, e.g., trifluoromethyl, an alkylamine, e.g., dimethyl amine, an alkoxy group, e.g., methoxy, or a phenyl group. R2 can be hydroxy or a carbonyl oxygen. R3 can be a carboxy group, an alkyl ester, e.g., a C1-C4 alkyl ester, preferably methyl ester or ethyl ester, an aldehyde, e.g., formaldehyde, or an amide or alkyl substituted amide, which can be further substituted, R4 can form the dihydro isopropyl moiety CH(CH3)2 or can form the methylethylene moiety C(CH3)═CH2, as in betulinic acid or betulonic acid. R1 can be a cyano group, a chlorine or a bromine. Also, in another embodiment R2 is a carbonyl oxygen. In yet another embodiment, R3 is a carboxy group or the ester, particularly, the methyl or ethyl ester, thereof. Alkyl substituents can be straight- or branched-chain or cycloalkyl or, for longer chains, can be the alkenyl or alkynyl derivative.

Betulinic acid analogs and derivatives can be synthesized using well-known and standard techniques in the chemical synthetic arts. Generally, these compounds can be, although not limited to, betulinic acid, dihydrobetulinic acid, the keto analogs betulonic acid and dihydrobetulonic acid, and derivatives thereof substituted at, although not limited to, one or more of C2 or C28. In preferable non-limiting examples, a 2-cyano group is introduced into the lupane skeleton of 20(29)-dihydro betulinic acid or the corresponding methyl ester is used.

In some embodiments, an Sp transcription factor agent is a glycyrrhetinic acid derivative of the following formula:

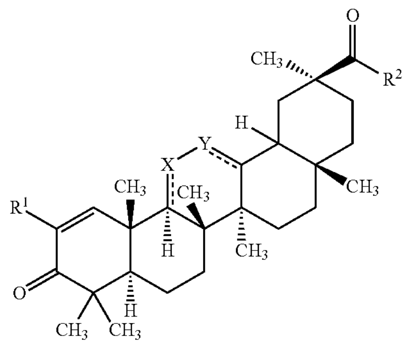

wherein R1 is selected from CN, halo, NO2, CO2R3, $C_{1\text{-}6\ alkyl}$, fluoro-substituted $C_{1\text{-}6alkyl}$, $C_{2\text{-}6alkenyl}$, $C_{2\text{-}6alkynyl}$, OR3, SR3, SOR3, SO2R3, NR3R4, C(O)NR3R4, C(O)R3, OC(O)R3, NHC(O)R3, P(O)R3R4, —C≡C—R3, —CR3═CR4R5, aryl and heteroaryl; R2 is selected from $OC_{1\text{-}6alkyl}$, fluoro-substituted $OC_{1\text{-}6alkyl}$, NH2, $NHC_{1\text{-}6alkyl}$, $N(C_{1\text{-}6alkyl})(C_{1\text{-}6alkyl})$, SH and $SC_{1\text{-}6alkyl}$; R3, R4 and R5 are independently selected from H, $C_{1\text{-}6}$alkyl, fluoro-substituted $C_{1\text{-}6}$alkyl, aryl and heteroaryl; and one of X and Y is C═O while the other is CH2, and if X is C═O then ═ adjacent to X represents a single bond and ⎓ adjacent to Y represents a double bond and if Y is C═O then ⎓ adjacent to Y represents a single bond and ⎓ adjacent to X represents a double bond; and pharmaceutically acceptable salts, solvates, and prodrugs thereof. Glycyrrhetinic acid derivatives can be prepared using methods known in the art. For example, 18α- and 18β-glycyrrhetinic acid and their methyl esters can be converted into the corresponding dienones by reaction with 2-iodoxybenzoic acid as is known (*J. Amer. Chem. Soc.* 124:2245 (2002)). The corresponding 1-saturated-2-cyano 18β-glycyrrhetinic acid and 1-saturated-2-cyano 18α-glycyrrhetinic acid and their methyl esters are known (EP 0009801) and can be reacted with 2,3-dichloro-5,6-dicyano-1,4-benzoquinone (DDQ) to give the corresponding 2-cyano-dienones. Further, dienones of 18α- and 18β-glycyrrhetinic acid and their methyl esters can be iodinated at position 3 by reacting with iodine and pyridine in an ether solvent as described in U.S. Publ. Appl. No. 2010/0099760.

In some embodiments, an Sp transcription factor agent is an antisense microRNA oligonucleotide. An antisense microRNA oligonucleotide can be antisense microRNA-27a. Representative examples of antisense microRNA-27a oligonucleotide sequences can be 5'-CCA CAC CAA GUC GUG UUC ATT-3' (set forth herein as SEQ ID NO:22) and 5'-UGA ACA CGA CUU GGU GUG GTT-3' (set forth herein as SEQ ID NO:23). As is known in the art, an antisense RNA oligonucleotide complements all or part of the microRNA sequence and is of sufficient length that hybridization to the microRNA prevents its interaction with Sp repressor and other regulator genes such at Myt-1 and Wee-1. Also, the antisense oligonucleotides can be stabilized using various derivatives including one or more of a morpholino group, a 2-O-methyl group and phosphorothioate derivatives. In addition one or more of the nucleotides comprising the oligonucleotide can be modified per se. Delivery of the antisense oligonucleotides can be achieved via cationic lipids, polymer complexes, liposomes, and other representative procedures well known and standard in the art which are effective to target and/or contact a cell of interest.

The following is a description of pharmaceutical formulations and routes of administration useful for aspects of this disclosure.

Pharmaceutical compositions comprise an effective amount or a therapeutically effective amount of one or more Sp transcription factor agents dissolved or dispersed in a pharmaceutically acceptable carrier. The preparation of a pharmaceutical composition that contains at least one agent will be known to those of skill in the art in light of the present disclosure, as exemplified by *Remington's Pharmaceutical Sciences,* 18th Ed. Mack Printing Company, 1990. Moreover, for animal (e.g., human) administration, it will be understood that preparations should meet sterility, pyrogenicity, general safety and purity standards as required by the FDA.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, *Remington's Pharmaceutical Sciences,* 18th Ed. Mack Printing Company, 1990, pp. 1289-1329). Except insofar as any conventional carrier is incompatible with the active ingredient, its use in the therapeutic or pharmaceutical compositions is contemplated.

Sp transcription factor agents described herein can be administered by a variety of methods, e.g., orally or by injection (e.g., subcutaneous, intravenous, intraperitoneal, etc.). Depending on the route of administration, an agent can be coated in a material to protect the agent from the action of acids and other natural conditions which can inactivate the agent. Agents can also be administered by continuous perfusion/infusion of a disease or wound site.

The agent can be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations can contain a preservative to prevent the growth of microorganisms.

To administer an agent by other than parenteral administration, it can be necessary to coat the agent with, or co-administer the agent with, a material to prevent its inactivation. For example, the agent can be administered in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the Sp transcription factor agent in the required amount in an appropriate solvent with one or a combination of ingredients enumerated above, as required, followed by filtered sterilization. Generally, dispersions are prepared by incorporating the agent into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder, plus any additional desired ingredient from a previously sterile-filtered solution.

An agent can be orally administered, for example, with an inert diluent or an assimilable edible carrier. The agent and other ingredients can also be enclosed in a hard or soft shell gelatin capsule, compressed into tablets, or incorporated directly into a subject's diet. For oral therapeutic administration, the agent can be incorporated with excipients and used in the form of ingestible tablets, buccal tablets, troches, capsules, elixirs, suspensions, syrups, wafers, and the like. The percentage of the agent in the compositions and preparations may, of course, be varied. The amount of the agent in therapeutically useful compositions (e.g., pharmaceutical compositions) is such that a suitable dosage will be obtained.

It is especially advantageous to formulate parenteral compositions in dosage unit form for ease of administration and uniformity of dosage. "Dosage unit form" as used herein refers to physically discrete units suited as unitary dosages for the subjects to be treated, each unit containing a predetermined quantity of agent calculated to produce the desired therapeutic effect in association with the required pharmaceutical carrier. The specification for the dosage unit forms of the invention are dictated by and directly dependent on (a) the unique characteristics of the agent and the particular therapeutic effect to be achieved, and (b) the limitations inherent in the art of compounding such an agent for the treatment of a selected condition in a patient.

The agent can also be administered topically to the skin, eye, or mucosa. Alternatively, if local delivery to the lungs is desired the agent can be administered by inhalation in a dry-powder or aerosol formulation.

Agents are typically administered at a dosage sufficient to treat a condition associated with a condition in a patient. The actual dosage amount of an agent or composition comprising an agent administered to a subject can be determined by physical and physiological factors such as age, sex, body weight, severity of condition, the type of disease being treated, previous or concurrent therapeutic interventions, idiopathy of the subject and on the route of administration. These factors can be determined by a skilled artisan. The practitioner responsible for administration will typically determine the concentration of agent(s) in a composition and appropriate dose(s) for the individual subject. The dosage can be adjusted by the individual physician in the event of any complication.

An effective amount or therapeutically effective amount can vary from about 0.001 mg/kg to about 1,000 mg/kg in one or more dose administrations daily, for one or several days (depending, of course, of the mode of administration and the factors discussed above). In some embodiments, the amount is less than 10,000 mg per day. In another non-limiting example, a dose can comprise from about 1 microgram/kg/body weight of agent to about 1,000 mg/kg/body weight or more per administration, and any range derivable therein. In some embodiments, a pharmaceutical composition can comprise, for example, at least about 0.1% of an Sp transcription factor agent. In other embodiments, an agent can comprise between about 2% to about 75% of the weight of the pharmaceutical composition unit.

Single or multiple doses of agents are contemplated. Desired time intervals for delivery of multiple doses can be determined by one of ordinary skill in the art employing no more than routine experimentation. As an example, subjects can be administered two doses daily at approximately 12 hour intervals. In some embodiments, the agent is administered once a day. The agent(s) can be administered on a routine schedule. As used herein a routine schedule refers to a predetermined designated period of time. The routine schedule can encompass periods of time which are identical or which differ in length, as long as the schedule is predetermined. For instance, the routine schedule can involve administration twice a day, every day, every two, three, four, five, or six days, or on a weekly or monthly basis, or any set number of days or weeks there-between. Alternatively, the predetermined routine schedule can involve administration on a twice daily basis for the first week, followed by a daily basis for several months, etc. In other embodiments, the invention provides that the agent(s) can taken orally and that the timing of which is or is not dependent upon food intake. Thus, for example, the agent can be taken every morning and/or every evening, regardless of when the subject has eaten or will eat.

In addition to being used as a monotherapy, the agents described herein can also find use in combination therapies. Effective combination therapy can be achieved with a single composition that includes both an Sp transcription factor agent and a second therapeutic agent, or with two distinct compositions, at the same time, wherein one composition includes the Sp transcription factor agent according, and the other includes the second therapeutic agent(s). Alternatively, the therapy can precede or follow the other agent treatment by intervals ranging from minutes to months. Administration of the compounds of the present invention to a patient will follow general protocols for the administration of pharmaceuticals, taking into account the toxicity, if any, of either agent. It is expected that the treatment cycles would be repeated as necessary. For the treatment or prevention of cancer, Sp transcription factor agents can be combined with one or more of the following: radiation, chemotherapy agents, or vaccine therapies designed to promote an enhanced immune response targeting cancer cells. Further, drugs that downregulate Sp transcription factors decrease "resistance" genes such as survivin and enhance drug- and drug-radiation therapies. See, e.g., *Mol. Cancer. Ther.* 8:533 (2009).

It will be understood that any embodiment, characteristic, element, definition, or general description provided for any aspect of the disclosure can be applied to any other aspect of the disclosure without limitation, unless explicitly stated. Thus, any embodiment discussed herein can be implemented with respect to any method, agent, or composition of the invention, and vice versa. Furthermore, agents and compositions of the invention can be used to achieve methods of the invention.

The use of the word "a" or "an," when used in conjunction with the term "comprising" herein can mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

As an alternative to or in addition to "comprising," any embodiment herein can recite "consisting of:" The transitional phrase "consisting of" excludes any element, step, or ingredient not specified in the claim.

The following is a description of the establishment of HOTAIR as a negative prognostic factor in pancreatic cancer and an analysis of HOTAIR pro-oncogenic activities. This description is based on Kim, K., et al., "HOTAIR Is a Negative Prognostic Factor and Exhibits Pro-Oncogenic Activity in Pancreatic Cancer," *Oncogene* (epub can 2012), which is incorporated herein by reference in its entirety.

Introduction:

Studies on the human, mouse and other genomes have demonstrated that a large number of genes and their corresponding RNAs are non-coding RNAs (ncRNAs) that are differentially expressed in various organs and tissues. The functions of some ncRNAs have been characterized and it is evident that they are the key factors in gene regulation and influence normal and cancer cell phenotypes. Among the different classes of ncRNAs, microRNAs have been the most extensively investigated, and it is estimated that 41000 microRNAs regulate up to 30% of all protein-encoding genes. Several microRNAs are overexpressed in different tumors and their functional pro-oncogenic activity is usually associated with induction of oncogenes or inhibition of multiple genes with tumor suppressor-like activity.

Rinn and coworkers have identified up to 3000 human long intervening non-coding RNAs (lncRNAs), (Rinn, J. L., et al., "Functional Demarcation of Active and Silent Chromatin Domains in Human HOX Loci by Noncoding RNAs," *Cell* 129:1311-1323, 2007; Khalil, A. M., et al., "Many Human Large Intergenic Noncoding RNAs Associate With Chromatin-Modifying Complexes and Affect Gene Expression," *Proc. Nat'l Acad. Sci. USA* 106:11667-11672, 2009) and biological characterization studies suggest that lncRNAs have important functions in both normal and cancer tissues. There is evidence that many lncRNAs act as scaffolds that regulate molecular (protein, RNA and DNA) interactions required for various signaling networks and this is accomplished, in part, by association with chromatin-modifying complexes. HOTAIR is a 2158-bp lncRNA localized to a boundary in the HOXC gene cluster. HOTAIR is a negative prognostic factor for breast, colon and liver cancer patient survival, and increased HOTAIR expression in patients has been correlated with enhanced breast and colon cancer metastasis. HOTAIR expression has been linked to increased breast, liver and colon cancer cell invasiveness, whereas RNA interference (RNAi) studies in liver cancer cells showed that HOTAIR alone had minimal effects alone on cell viability or apoptosis but enhanced the activities of other agents. The activity of HOTAIR is due, in part, to interaction of HOTAIR with the Polycomb Repressive Complex 2 (PRC2) (EZH2, SUZ12 and EED), which enhances H3K27 trimethylation to decrease expression of multiple genes. Other lncRNAs also associate with PRC2 and other chromatin complexes, suggesting potential gene-repressive activity similar to that described for HOTAIR.

In this study, data-mining studies of publicly available databases showed that HOTAIR was overexpressed in pancreatic tumors compared with the normal pancreas and was more highly expressed in advanced tumors. HOTAIR exhibited variable expression in pancreatic cancer cells, and knockdown of HOTAIR in Panc1 and L3.6pL pancreatic cancer cells by RNAi showed that HOTAIR was associated with enhanced cell invasion, cell proliferation, modulation of cell cycle progression and induction of apoptosis. HOTAIR knockdown in L3.6pL cells also inhibited tumor growth in a mouse xenograft model. Knockdown of HOTAIR in Panc1 cells resulted in significant (>1.5) changes in expression of 1006 genes and analysis of the data suggested that HOTAIR mediated gene regulation has a critical role in pancreatic cancer progression and will be a novel epigenetic molecular target for treating pancreatic cancer patients.

Methods and Materials:

Cell lines: Human pancreatic cancer cell lines Panc1, MiaPaCa2 and Panc28 were obtained from American Type Culture Collection (Manassas, Va.). L3.6 pl pancreatic cancer cell line was kindly provided from Dr. I. J. Fidler in M.D. Anderson Cancer Center (Houston, Tex.). The cancer cell lines were grown and maintained in Dulbecco's modified Eagle's medium (DMEM) nutrient mixture (Hyclone, Logan, Utah) supplemented with 0.22% sodium bicarbonate, 0.011% sodium pyruvate, 10% fetal bovine serum (FBS), and 10 ml/l 100× antibiotic antimycotic solution (Sigma Aldrich, St. Louis, Mo.).

Gene set enrichment analysis (GSEA): Pancreatic cancer patient gene profiling data (GSE20501) was obtained from Gene Expression Omnibus (GEO) site. The patients are classified into two groups according to their HOTAIR expression level (top 15%: high vs. bottom 85%: low) and GSEA was carried out to assess the effects of HOTAIR expression level on various biological pathways using these two classified data sets. Similarly, GSEA was also performed using gene profiling data sets obtained from control siRNA control vs. HOTAIR siRNA (siHOTAIR I) transfected Panc1 cells. Significantly enriched biological pathways were identified, which produced nominal p-value <0.05 and false discovery rates (FDR)<0.25.

RNA isolation and quantitative PCR: Total RNA was extracted either from pancreatic cancer cell lines or from tissue samples. Five control and siRNA HOTAIR-transfected tissue samples were analyzed, respectively, from xenograft study using mirVana RNA isolation kit from Ambion (Austin, Tex., USA), and quantitative PCR was carried out using iCycler IQTM real-time PCR detection system (Bio-Rad, Hercules, Calif., USA) after reverse transcription to cDNAs. The RT primer sets for HOTAIR, PCDHB5, PCDH10, JAM2, LAMB3, ABL2, SNA1 and LAMC2 were used as described previously (Gupta, R. A., et al., "Long Non-Coding RNA HOTAIR Reprograms Chromatin State to Promote Cancer Metastasis," *Nature* 464:1071-1076, 2010). The forward and reverse oligonucleotide primer sequences specifically for HOTAIR amplification and detection are also set forth herein as SEQ ID NOS:1 and 2, respectively. All other primer sets and sequences for this assay are shown in TABLE 1.

TABLE 1

Primer set sequences for quantitative RT-PCR analysis

| Primer Set | Forward | Reverse |
|---|---|---|
| GDF15 | GGGCAAGAACTCAGGACGG (SEQ ID NO: 24) | TCTGGAGTCTTCGGAGTGCAA (SEQ ID NO: 25) |
| IL-29 | TATGTGGCCGATGGGAACCT (SEQ ID NO: 26) | AGGGTGGGTTGACGTTCTCA (SEQ ID NO: 27) |
| OAS-1 | TGTCCAAGGTGGTAAAGGGTG (SEQ ID NO: 28) | CCGGCGATTTAACTGATCCTG (SEQ ID NO: 29) |
| MX1 | GTTTCCGAAGTGGACATCGCA (SEQ ID NO: 30) | CCATTCAGTAATAGAGGGTGGGA (SEQ) ID NO: 31) |
| IFTM1 | TCGCCTACTCCGTGAAGTCT (SEQ ID NO: 32) | ATGAGGATGCCCAGAATCAG (SEQ ID NO: 33) |
| IL28A | CACCCTGCACCATATCCTCT (SEQ ID NO: 34) | CACTGGCAACACAATTCAGG (SEQ ID NO: 35) |
| IL28B | CTGCTGAAGGACTGCAAGTG (SEQ ID NO: 36) | GAGGATATGGTGCAGGGTGT (SEQ ID NO: 37) |

siRNA transfection and luciferase assay: Pancreatic cancer cells were transfected with 100 nM of control siRNA or HOTAIR siRNA I (available from Sigma Aldrich, catalogue No. SASI_Hs02__00380445) or HOTAIR siRNA II (available from Sigma Aldrich, catalogue No. SASI_Hs02__00380446) using Lipofectamine 2000 (Invitrogen, Grand Island, N.Y., USA). Panc1 cells were cotransfected with control siRNA or HOTAIR siRNA I and HOTAIR II, and various length of GDF15 luciferase constructs. Luciferase activities were measured after 24 h as described previously. MISSION siRNAs for EZH2 and Suz12 were also purchased from Sigma Aldrich.

Chromatin immunoprecipitation assay: Antibodies for RNA polymerase, EZH2 and Histone H3 trimethyl Lys 27 antibodies were obtained from Active Motif (Carlsbad, Calif., USA), and ChIP assay was performed as described previously. The ChIP primer sequences (forward) 5'-GGAGCACCCTGCTTAGACTG-3' (set forth herein as SEQ ID NO:38) and (reverse) 5'-GGGCCTCAGTATCCTCTTCC-3' (set forth herein as SEQ ID NO:39) were used to amplify the 5' promoter region (−680 to −190) of the GDF 15 gene.

Boyden chamber cell invasion and apoptosis assays: Pancreatic cancer cells were transfected with either siRNAs (HOTAIR vs. control) or expression vectors (empty vs. HOTAIR) and cell invasion assay was performed as described previously. Cells were transfected with siCT or siHOTAIR and after 72 h, cells were stained for Annexin V using the Vibrant apoptosis assay kit as described.

Cell proliferation and fluorescence-activated cell sorting analysis and apoptosis: Cells were seeded in 12-well plates and transfected with either appropriate siRNA or expression vectors, and cell numbers were counted at the indicated times using a Coulter Z1 cell counter (Beckman Coulter, Fullerton, Calif., USA). For fluorescence-activated cell sorting analysis, after pancreatic cancer cells were transfected with siRNAs for either control or HOTAIR, cells were stained with propidium iodide solution and were analyzed on a FACS Calibur Flow Cytometer (Becton Dickinsin Systems, Franklin Lakes, N.J., USA).

Xenograft study: L3.6pL cells ($6\times10^4$ ml) were transfected with 100 nM siHOTAIR or siCT using Lipofectamine. After 48 h cells were collected and $1\times10^6$ cells injected into either side of the flank area of female nude mice (Harlan), and tumor volumes and weights were determined in mice from the siHOTAIR (six mice) or siCT (six mice) groups as described, and siHOTAIR levels were determined by realtime PCR. Tumor volumes were measured ($0.5\times\text{length}\times\text{width}^2$) and after 16 days, the mice were killed and tumor weights were measured and also used for further analysis as described.

Immunohistochemistry and TUNEL assay: Tissue sections were deparaffinized in xylene and treated with graded series of alcohol and rehydrated in PBS. Antigen retrieval was done using 10 mM sodium citrate (pH 6.0-6.2) and endogenous peroxidase was blocked by 3% hydrogen peroxide in methanol for 6 min. Slides were then incubated with blocking serum (Vecstatin ABC Elite kit, Vector Laboratories, Burlingame, Calif., USA) for 45 min. Samples were then incubated overnight with Ki-67 and PCNA antibodies at 4° C. Sections were then washed in PBST and then incubated with biotinylated secondary antibody followed by streptavidin. The brown staining specific for antibody binding was developed by exposing the avidin and biotinylated peroxidase complex to diaminobenzidine reagent (Vector Laboratories) and sections were then counterstained with hematoxylin (Vector Laboratories). The in situ cell death detection POD kit was used for the TUNEL assay according to the instructions in the protocol for tissue sections.

Statistical analysis: Statistical significance of differences between different groups was determined using Student's t-test. Gene profiling data were analyzed either by BRB-Array Tools44 or by Gene Pattern software. Cluster and Treeview programs were employed for generation of heat maps and for gene clustering. Kaplan-Meier analysis and log-rank test were applied to evaluate the prognostic significance of HOTAIR expression level in terms of patient survival. Cox proportional hazard regression model was also used to evaluate independent prognostic factors correlated with tumor stage and lymph node metastasis.

Figure 1B:
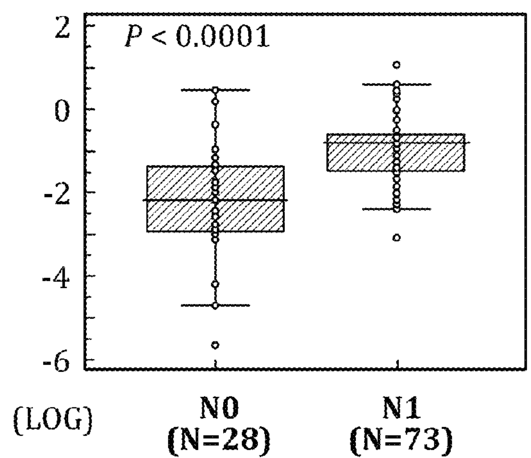
Figure 1C:
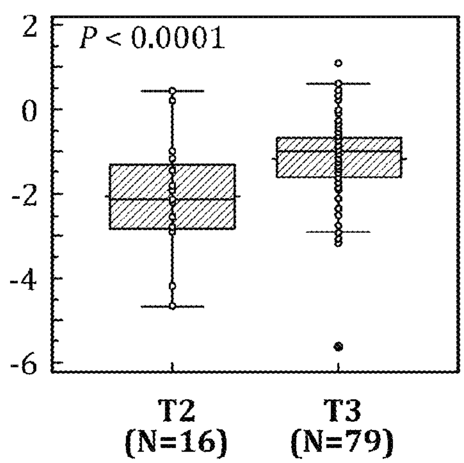
Figure 1D:
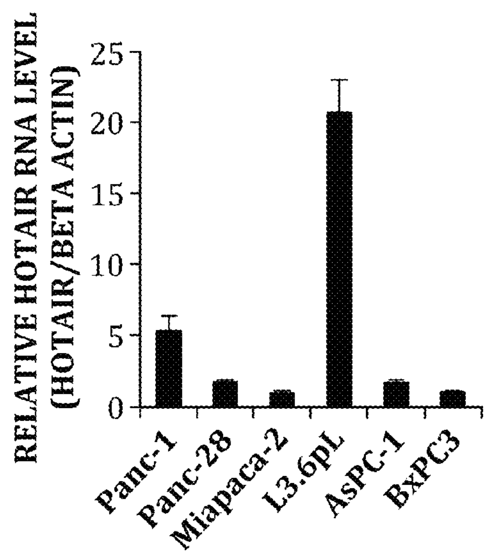

Results:

New data mining analyses of gene profiling databases (Stratford, J. K., et al., "A Six-Gene Signature Predicts Survival of Patients With Localized Pancreatic Ductal Adenocarcinoma," *PLoS Med.* 7:e1000307, 2010; Badea, L., et al., "Combined Gene Expression Analysis of Whole-Tissue and Microdissected Pancreatic Ductal Adenocarcinoma Identifies Genes Specifically Overexpressed in Tumor Epithelia," *Hepatogastroenterology* 55:2016-27, 2008; Collisson, E. A., et al., "Subtypes of Pancreatic Ductal Adenocarcinoma and Their Differing Responses to Therapy," *Nat. Med* 17:500-503, 2011) showed that among 36 pancreatic cancer patients, HOTAIR was more highly expressed in pancreatic tumors compared to non-tumor tissue (FIG. 1A). Additionally, HOTAIR was more highly expressed in tumors spread to regional lymph nodes (N1) compared to tumors localized only in the pancreas (NO) (FIG. 1B). HOTAIR was also more highly expressed in tumors extending beyond the pancreas (T3) compared to tumors only detected in the pancreas (T2) (FIG. 1C). Kaplan-Meier survival analyses also demonstrated that patients with low HOTAIR expression (bottom 85%) had significantly increased overall survival compared to patients with high HOTAIR expression (top 15%). Furthermore, the results of Cox proportional hazard regression analyses consistently indicated that HOTAIR levels and N stage are strongly correlated with overall patient survival ($p<0.05$). Gene set enrichment analyses (GSEA) using pancreatic patient gene profiling data (GSE21501) demonstrated that gene set differences in HOTAIR high vs. low patients indicated that HOTAIR regulates gene sets mainly associated with cell proliferation and cell cycle progression (not shown). These results demonstrate that HOTAIR is involved in mechanisms underlying the progression of the disease and is a negative prognostic factor for pancreatic cancer. FIG. 1C illustrates relative HOTAIR RNA levels in various pancreatic cancer cell lines, adjusted for GAPDH. These expression data demonstrate that HOTAIR was highly expressed in Panc1 and L3.6pL cells, whereas lower expression was observed in Panc-28, MiaPaca-2 and AsPC-1, and BxPC3 cells. These results were consistent with data mining from array data from several pancreatic cancer cell lines, which also showed that HOTAIR was overexpressed in Panc1 cells (not shown).

Panc1 cells are a highly aggressive 'basal-like' pancreatic cancer cell line, and knockdown of HOTAIR by RNAi (siHOTAIR) resulted in changes in expression (41.5-fold) of 1006 genes, in which expression of 454 genes was enhanced and expression of 552 genes was decreased (not shown). HOTAIR knockdown was performed using two different siRNAs (siHOTAIR I and siHOTAIR II, see SEQ ID NOS:22 and 23, respectively) to avoid off-target effects, each exhibiting effective and specific knockdown of HOTAIR. Results from GSEA using gene ontology terms showed that 20 significant gene sets were affected by HOTAIR knockdown in Panc1 cells compared with control (siCT) cells. As 10 out of the 20 gene ontology terms were related to the cell cycle, it was concluded that HOTAIR regulation of cell viability and cell cycle progression was important in both cultivated pancreatic cancer cells and patients.

Previous studies characterized HOTAIR-regulated genes by overexpression of this ncRNA in MDA-MB-231 breast cancer cells. There were 241 common genes among 1006 and 9260 genes (>1.5-fold change) modulated by HOTAIR knockdown or overexpression in Panc1 and MDA-MB-231 cancer cells, respectively. As the HOTAIR-regulated genes were determined by opposite procedures (knockdown vs.

overexpression) in Panc1 and MDA-MB-231 cells, respectively, heat maps of the genes induced or repressed by HOTAIR knockdown or overexpression in both cell lines were compared. The heat map illustrates the limited overlap between the 241 genes regulated by HOTAIR in Panc1 and MDA-MB-231 cells, and this is further evidenced that among the 119 genes induced in Panc1 cells by siHOTAIR II, only 27 genes were repressed in MDA-MB-231 cells by HOTAIR overexpression, whereas among the 122 genes repressed after HOTAIR KO in Panc1 cells only 24 genes were induced (not shown). Moreover, siHOTAIR resulted in the repression of 122 genes in Panc1 cells, and only 18 of these genes were induced by HOTAIR overexpression in MDA-MB-231 cells. Thus, HOTAIR has an important role in PRC2-mediated gene suppression. Comparison of HOTAIR-regulated genes in Panc1 cells with HOTAIR/PRC2-coregulated genes in MDA-MB-231 (in a chromatin immunoprecipitation assay (ChIP) assay), indicated only nine genes in common but only minimal overlap between PRC2-regulated genes induced by siHOTAIR in Panc1 cells and genes suppressed by HOTAIR overexpression in MDA-MB-231 cells. The differences in HOTAIR-regulated genes in Panc1 and MDA-MB-231 cells were further investigated by comparing specific genes repressed and induced by HOTAIR overexpression in the latter cell line. Among three genes repressed by HOTAIR overexpression in MDA-MB-231 cells (PCDHB5, PCDH10 and JAM2), two were enhanced after HOTAIR knockdown in Panc1 and L3.6pL cells, but only JAM2 expression was enhanced in both cell lines (not shown). LAMB3, ABL2, SNA1 and LAMC2 were induced by HOTAIR overexpression in MDA-MB-231 cells; however, none of these genes were repressed by siHOTAIR in either Panc1 or L3.6pL cells (FIG. 2D), and two of the four genes (ABL2 and SNA1) were induced in both cell lines. These results confirm that HOTAIR regulates significantly different sets of genes in pancreatic vs. breast cancer cells.

HOTAIR knockdown induces or represses multiple genes that could contribute to the functional pro-oncogenic activity of HOTAIR in Panc1 cells. Expression of seven genes with tumor suppressor-like activity that are constitutively suppressed by HOTAIR and induced in Panc1 cells were examined after transfection with siHOTAIR. siHOTAIR I significantly induced expression of GDF15, IL29, IL28A, IL28B, IFTM1, OAS1, and MX1 mRNA in Panc1 and L3.6pL cells. The role of the PRC2 complex in coregulating suppression of these HOTAIR-suppressed genes was investigated by EZH2 knockdown (siEZH2), and only GDF15 mRNA expression was induced in Panc1 and L3.6pL cells transfected with siEZH2. Similar results were observed for knockdown of Suz12, another member of the PRC2 complex. GDF15 is a growth-inhibitory/proapoptotic gene, and ChIP analysis demonstrates that primers directed at the proximal region of the GDF15 promoter detected H3K27 trimethylation and EZH2 binding but not RNA pol II interactions in Panc1 cells transfected with siCT (control). In contrast, knockdown of HOTAIR resulted in the loss of H3K27 trimethylation and EZH2 binding but increased interaction of RNA pol II with the promoter region, and this is consistent with cooperative PRC2/HOTAIR induction of GDF15. The effects of HOTAIR on GDF15 were further evaluated using two different siRNAs for HOTAIR in order to minimize possible off-target effects; both siHOTAIR I and II exhibited a similar level of knockdown efficiency. Both siRNAs for HOTAIR decreased luciferase activity in Panc1 cells transfected with constructs containing the proximal −3500 to +41, −1086 to +41 and −474 to +41 regions of the GDF15 promoter, whereas the effects of siHOTAIR were minimal in Panc1 cells transfected with a construct containing only the −133 to +41 region of the promoter. These results suggest that HOTAIR/PRC2 coordinately regulate GDF15 in pancreatic cancer cells; in contrast, this gene was not affected by HOTAIR overexpression in MDA-MB-231 cells, further demonstrating cell context-dependent differences in HOTAIR/PRC2-regulated genes.

As MiaPaCa2 and Panc28 cells express relatively low levels of HOTAIR, the functional and genomic effects of HOTAIR overexpression were investigated and compared with overexpression of HOTAIR as previously reported in MDA-MB-231 cells and knockdown of HOTAIR in Panc1 and L3.6pL cells. HOTAIR overexpression enhanced MiaPaCa2 and Panc28 cell invasion in a Boyden chamber assay, and this was consistent with previous functional studies in breast and colon cancer cells. HOTAIR overexpression decreased PCDBH5 and PCDH10 (as observed in MDA-MB-31 cells) but not JAM2 in MiaPaCa2 cells, whereas in Panc28 cells PCDH10 and JAM2 were induced and PCDBH5 was unchanged by HOTAIR overexpression. In contrast, overexpression of HOTAIR either decreased or did not affect LAMB3, ABL2, SNA1 or LAMC2 mRNA levels in MiaPaCa2 and Panc28 cells, whereas these genes were all induced by HOTAIR overexpression in MDAMB-231 cells. The HOTAIR-repressed genes were also investigated by overexpression of HOTAIR in MiaPaCa2 and Panc28 cells. HOTAIR downregulated GDF15, MX1, IL28, IL28A, IL28B and IL29 only in MiaPaCa2 cells and the remaining genes were unchanged in both cell lines. Overexpression of HOTAIR in MiaPaCa2 and Panc28 cells increased cell proliferation and the % of cells in S phase and decreased the % of G2/M (in Panc28 but not in MiaPaCa2 cells). Thus, results of both HOTAIR knockdown and overexpression in pancreatic cancer cells further demonstrate differences between HOTAIR-regulated genes in pancreatic cells and breast cancer cells, and also show differences in HOTAIR function in MiaPaCa2 and Panc28 cells that express low levels of this ncRNA.

Figure 2A:
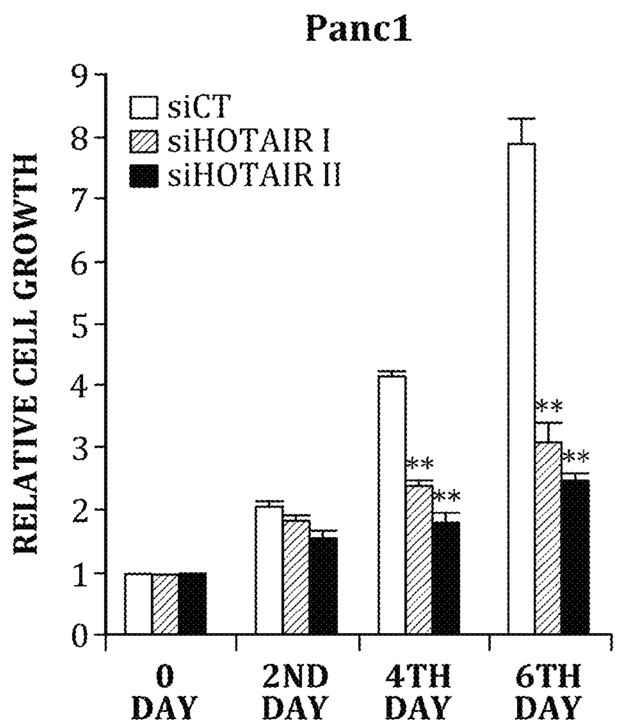
FIGS. 2A-2D illustrate HOTAIR regulation of cancer cell growth as determined by RNAi knockdown of HOTAIR using two different siRNAs. Transfection of siHOTAIR oligonucleotides inhibits growth of Panc1 cells (FIG. 2A) and L3.6pL (FIG. 2B) pancreatic cells over 6 days. Transfection of siHOTAIR oligonucleotides also inhibit expression of cyclin D1 and cyclin E, as determined by reduced mRNA levels in Panc1 cells (FIG. 2C) and L3.6pL (FIG. 2D). ** indicates decrease with significance of $p<0.05$.
Figure 2B:
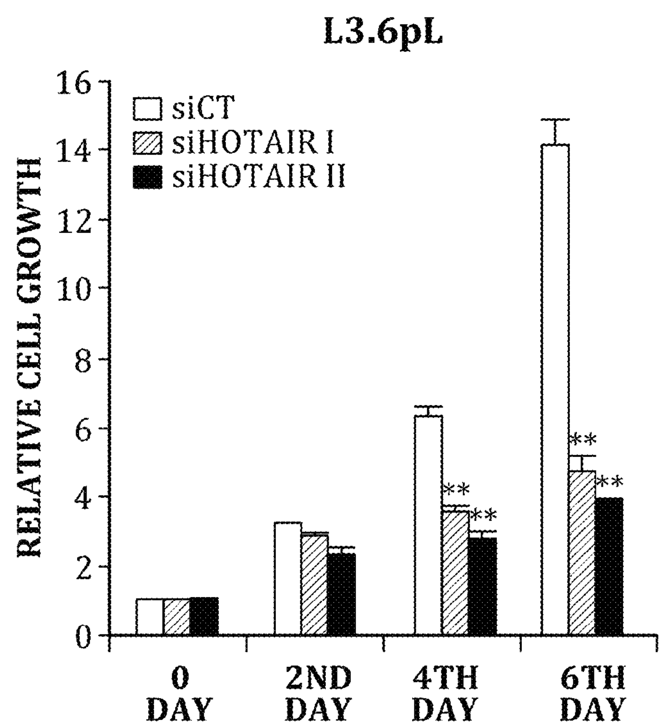
Figure 2C:
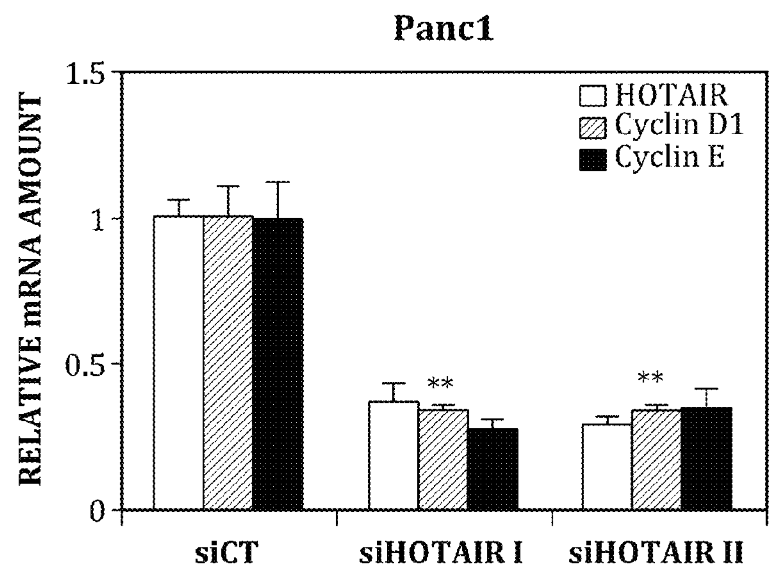
Figure 2D:
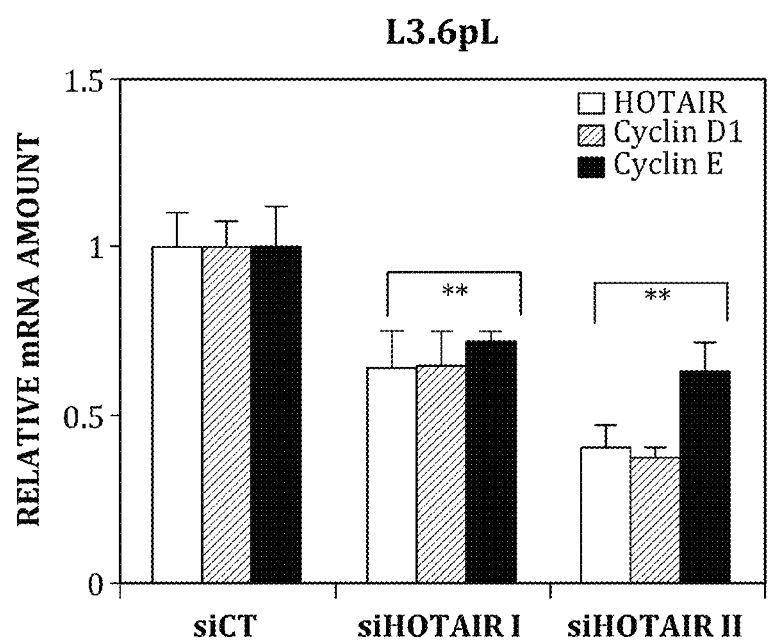
Figure 3A:
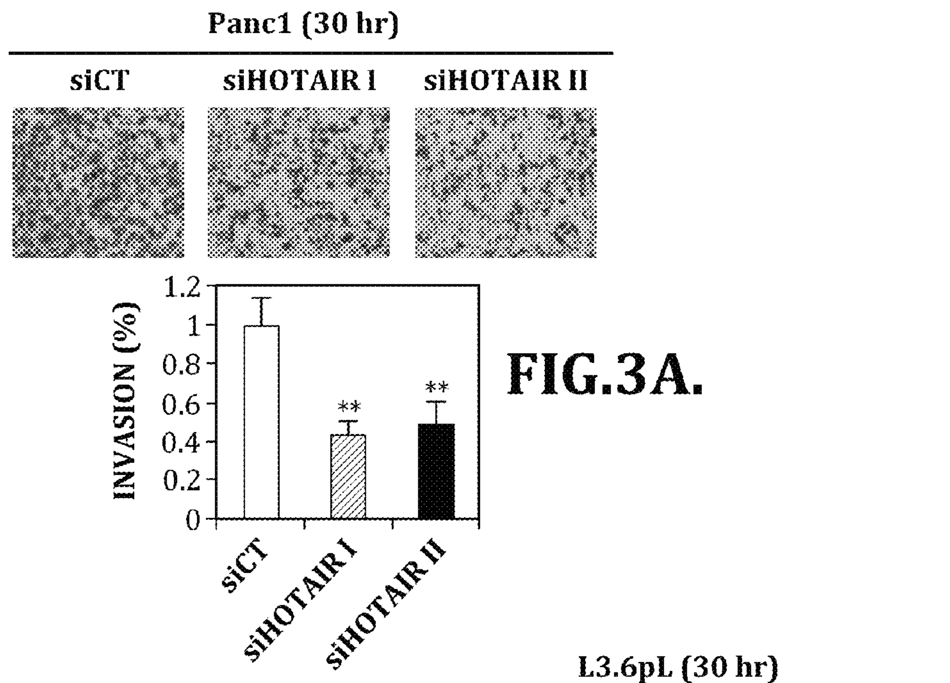
FIGS. 3A-3C illustrate the effects of HOTAIR on cancer cell invasion. Panc1 (FIG. 3A) and L3.6pL (FIG. 3B) cells were transfected with siHOTAIR (I and II, separately) and after 30 hours, cell invasion was determined in a Boyden chamber assay ( inhibition, $p<0.05$). Apoptosis was determined by measuring enhanced Annexin V staining (FIG. 3**C) (* induction, $p>0.05$).
Figure 3B:
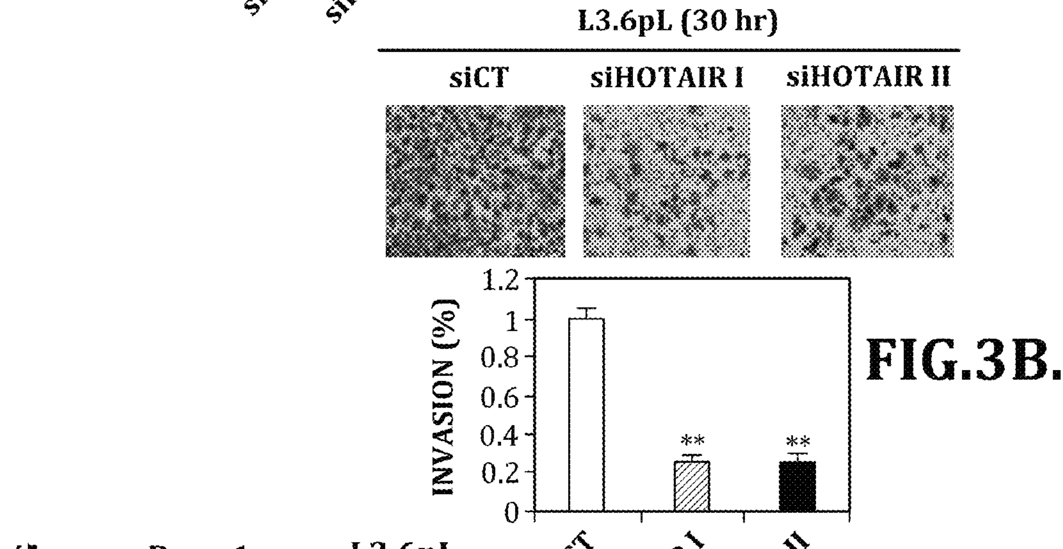
Figure 3C:
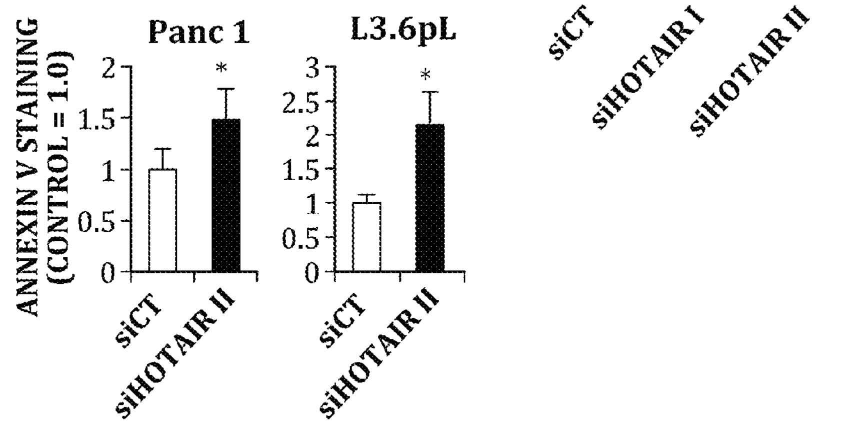

The functional effects of siHOTAIR in Panc1 and L3.6pL cells that overexpressed this ncRNA were further investigated. Transfection of siHOTAIR I and II inhibited Panc1 and L3.6pL growth, which was significant after 4 days, and 450% growth inhibition was observed after 6 days (FIGS. 2A and 2B). Moreover, the siHOTAIR I and II oligonucleotides also caused a measurable decreased expression of two representative growth promoting genes (cyclin D1 and cyclin E), demonstrating a role for HOTAIR in expression (upregulation) of these genes in parts of the cell cycle (FIGS. 2C and 2D). Further, siHOTAIRs caused a G0/G1- to S-phase arrest in Panc1 cells (32 h), whereas in L3.6pL cells there was a decrease in the percent of cells in G0/G1 and increase in G2/M, indicating pancreatic cancer cell context-dependent differences in the effects of HOTAIR on cell cycle progression (not shown). siHOTAIRs significantly decreased Panc1 and L3.6pL invasion using a Boyden chamber assay (FIGS. 3A and 3B, respectively); siHOTAIR II also enhanced Annexin V staining associated with induction of apoptosis in Panc1 and L3.6pL cells (FIG. 3C), and siHOTAIR also induced PARP cleavage in both cell lines (data not shown). L3.6pL cells transfected with siHOTAIR II were used in a mouse xenograft model, and up to 16 days after knockdown of HOTAIR by RNAi there was a dramatic decrease in pancreatic tumor volume (FIG. 4A) and weight (FIG. 4B), and HOTAIR expression (FIG. 4C). Immunohistochemical staining of tumor tissue indicated an increase in terminal deoxyribonucleotide transferase-mediated nick-end labeling (TUNEL) staining and a decrease in proliferation markers (Ki67 and PCNA) in siHOTAIR vs. siCT-transfected tumors.

These in vivo data complement the functional in vitro studies of HOTAIR and confirm the pro-oncogenic activity of this lncRNA in pancreatic cancer cells and tumors.

Discussion:

HOTAIR was initially identified as one of the 231 ncRNAs associated with human HOX loci, and HOTAIR resided in the HOXC locus but repressed transcription in the more distal HOXD locus in foreskin fibroblasts. HOTAIR interacted with the PRC2 complex and was required for PRC2-dependent histone H3 lysine 27 trimethylation and gene silencing. HOTAIRM1 and HOTTIP are lncRNAs associated with the HOXA locus. See Zhang et al. *Blood* 113(11):2526-34 (March 2009), and Wang et al. *Nature* 472:120-124 (2011), respectively. Both of these lncRNAs differentially modulate gene expression in various cell and tissue types, but genes/pathways modulated by these lncRNAs are PRC2-independent.

HOTAIR has also been characterized as a negative prognostic factor in breast, liver and colon cancer patients, and the results of this study demonstrate that HOTAIR is also over-expressed in human pancreatic tumors compared with non-tumor tissue (FIGS. 1A through 1C). Moreover, there is also evidence that HOTAIR is more highly expressed in more aggressive and invasive pancreatic tumors (FIGS. 1A through 1C). HOTAIR function was investigated in knockdown studies and indicates that this ncRNA enhances pancreatic cancer cell invasion, inhibits cell growth, modulates cell cycle progression and induces apoptosis in vitro, and HOTAIR knockdown in L3.6pL cells inhibited tumor growth in athymic nude mice bearing these cells as xenografts (FIGS. 4A-4C). The results of HOTAIR overexpression in MiaCaPa2 cells and Panc28 cells were also consistent with the pro-oncogenic activity of HOTAIR, although there were some cell context-dependent differences. Thus, HOTAIR not only has a role in invasion of pancreatic, breast, colon and liver cancer cells, but also exerts distinct pro-oncogenic activities in pancreatic cancer associated with increased cell survival and proliferation, and repression of interferon-related genes. This was further supported by a similar result from GSEA analysis of Panc1 cells and human tumors, demonstrating that at least 50% of the gene sets were associated with cell cycle progression and proliferation.

Modulation of HOTAIR expression in breast and colon cancer cells, and tumors results in both enhanced and suppressed expression of genes, and a subset of genes repressed by HOTAIR in these cancer cells were also coregulated by PRC2. A comparison of the gene expression data modulated by HOTAIR overexpression in MDA-MB-231 cells and HOTAIR knockdown in Panc1 cells showed some overlap in expression of individual genes; however, a heat map of induced/repressed genes illustrates significant differences between the cell lines. Moreover, only nine of the 854 genes coregulated by HOTAIR/PRC2 in MDA-MB-231 cells were also affected by HOTAIR knockdown in Panc1 cells. Among these genes, only OC1AD2 and RSAD2 were induced in Panc1 cells, whereas only minimal repression was observed after HOTAIR overexpression in MDA-MB-231 cells.

HOTAIR-dependent gene regulation in pancreatic cancer cells was investigated here by HOTAIR knockdown in Panc1 and L3.6pL cells, and HOTAIR overexpression in Panc28 and MiaPaCa2 cells using a set of genes repressed (JAM2, PCDH10 and PCDHB5) and induced (ABL2, SNAIL, LAMB3 and LAMC2) by HOTAIR overexpression in MDA-MB-231 cells. HOTAIR knockdown or overexpression gave variable results among the four different pancreatic cancer cell lines, which in turn exhibited minimal overlap with respect to HOTAIR-dependent regulation of this set of genes in MDA-MB-231 cells. These results were consistent with the differences observed in the gene arrays from Panc1 vs. MDA-MB-231 cells.

A second set of genes identified in the microarray that were significantly induced after HOTAIR knockdown were further investigated in Panc1 and L3.6pL cells transfected with siHOTAIR, and all were induced in both cell lines. Previous studies show that all seven genes exhibit tumor suppressor-like activities, and four genes, namely IL29, IL28A, IL28B and IFTM1, were among a subset of several interferon-regulated genes suppressed by HOTAIR in Panc1 cells. Transfection of Panc1 and L3.6pL cells with siEZH2, a key component of the PRC2 complex, or siSuz12, another PRC2 component, showed that only GDF15 was coregulated by HOTAIR and EZH2 (PRC2), and ChIP assays in cells transfected with siCT vs. siHOTAIR confirmed that GDF15 was a HOTAIR/PRC2-regulated gene. In contrast, the interferon-related genes were not affected by EZH2 knockdown and the mechanisms of PRC2-independent but HOTAIR-mediated suppression of these genes are currently being investigated. These observations are consistent with recent reports showing that HOTAIR regulation of multiple genes is EZH2-independent. Consistent results were observed for the HOTAIR-regulated gene sets in pancreatic cancer patients and after HOTAIR knockdown in pancreatic cancer cells, suggesting that knockdown of endogenous HOTAIR rather than overexpression can be preferable for investigating ncRNA-dependent gene regulation and function.

In summary, it is demonstrated in this description that HOTAIR is a negative prognostic factor for pancreatic cancer patients and exhibits pro-oncogenic activity in both in vitro and in vivo bioassays. HOTAIR-dependent gene regulation in pancreatic cancer cells is complex and differs significantly from a previous report in breast cancer cells. Nevertheless, HOTAIR knockdown in cells overexpressing this ncRNA gave consistent results using a subset of highly regulated genes, suggesting that HOTAIR-mediated suppression of genes in pancreatic cancer is both PRC2-dependent and PRC2-independent. Subsequent studies described herein are focused on the mechanisms associated with suppression and activation of genes by HOTAIR in pancreatic cancer and development of therapeutic strategies that target HOTAIR.

The following is a description of the investigation of the regulation of lncRNA by Specificity Protein Transcription Factors (SpTFs).

Introduction:

The negative prognostic significance and pro-oncogenic activity of HOTAIR in pancreatic cancer is established in the study described above. Specifically, it is demonstrated above that HOTAIR repression of genes was both PRC2-dependent and -independent. However, there was minimal overlap between HOTAIR/PRC2-repressed genes in breast cancer cells vs. HOTAIR-repressed genes in Panc1 pancreatic cancer cells. The anti-apoptotic gene GDF15 was identified as a HOTAIR/PRC2-regulated gene in pancreatic cancer cells by knockdown of HOTAIR and PRC2 components EZH2 and SUZ12, whereas repression of the interferon-inducible protein Mx1 and interleukin-29 (IL-29) was HOTAIR-dependent but PRC-2 independent.

Specificity protein 1 (Sp1) is a transcription factor (TF) that is also overexpressed pancreatic cancer and is a negative prognostic factor for patient survival. Studies by the inventors have shown that Sp1, Sp3, and Sp4 are highly expressed in pancreatic and other cancer cells and these TFs play an important pro-oncogenic role in these cells due to their regulation of Sp-dependent growth promoting (EGFR, c-MET, PTTG-1, cyclin D1), survival (bcl-2 and survivin), angiogenic (VEGF and VEGFR1/R2), and inflammatory (p65) genes. Moreover, knockdown of Sp1 in pancreatic and other cancer cells gives some of the same responses observed using siHOTAIR. See, e.g., FIG. 1D, FIGS. 2A-2D, and FIGS. 3A and 3B. Specificity protein transcription factors (SpTFs) are a prototypical example of "non-oncogene addiction" by cancer cells and their importance as drug targets is due to the differential expression of Sp proteins in cancer (high) vs. non-cancer (low) tissue, and this correlates with their decreased expression in animals and humans with age. The inventors hypothesized that HOTAIR was regulated by an SPTF and that agents that downregulate SpTFs might also downregulate HOTAIR.

Figure 5A:
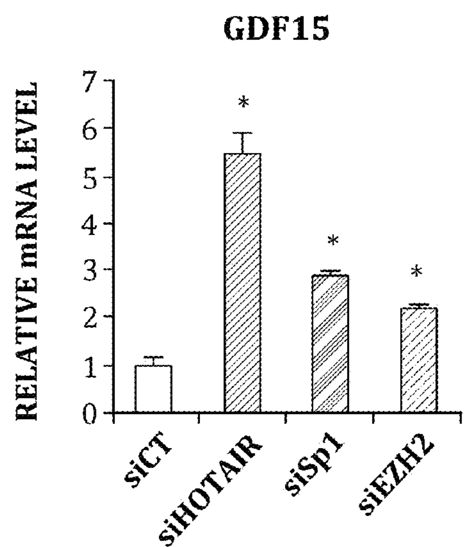
FIGS. 5A-5C illustrate the induction of gene expression for genes in Panc1 cells caused by the RNAi knockdown of HOTAIR, SP1, and EZH2. Panc1 cells were transfected with siCT (control), siHOTAIR, siSP1, and siEZH2 and mRNA expression of GDF15 (PRC-2 dependent) (FIG. 5A) and Mx1 and IL29 (PRC-independent) (FIGS. 5A and 5B) were determined by realtime PCR.
Figure 5B:
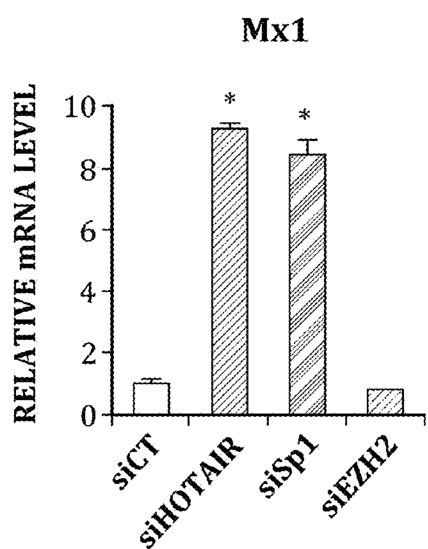
Figure 5C:
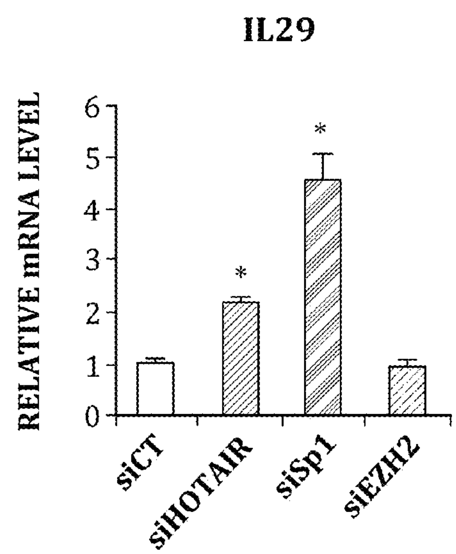

Results and Discussion:

The similar downstream regulatory effects of Sp1 and HOTAIR were characterized to establish a potential connection between Sp1 and HOTAIR. Sp1 knockdown surprisingly revealed that in Panc1 cells transfected with iSp1 oligonucleotide (Sp1-KO) more genes were induced than repressed, suggesting that Sp1, like HOTAIR, was also involved in gene induction. Moreover, it was observed that 377 genes were commonly regulated by HOTAIR and Sp1 (332 repressed, 45 activated). Some of the effects of iSp1 can be due, in part, to decreased expression of HOTAIR. Independent knockdown of both HOTAIR and Sp1 increased expression of GDF15 (PRC2-dependent) and the PRC2-independent Mx1 and IL-29 genes. FIGS. 5A-5C. For the same three genes, a chromatin immunoprecipitation (ChIP) assay demonstrated that knockdown of HOTAIR and Sp1 enhanced POLII binding to their respective gene promoters, and these data were consistent with the enhanced gene expression data (FIGS. 5A-5C). A ChIP assay was also used to determine Sp1 and EZH2 binding to the −1618 to −1267 (GDF15), −527 to −299 (Mx1), and −585 to −205 (IL-29) region of these genes. Because the vast majority of PRC2 bound genomic sequences are localized within 1 kb of a transcription start site, the multiple primer sets were designed for detecting this genomic region of target gene promoters. Results of the ChIP assay confirmed that Sp1 and EZH2 bound to the GDF15 promoter, indicating that Sp1 and possibly other Sp proteins can form part of the PRC-2/HOTAIR complex that is required for gene repression. This is the first demonstration of the novel repressive function of Sp1 in combination with PRC2 and HOTAIR. Furthermore, IL-29 and Mx1 regulation was HOTAIR/Sp1-dependent but PRC-independent, which is also the first demonstration of this novel repressor complex.

Comparable procedures and arrays to determine common HOTAIR-Sp3 and HOTAIR-Sp4 regulated genes. Using knockdown assays, it was observed that 209 genes were commonly regulated by HOTAIR and Sp3 (75 repressed, 134 activated). Similarly, it was observed that 208 genes were commonly regulated by HOTAIR and Sp4 (83 repressed, 124 activated). The results suggested that both Sp3 and Sp4 also cooperatively interacted with HOTAIR to repress genes.

The above results demonstrate that HOTAIR and Sp1 coordinately decrease expression of several "tumor-suppressor-like" genes. Moreover, knockdown of Sp proteins by RNAi gives some of the same responses including inhibition of cell growth, induction of apoptosis and inhibition of migration/invasion. Therefore, it was investigated whether SpTFs also regulate HOTAIR expression in cancer cells.

Figure 6A:
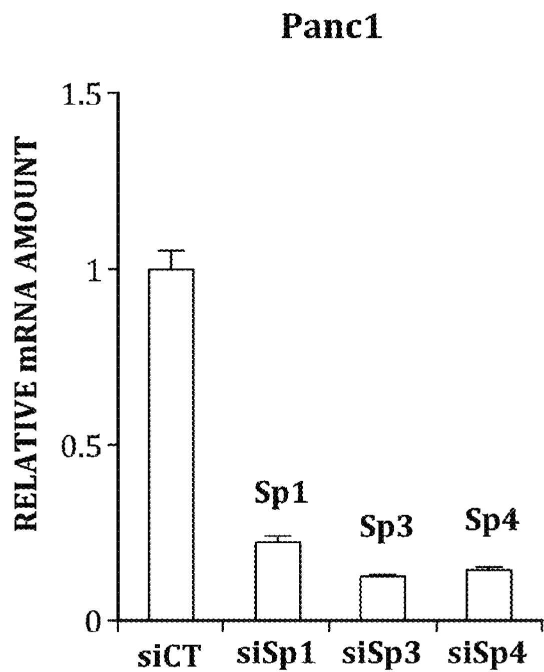
FIGS. 6A and 6B illustrate the knockdown effects of siRNAs for Sp1, Sp3, and Sp4 in Panc1 cells.
Figure 6B:
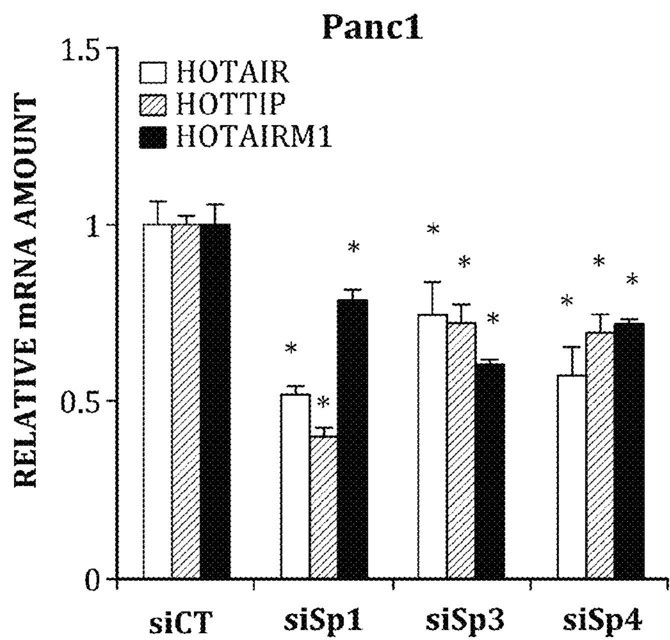

Using short interfering RNAs corresponding to SpTF genes for RNAi assays, expression of the SpTF were successfully knocked down. Sp1 was knocked down using an oligonucleotide with a sequence set forth herein as SEQ ID NO:19. Sp3 was knocked down using an oligonucleotide with a sequence set forth herein as SEQ ID NO:20. Sp4 was knocked down using an oligonucleotide with a sequence set forth herein as SEQ ID NO:21. Results in FIG. 6A show that siSp1, siSp3, and siSp4 decreased Sp1, Sp3, and Sp4 mRNA levels in Panc1 cells compared to siCT (control). Comparable effects were observed for Sp proteins (data not shown). Moreover, the application of siSp1, siSp3 and siSp4 surprisingly resulted in a significant decrease in the expression of HOTAIR and two other HOX region ncRNAs (HOTAIRM1 and HOTTIP). FIG. 6B. In this assay, HOTAIRM was amplified and detected using forward and reverse oligonucleotide sequences set forth herein as SEQ ID NOS:3 and 4, respectively. Additionally, HOTTIP was amplified and detected using forward and reverse oligonucleotide sequences set forth herein as SEQ ID NOS:10 and 11, respectively. Examination of the HOTAIR promoter showed that there are at least two GC-rich Sp binding sites. A ChIP assay using primers that specifically target the GC-rich region (Primer II) and non-GC-rich regions (Primers I and III) showed that Sp1 preferentially bound the GC-rich region (Primer II) (not shown). These results demonstrate for the first time that expression of HOTAIR and other lncRNAs are regulated, at least in part, by SpTFs and opens the possibility that anticancer drugs that downregulate Sp1, Sp3, and Sp4 in cancer cells and tumors will target HOTAIR and other Sp-regulated lncRNAs.

The following is a description of an analysis of compounds targeting HOTAIR through downregulation of SpTFs.

Introduction:

Sp transcription factors (e.g., Sp1, Sp3, and Sp4) are highly expressed in tumor vs. non-tumor tissues. Sp1 is a negative prognostic factor for pancreatic cancer survival, and this correlates with the prognostic significance of HOTAIR, as demonstrated above. The high pro-oncogenic activity of SpTFs coupled with the "addiction" of pancreatic cancers for these TFs makes them ideal drug targets, which is a major focus of the inventors. Drug-induced downregulation of SpTFs in pancreatic and other cancer cell lines is proteasome-dependent (minor) or -independent (major), and the specific pathways are both drug- and cell context-dependent. Compounds that regulate SpTFs were investigated for their effect on HOTAIR expression.

Figure 7A:
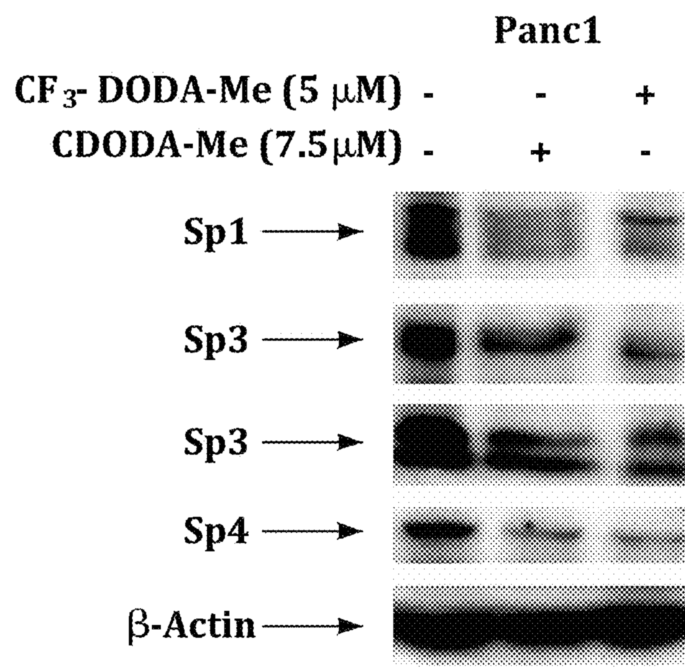
FIGS. 7A and 7B illustrate the effects of CDODA-Me and $CF_3$CDODA on the expression of SpTF proteins (FIG. 7A) and the HOTAIR expression (RNA levels) in Panc1 cells (FIG. 7B). These results were obtained after 24 hrs. Sp proteins were almost non-detectable after 48 hrs. * significant inhibition, $p<0.05$.
Figure 7B:
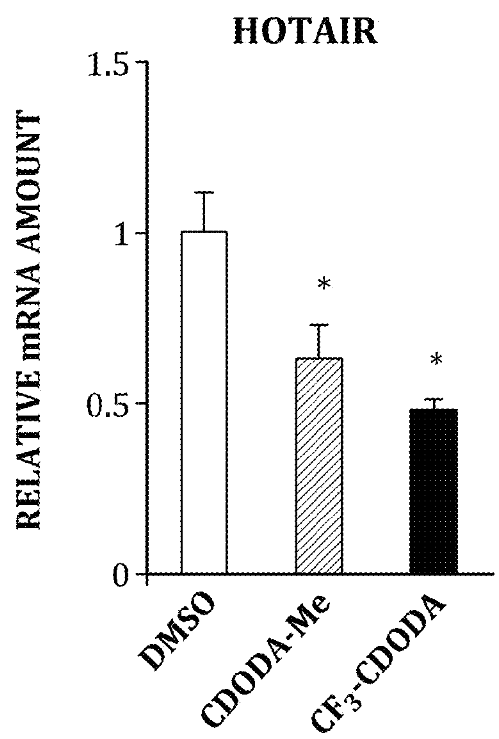

Results and Discussion:

Synthetic triterpenoids CDODA-Me (methyl 2-cyano-3, 11-dioxo-18-olean-1,12-dien-30-oate) and the $CF_3$ analog $CF_3$DODA-Me downregulate Sp1, Sp3, and Sp4 proteins in multiple cancer lines. Previous studies showed that the synthetic triterpenoid CDODA-Me decreased microRNA (miR)-27a and increased ZBTB10, an SpTF repressor in colon cancer cells. Similarly, $CF_3$DODA-Me and CDODA-Me downregulate Sp1, Sp3, and Sp4 proteins in Panc1 cells. FIG. 7A. Similar results were observed other pancreatic cancer cell lines (data not shown). FIG. 7B demonstrates that treatment of CDODA-Me and CF3DODA-Me also decreased HOTAIR expression in Panc1 cells, which represents the first example of drug-induced downregulation of an oncogenic lncRNA. It is noted that HOTAIR was decreased by both the triterpenoids and by Sp knockdown by >50%.

Figure 8A:
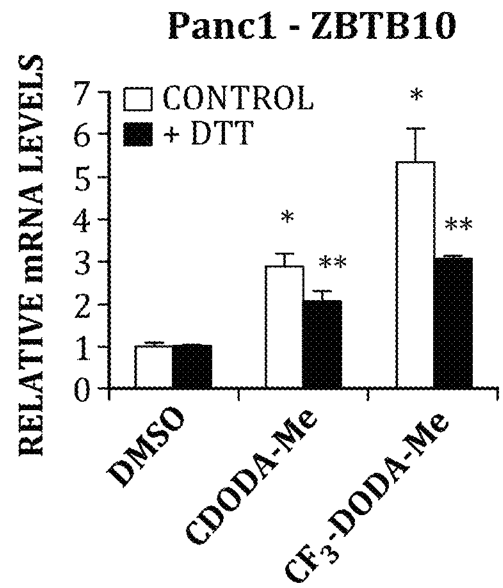
FIGS. 8A-8D illustrate the effects of CDODA-Me and $CF_3$CDODA with or without DDT in Panc1 cells.
Figure 8B:
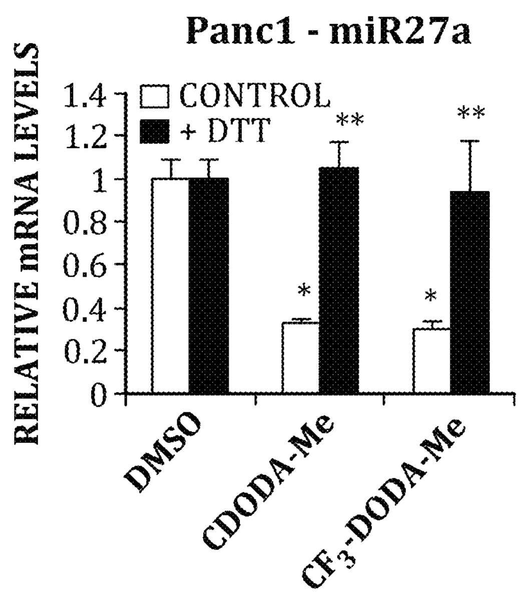
Figure 8C:
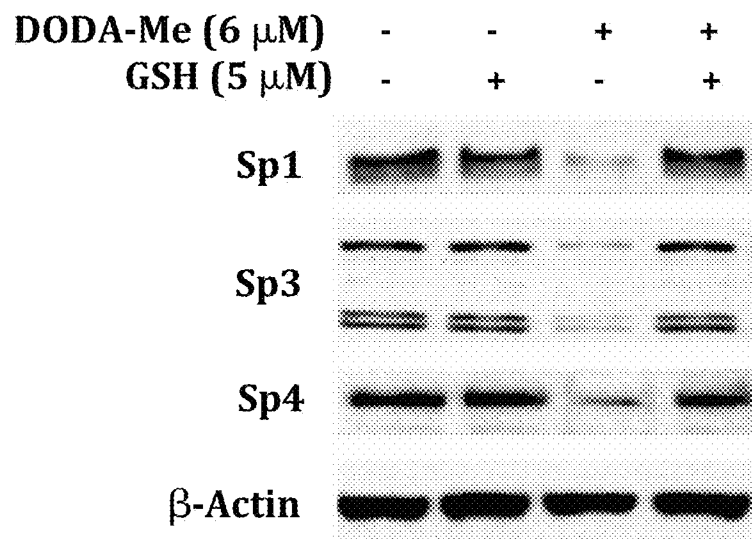
Figure 8D:
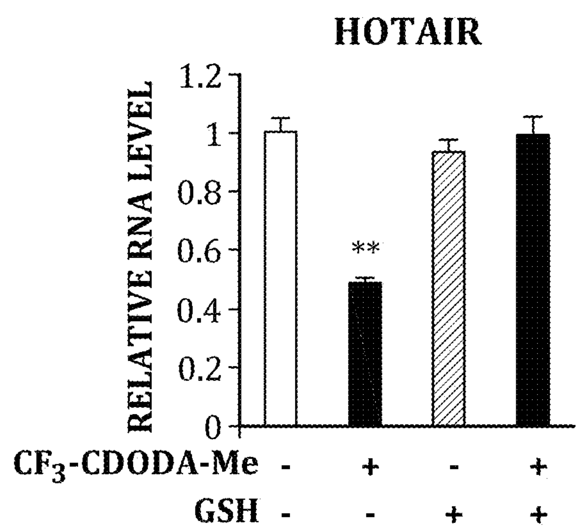

Previous studies with CDODA-Me and the structurally-related triterpenoid analog methyl-2-cyano-3,12-dioxooleana-1,9-dien-28-oate (CDDO-Me) showed that SpTF downregulation in colon and pancreatic cancer cells, respectively, was due to repression of miR-27a and induction of ZBTB10, an Sp transcriptional repressor that is regulated by miR-27a. Moreover, in pancreatic cancer cells, drug-mediated Sp protein and miR-27a downregulation and induction of ZBTB10 was due to induction of reactive oxygen species (ROS), and the process was inhibited by cotreatment with antioxidants such as DTT or GSH. Similar results have been observed for other anticancer agents such as betulinic acid and GT-094 (a NO-NSAID) in colon and celastrol in bladder cancer cells. In this study, the effects of CDODA-Me and $CF_3$DODA-Me on these targets were investigated in Panc1 cells. Results illustrated in FIGS. 8A-8C show that CDODA-Me- and $CF_3$DODA-Me-mediated induction of ZBTB10, downregulation of miR-27a, and repression of Sp1, Sp3, and Sp4 was inhibited after cotreatment with antioxidants DTT or GSH. This suggests that drug-induced ROS can also repress HOTAIR. Further, FIG. 81) shows that $CF_3$DODA-Me-induced repression of HOTAIR is also attenuated by GSH. Moreover, the fact that CDODA-Me decreased Sp1, Sp3, and Sp4 in pancreatic cancer cells (FIG. 8C) demonstrates that agents such as CDODA-Me that downregulate Sp1, Sp3, and Sp4 also decrease HOTAIR, an Sp-regulated gene. Moreover, we have recently demonstrated that miR-20a and miR-17-Sp regulate expression of a second Sp-repressor, ZBTB4, and ROS also disrupts miR-20a/17-5p-ZBTB4, and thus, also likely influence expression of HOTAIR and other pro-oncogenic lncRNAs.

Figure 9A:
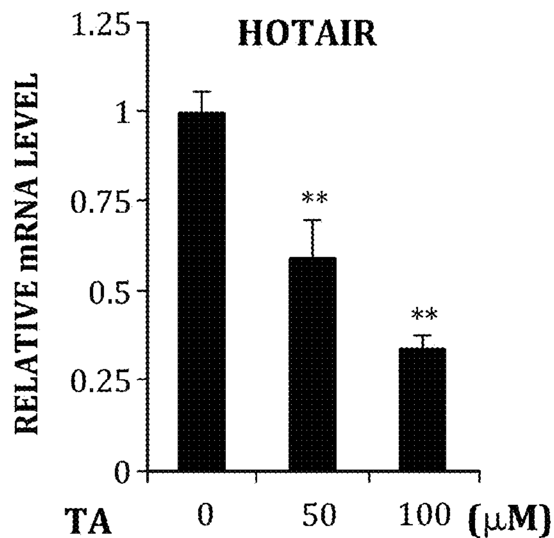
FIGS. 9A-9D illustrate the effects of tolfenamic acid (TA) on regulation in breast cancer cells (MDA-MB-231).
Figure 9B:
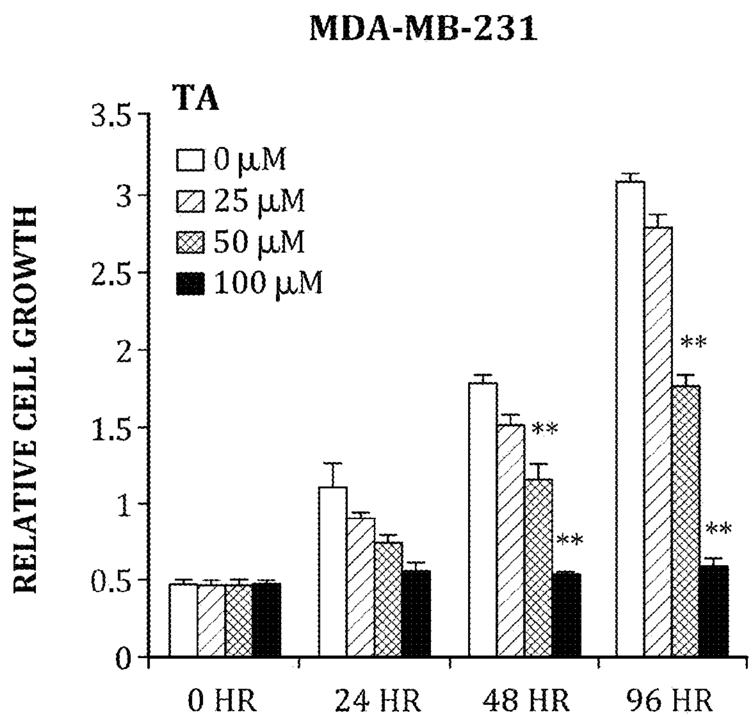
Figure 9C:
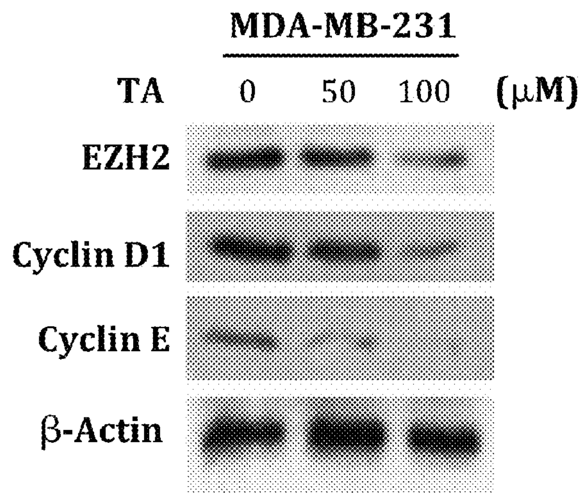

In another instance, tolfenamic acid (TA), an NSAID that also decreases Sp proteins in cancer cells (*J. Nat'l Cancer Inst.* 98:855 (2006); *Cancer Res.* 67:3286 (2007); *Mol. Cancer. Ther.* 8:533 (2009)), decreased HOTAIR, cancer cell growth, and expression of the Sp-regulated genes EZH2, cyclin D1 and cyclin E in MDA-MB-231 breast cancer cells. FIG. 9A-9C.

These results clearly demonstrate that drugs inducing Sp downregulation also target HOTAIR, an Sp-regulated oncogenic ncRNA.

The following is a description of further characterizations of HOTAIR regulation by SpTFs and the implications for drug targeting.

Introduction:

LncRNA expression is polII-dependent. However, the trans-acting factors that regulate these RNAs are essentially unknown. Results described hereinabove demonstrate that knockdown of Sp proteins by RNAi results in decreased HOTAIR expression (see, e.g., FIG. 6B), and ChIP analysis for Sp1 demonstrates that this protein binds the GC-rich region of the HOTAIR promoter. Thus, the high expression and "addiction" of Panc1 cells to Sp1, Sp3, and Sp4 transcription factors results in high levels of HOTAIR, an Sp-regulated gene and this will be further investigated in the panel of pancreatic cancer cells will variable HOTAIR expression. In Panc1 and other cancer cells, overexpression of Sp transcription factors is related to miR-27a-dependent repression of ZBTB10 and miR-20a/miR-17-5p-dependent repression of ZBTB4. Both ZBTB10 and ZBTB4 are transcriptional or "Sp" repressors that bind GC-rich element and inactivate gene expression. Investigations into the regulation of HOTAIR by miR-27a/miR-20a/17-5p-ZBTB10/ZBTB4-Sp protein circuits are described below.

Aim A:

Investigate Sp TFs Regulation of HOTAIR Expression in Pancreatic Cancer Cells.

(i) RNA interference studies. The HOTAIR-overexpressing (Panc1, L3.6pL) cells are transfected with siRNAs for Sp1 (siSp1), Sp3 (siSp3), Sp4 (siSp4) and their combination (siSp1/3/4), as previously described and effects on HOTAIR are determined by real time PCR. A similar approach for pancreatic cancer cells that express lower levels of HOTAIR (e.g., BxPC3, MiaPaCa-2 and Panc28) is also used because this will determine if other factors or lower levels of Sp1, Sp3, and Sp4 are responsible for decreased expression of HOTAIR. Overexpression of Sp proteins in cells expressing low levels of HOTAIR are also determine if limiting levels of Sp1, Sp3, and Sp4 influence HOTAIR expression and function.

(ii) ChIP assay of Sp binding to HOTAIR promoter. The binding of Sp1, Sp3, and Sp4 to the HOTAIR promoter is determined to confirm the occupation of these GC-rich sites by individual Sp transcription factors in pancreatic cancer cells and the loss of these proteins after RNAi (i.e., knockdown of Sp1, Sp3, and Sp4).

Aim B:

Investigate Sp-dependent regulation of HOTAIR by miR-27a:ZBTB10 and miR-20a/17-5p:ZBTB4, miR-27a and miR-20a/miR-17-5p are highly expressed in many cancer cell lines, and studies in several cancer cell lines demonstrated that high levels of Sp1, Sp3, and Sp4 in these cells was due, in part, to miR-27a-dependent inhibition of the transcriptional repressor ZBTB10 and miR-20a/17-Sp inhibition of ZBTB4. ZBTB10 and ZBTB4 bind and partially displace Sp1, Sp3, and Sp4 from GC-rich elements to inhibit gene expression. The inventors have shown that antagomirs of miR-27a, miR-20a and miR-17-5p with ZBTB4 or ZBTB10 overexpression resulted in downregulation of Sp1, Sp3, Sp4, and Sp-regulated genes in breast and pancreatic cancer cells. Therefore, HOTAIR expression in pancreatic cancer cells is likely regulated by miR-27a:ZBTB10-HOTAIR and miR-20a/miR-17-5p:ZBTB4-HOTAIR crosstalk.

(i) Effects of antagomiR-27a and ZBTB10 on HOTAIR expression. Panc1 and L3.6pL are transfected with as-miR-27a or ZBTB10 expression, and HOTAIR expression is determined by real time PCR, and expression of Sp1, Sp3, and Sp4 proteins are determined by western blots. Different amounts of transfected ZBTB10 or as-miR-27a and different treatment times are used to maximize responses using approaches previously described.

(ii) Effects of antagomiR-20a, antagomiR-17-5p and ZBTB4 on HOTAIR expression. The dose-dependent effects of the antagomirs or ZBTB4 overexpression on HOTAIR expression, and Sp1, Sp3, and Sp4 proteins are determined as described above in Aim B(i).

(iii) ChIP assay for ZBTB0 and ZBTB4. ChIP assays are used determine occupation of the GC-rich elements of HOTAIR by Sp1, Sp3, Sp4, ZBTB10, ZBTB4 and polII in pancreatic cancer cells transfected with the antagomirs, ZBTB10 and ZBTB4 expression plasmids. Based on results of the studies described herein, loss of Sp1, Sp3, Sp4 and polII interactions and increased recruitment of ZBTB100 and ZBTB4 to the GC-rich sites are expected.

Expected Results and Alternative Approaches. The investigations described herein will confirm the critical roles of Sp1, Sp3, and Sp4 in regulating HOTAIR in pancreatic cancer cells and also demonstrate that, because regulation of Sp proteins is dependent on miR-27a and miR-20a/17-5p suppression of ZBTB10 and ZBTB4 (29, 30, 38, 50, 51), HOTAIR expression is also regulated by miR-27a:ZBTB10. Mithramycin is a drug that binds GC-rich sites and downregulates Sp1 and other Sp-regulated genes. This compound will also be used in this Example to directly target HOTAIR, and a decrease in HOTAIR expression and displacement of Sp protein from the GC-rich HOTAIR promoter is expected, whereas recruitment of ZBTB4 or ZBTB10 should not be observed.

The following is a description of further characterizations of drug-induced repression of HOTAIR.

Introduction:

The inventors have demonstrated that several different anticancer agents decrease Sp1, Sp3, and Sp4 protein expression in cancer cell lines through multiple mechanisms which are both drug- and cell context-dependent. SpTFs are excellent drug targets due to their overexpression in tumors and relatively low expression in normal tissue which is consistent with the reported decrease in Sp1 levels with increasing age. Data described hereinabove demonstrate that both CDODA-Me and CF3DODA-Me decrease HOTAIR, downregulate Sp proteins and miR-27a, and induce ZBTB10 expression in pancreatic cancer cells (see, e.g., FIGS. 7A-7B and 8A-8D). In this description, investigations are described that will demonstrate that CDODA-Me and CF3DODA-Me decrease HOTAIR through ROS-dependent perturbation of miR-27a:ZBTB10, which results in downregulation of Sp1, Sp3, Sp4, and HOTAIR. In addition, the inventors have recently demonstrated that other ROS-inducing anticancer agents disrupt miR-20a/miR-17-5p-ZBTB4 interactions. Accordingly, the role of this pathway on the effects of CDODA-Me and CF3DODA-Me on HOTAIR expression will also be determined.

Aim A:

CDODA-Me/CF3DODA-Me Downregulate HOTAIR in Pancreatic Cancer Cells.

(i) HOTAIR downregulation. Panc1 and other HOTAIR (high) expressing cell lines are treated with 1.0, 2.5, 5.0, and 7.5 μM CDODA-Me or CF3DODA-Me for 6, 12, 18, 24, and 48 hr. HOTAIR levels are determined by real time-PCR. Using optimal concentrations and times, the effects of these compounds on HOTAIR-induced or -repressed genes are determined to further confirm that these compounds downregulate HOTAIR.

(ii) Role of ROS and ROS-dependent perturbation of the miR-27a:ZBTB10-Sp and miR-20a/17-5p:ZBTB4-Sp pathways. Using the same treatment protocol indicated above, the effects of CDODA-Me/CF3DODA-Me on ROS, miR-27a, ZBTB10, Sp1, Sp3, and Sp4 levels are determined as described, and the effects of antioxidants (catalase, DTT, GSH, NAC) on this pathway and HOTAIR expression are also determined. Using an optimal treatment time and concentration of CDODA-Me and CF3DODA-Me, cells are transfected with miR-27a or miR-20a mimics or siZBTB10/siZBTB4 (knockdown) to reverse the drug-induced downregulation of HOTAIR and confirm the role of ROS-MiR:ZBTB in mediating the repression of HOTAIR. In addition, the effects of the treatments on interaction of Sp proteins and ZBTB10 and ZBTB4 with the GC-rich HOTAIR promoter are determined in a ChIP assay.

Figure 10:
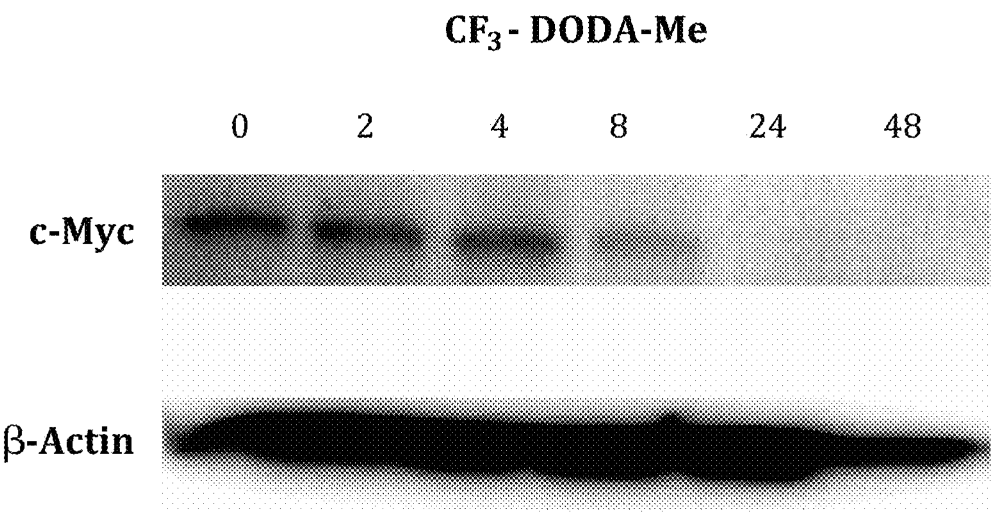
FIG. 10 illustrates the time-dependent suppression of c-Myc expression in Panc1 cells by treatment of 6 μM $CF_3$DODA-Me. Reduction in c-Myc expression was noticeable within 4 hours and c-Myc was undetectable at 24 hours.

(iii) Role of c-Myc in ROS-dependent repression of HOTAIR. The proposed investigations coupled with the established results support the hypothesized linkage between drug-induced ROS and ROS-mediated effects on miR-ZBTB which results in repression of Sp-TFs and HOTAIR. A recent study demonstrated that ROS($H_2O_2$) induces chromatin shifts and relocalizes methyl transferases/PRC4 from non-GC-rich to GC-rich areas. One of the repressed genes is Myc, which also regulates miR-27a and miR-20a/17-5p (miR-17-92 cluster). FIG. 10 is a western blot demonstrating that CF3DODA-Me downregulates Myc protein expression in Panc1 cells. Comparable responses for other ROS inducers have also been observed (data not shown). Therefore, in this investigation, Myc expression is knocked down by RNAi (siMyc) and the effects on miR:ZBTB-Sp axis and HOTAIR expression are determined. A ChIP assay on the HOTAIR promoter is used to confirm this pathway. It is possible that ROS-induced relocalization of repressor complexes such as PRC4 will directly affect HOTAIR transcription. In this scenario, a ChIP assay is used to determine changes in binding of PolII, methylated histones and PRC4 complex members on the GC-rich HOTAIR promoter.

Aim B:

CDODA-Me/CF3DODA-Me decrease HOTAIR and tumor growth in vivo. Knockdown of HOTAIR in L3.6pL cells by RNAi dramatically decreased tumor growth in a nude mouse xenograft model. In this Aim, stably transfected L3.6pL cells are used in an orthotopic model of pancreatic cancer which also undergoes liver metastasis. Mithramycin blocks Sp-mediated transactivation and, thus, is used as a third "control" drug that targets Sp proteins and should also decrease HOTAIR expression.

(i) Role of HOTAIR in pancreatic tumor growth and metastasis. L3.6pL cells are stably transfected with a lentiviral-shRNA to knockdown HOTAIR and the effects of wild-type L3.6pL cells (transfected with a non-specific lentiviral shRNA) vs. HOTAIR knockdown cells are investigated in an orthotopic pancreatic tumor model (see below). Pancreatic cancer cells that express low levels of HOTAIR (e.g., BxPC3 or MiaPaCa2) are transfected with a lentiviral expression vector for HOTAIR (or a control) and the effects of variable HOTAIR expression are determined in a xenograft model (these cells do not form tumors in the orthotopic model).

(ii) Animal treatment. Male athymic nude mice can be obtained from commercial sources and their use must be approved by an Institutional Animal Care and Use Committee. The mice are housed under specific conditions and in facilities approved by the American Association for Accreditation of Laboratory Animal Care. Ten animals are used for each treatment group. Panc1 and Panc28 cells are used in the xenograft study. Cells are harvested by exposure to trypsin and resuspended in serum-free Hanks' balanced salt solution (HBSS). Viability is assessed by trypan blue exclusion, and only single-cell suspensions exhibiting greater than 95% viability will be used. For subcutaneous tumors, tumor cells ($1\times10^6$ cells) suspended in a volume of 200 μL are implanted subcutaneously in the flank of nude male animals using a 27-gauge needle. Tumors are allowed to grow unperturbed for 10-14 d and when palpable tumors (200 $mm^3$) first appear, mice are randomly assigned to treatment or control groups. Mice are treated (10 per treatment group) with placebo or CF3DODA-Me, CDODA-Me (2, 10, or 20 mg/kg/d), or Mithramycin (0.1 and 0.2 mg/kg/d) (in corn oil) administered every second day for 4 to 6 weeks (depending on appearance and size of control tumors). L3.6pL cells are used for orthotopic pancreatic tumor studies. Cells are injected directly into the pancreas and tumors are analyzed as previously described. Body, organ and tumor weights are determined and tissues are used for histopathology. Metastasis to the liver and other organs is measured according to known methods.

(iii) Analysis of tumor tissues. Tumor sections from animals will be prepared for in situ hybridization and immunohistochemical analysis of proteins and in situ hybridization for Sp and Sp-regulated gene products and mRNAs. Western blot analysis of Sp and Sp-regulated genes will be determined using tumor lysates. RNA extracted from control and treated tumors will be used to determine HOTAIR, ZBTB10, ZBTB4, miR-27a, miR-20a, miR-17-5p, and HOTAIR-regulated genes identified in Aim 1.

Expected Results and Alternative Approaches. Aims A and B will provide complementary in vitro and in vivo results and demonstrate that CDODA-Me/CF3DODA-Me decrease HOTAIR through perturbation of miR-27a:ZBTB10 and miR020a/17-5p:ZBTB4, which results in Sp downregulation (see, e.g., FIGS. 7A and 8C). In addition, HOTAIR stably transfected (or knockdown) cells in orthotopic or xenograft models can be used. Mithramycin is useful as an alternative model for a drug that inhibits Sp-dependent transactivation. Tolfenamic acid also decreases Sp proteins in Panc1 cells through activation of proteasomes, which presents an additional pathway for investigation as to the role in regulating HOTAIR. Finally, transgenic animal models for pancreatic cancer that express endogenous mutant Kras and p53 alleles can be developed in the laboratory for in vivo studies on HOTAIR and lncRNA regulation.

The following is a description of the regulation of MALAT-1 (lncRNA) by SpTFs.

Introduction:

It is demonstrated hereinabove that HOTAIR, a lncRNA, is regulated by SpTFs, and that compositions that suppress SpTF expression also suppress HOTAIR expression. Therefore, the inventors investigated the regulation of other lncRNAs by SpTFs.

Metastasis-Associated-in-Lung-Adenocarcinoma-Transcript-1 (MALAT-1) (Yang et al. *Cell* 147(4):773-88 (November 2011)) is an lncRNA that is overexpressed in multiple cancer cell lines and tumors (Huarte, M., and Rinn, J. L., "Large Non-Coding RNAs: Missing Links in Cancer?" *Hum. Mol. Genet.* 19:R152-161 (2010); Perez, D. S., et al., "Long, Abundantly Expressed Non-Coding Transcripts Are Altered in Cancer," *Hum. Mol. Genet.* 17:642-655 (2008); Li, L., et al., "Role of Human Noncoding RNAs In the Control of Tumorigenesis," *Proc. Nat'l Acad. Sci. USA* 106:12956-12961 (2009)), and MALAT-1 expression is a prognostic factor for decreased survival of stage 1 non-small cell lung cancer (NSCLC) (Ji, P., et al., "MALAT-1, a Novel Noncoding RNA, and Thymosin Beta4 Predict Metastasis and Survival in Early-Stage Non-Small Cell Lung Cancer," *Oncogene* 22:8031-8041 (2003)). MALAT-1 expression is also associated with metastasis in NSCLC patients and MALAT-1 expression is correlated with poor prognosis (survival/recurrent/metastasis) in squamous cell carcinoma of the lung, hepatocellular carcinoma, bladder and colorectal cancer. Moreover, functional studies determined by MALAT-1 knockdown or overexpression indicate that MALAT-1 enhances cell and tumor growth, migration, invasion and epithelial-to-mesenchymal transition. MALAT-1 mechanisms of action include (a) acting as a decoy to bind the tumor suppressor PSF; (b) localizing in nuclear speckles to regulate RNA posttranscriptional modifications; (c) regulating genes involved in synapse function; and (d) regulating growth promoting genes through interaction with polycomb protein 2 (Pc2/CBX4) to promote E2F1 sumoylation and enhance expression of growth promoting genes. Thus, MALAT-1 exhibits a broad range of activities in different cell lines. MALAT-1 expression is enhanced in human tumors vs. non-tumor tissues in several cancers including pancreatic cancer; moreover, human MALAT-1 is highly conserved in mice (hepcarin/hcn) and other mammals (unlike HOTAIR) and its function can be investigated in mouse models.

The results described herein confirm that MALAT-1 exhibits its pro-oncogenic activity in pancreatic cancer cells through regulation of multiple genes and pathways. Moreover, like HOTAIR, the present RNAi studies also show that MALAT-1 expression is regulated by specificity protein (Sp) transcription factors in pancreatic cancer cells. Therefore, it is hypothesized that MALAT-1 is pro-oncogenic in pancreatic cancer cells and in animal models and that MALAT-1 expression is regulated by specificity protein (Sp) transcription factors and can be targeted by anticancer agents that downregulate Sp proteins.

Results:

MALAT-1 Expression in Pancreatic Cancer Cells.

Figure 11:
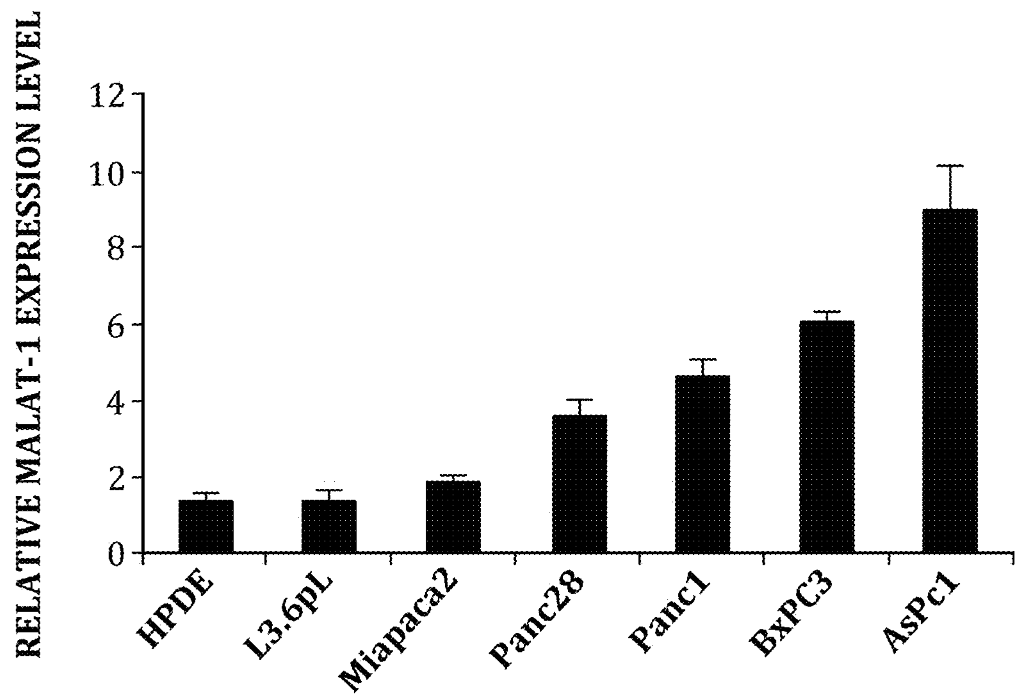
FIG. 11 illustrates the expression of lncRNA MALAT-1 in various pancreatic cancer cell lines as determined by realtime PCR.
Figure 12A:
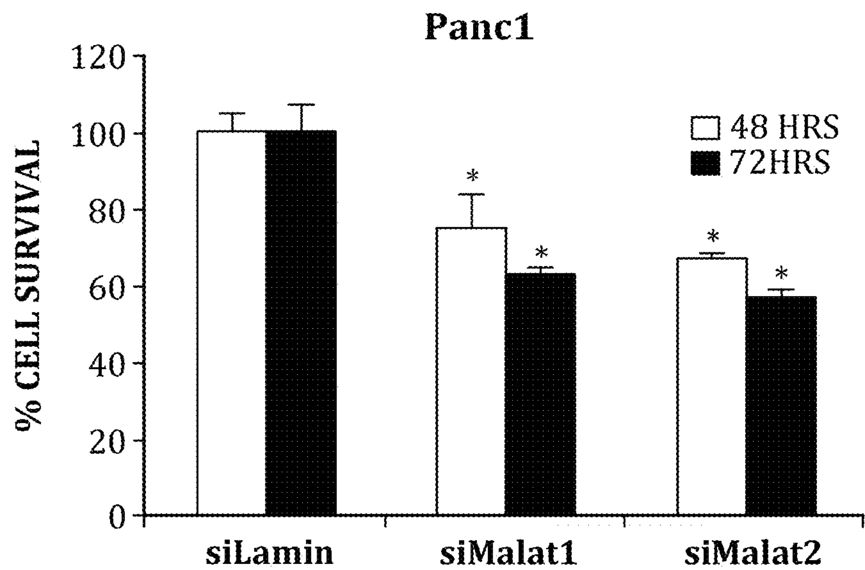
FIGS. 12A and 12B illustrate the effect of MALAT-1 knockdown using two siRNAs (I and II) on Panc1 (FIG. 12A) and Panc28 (FIG. 12B) cells after 48 and 72 hours. * significant inhibition, $p<0.005$.
Figure 12B:
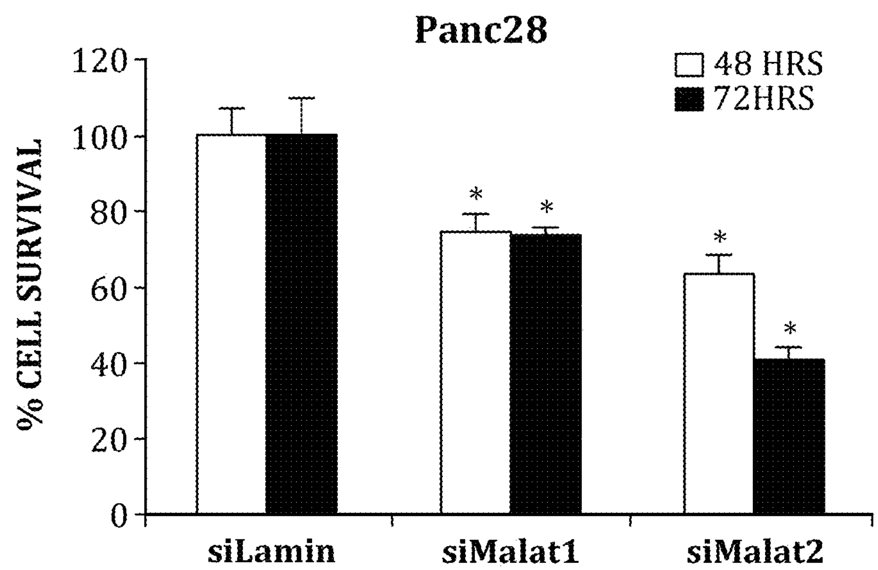

Expression studies in various pancreatic cell lines demonstrated that MALAT-1 is expressed in pancreatic cancer cells FIG. 11. MALAT-1 RNA was detected using forward and reverse oligonucleotides with sequences set forth herein as SEQ ID NOS:7 and 8. Furthermore, MALAT-1 can be detected in serum obtained from pancreatic cancer patients (not shown) and this correlates with the reported high expression of MALAT-1 in pancreatic tumors compared to non-tumor tissues. Subsequent MALAT-1 knockdown studies with RNA interference were conducted using two oligonucleotides (siMALAT-1a and siMALAT-1b), the sequences of which are set forth herein as SEQ ID NOS:5 and 6, respectively. FIGS. 12A and 12B demonstrate that loss of MALAT-1 in Panc1 and Panc28 cells, respectively, resulted in significant inhibition of cell proliferation compared to cells transfected with a control oligonucleotide (siLamin). Thus, MALAT-1 and MALAT-1-regulated genes play a role in pancreatic cancer cell growth. MALAT-1 knockdown by RNAi also significantly decreased transwell migration in Panc28 and Panc1 cells as determined by a Boyden chamber assay (not shown). Additional studies on the role of MALAT-1 in cell survival and kinase signaling were performed, because both pathways are affected, in part, by overexpression of growth factors and activating RAS mutations. These aspects are common in many pancreatic cancer cell lines and tumors. Results in FIGS. 13A and 13B demonstrate that MALAT-1 knockdown induced PARP cleavage (a marker for apoptosis) and inhibited AKT/MAPK (phosphorylated and total proteins, respectively) in Panc28 cells. Similar results were observed in Panc1 cells (not shown).

Because MALAT-1 and MALAT-1-regulated genes are shown to play critical roles in growth, survival and migration of pancreatic cancer cells, further confirmation and characterization will be performed in a panel of pancreatic cancer cell lines, which exhibit variable expression of MALAT-1, as indicated in FIG. 11. This effort will identify both high and low expressors. HPDE cells (non-transformed) will serve as control pancreatic tissue which has relatively low expression of MALAT-1. Additionally, a pancreatic cancer tissue array from the National Disease Research Interchange will be used to investigate expression of MALAT-1 in patient tissues. These fixed tissues will be used to examine MALAT-1 expression by RNA in situ hybridization. Since HOTAIR is also highly expressed in pancreatic cancer cells and tissues, the HOTAIR antisense reverse and antisense forward primers that have previously been described for in situ hybridization of fixed tumor tissue (Chisholm, K. M., et al., "Detection of Long Non-Coding RNA in Archival Tissue: Correlation With Polycomb Protein Expression in Primary and Metastatic Breast Carcinoma," *PLoS One* 7:e47998, 2012, incorporated herein by reference in its entirety). Probes for MALAT-1 (400-500 nt) will be developed based upon unique non-conserved sequences essentially as described (Chintharlapalli, S., et al., "Inhibition of Pituitary Tumor-Transforming Gene-1 in Thyroid Cancer Cells by Drugs That Decrease Specificity Proteins," *Mol. Carcinog.* 50:655-667, 2011, PMCID: PMC3128656, incorporated herein in its entirety). Staining intensities will be scored using a grading system as reported for Rhabdomyosarcoma immunostaining (Chadalapaka, G C., et al., "Inhibition of Rhabdomyosarcoma Cell and Tumor Growth by Targeting Specificity Protein (Sp) Transcription Factors," *Int. J. Cancer* 132:795-806, 2013, PMCII): PMC3527649, incorporated herein in its entirety); comparisons of MALAT-1 with HOTAIR and a control mRNA (GAPDH) will also be performed.

At least two high expressing and low expressing cell lines can be used for knockdown and overexpression of MALAT-1, respectively, to study the function(s) of this lncRNA in pancreatic cancer cells. Exemplary investigation approaches are described here. A non-specific oligonucleotide (RNAi) or empty vector (expression) can be used as controls in all transfection studies.

The antiproliferative effects resulting from MALAT-1 knockdown can be determined in pancreatic cells in proliferation and anchorage-independent growth assays and by FACS analyses. Pancreatic cancer cells are transfected with siMALAT-1 accordingly to standard protocols and the effects on cancer cell growth are determined after 1, 2, 4, and 6 days by cell counting and the MTT assay. The effects of siMALAT-1 on anchorage-independent growth and cell cycle progression are determined and are routinely carried out in the laboratory. The effects of MALAT-1 overexpression on cell proliferation, anchorage-independent growth and cell cycle progression are determined in at least 2 cell lines that express low levels of MALAT-1.

siMALAT-1 or MALAT-1 overexpression can be used on high and low MALAT-1-expressing cells as described above and their effects on apoptosis, activation of caspases 3, 8, and 9 (cleavage), PARP cleavage, TUNEL assay and DNA laddering by enhanced annexin V staining and reversal of these responses by caspase inhibitors (Z-VAD-fmk and LEHD-CHO) (routinely carried out in this laboratory) can be determined. If cells with low expression of MALAT-1 exhibit low endogenous apoptosis, the prosurvival activity of MALAT-1 overexpression can be determined in cells pretreated with an apoptosis-inducing agent such as TPA, and reversal of apoptosis by overexpressing MALAT-1 is determined using the apoptosis assays indicated above. In addition, induction of chemo-resistance by MALAT-1 overexpression is determined against other chemotherapeutic drugs including gemcitabine, doxorubicin and cis-platin.

The effect of MALAT-1 on cell migration and invasion characteristics can be assessed. Pancreatic cancer cells expressing high or low levels of MALAT-1 are transfected with siMALAT-1 or MALAT-1 expression vectors, respectively, and after 78 or 96 hr, cell migration and invasion are determined and quantitated in scratch and Boyden chamber assays essentially, as previously described.

Previous reports suggest that MALAT-1 can play a role in epithelial-to-mesenchymal transition (EMT), which has been linked to cancer progression and metastasis. Cells that exhibit some mesenchymal morphology and this cell line can be transfected with siMALAT-1 and examined for changes in cell morphology and changes in expression of key diagnostic genes associated with the reversal of EMT (e.g., β-catenin, N-cadherin, ZEB-1, ZEB-2, Snail, Slug, and related genes). Cells exhibiting a more "epithelial-like" phenotype can be transfected with MALAT-1 expression plasmid and examined for phenotypic and genotypic changes associated with EMT.

The described investigations are expected to further characterize MALAT-1 as a key pro-oncogenic factor in pancreatic cancer cells and also confirm overexpression in pancreatic tumor vs. non-tumor tissue. In addition to a tumor array, analysis can also proceed on pancreatic tumor samples obtained from a study on metformin, which will add to results of the proposed research.

Regulation of MALAT-1 Expression by SpTFs.

As described above, Sp1, Sp3, and Sp4 TFs are overexpressed in pancreatic and other cancer cell lines, and Sp1 is a negative prognostic factor for pancreatic cancer patient survival. SpTFs regulate expression of genes associated with cell proliferation, survival, metastasis and inflammation, and several growth factor receptor tyrosine kinases. SpTFs are prototypical examples of non-oncogene addiction by cancer cells and are ideally suited as targets for mechanism-based drugs for the following reasons: Sp 1 expression decreases with age in human and rodent tissues; Sp1, Sp3, and Sp4 are highly expressed in cancer cells and tumors compared to non-tumor tissues; and, many drugs that target SpTFs do so through mechanisms/pathways that are highly upregulated in cancer cells compared to non-cancer tissues, which facilitates drug specificity (for cancer cells) and decreased toxicity to normal cells. Silencing of SpTFs and other in pancreatic cancer cells results in growth inhibition, apoptosis and decreased cell migration. These effects are similar to those observed after knockdown of MALAT-1 in these same cell lines (see, e.g., FIGS. 12A, 12B, 13A, and 13B).

Accordingly, MALAT-1 was investigated further for possible regulation by SpTFs in pancreatic cancer cells, and to establish the possibility of manipulation by anticancer drugs that downregulate SpTFs. In an RNAi study, Panc1 cells were exposed to a combination of siSp1/3/4 and to siCT. FIG. 14 demonstrates that silencing of Sp1/3/4 (combined) by RNAi in Panc1 cells significantly decreased MALAT-1 expression, which is consistent with the results described above for HOTAIR.

The regulation of MALAT-1 by SpTFs can be further characterized. Exemplary RNAi and ChIP assays are described. The MALAT-1 overexpressing pancreatic cancer cells are transfected with siRNAs for Sp1 (siSp1), Sp3 (siSp3), Sp4 (siSp4) and their combination (siSp1/3/4), as previously described above, and effects on MALAT-1 expression are determined by real time PCR. A similar approach for pancreatic cancer cells that express lower levels of MALAT-1, as described above, because this will determine if other factors or lower levels of Sp1, Sp3, and Sp4 are responsible for decreased expression of MALAT-1. Overexpression of Sp proteins in cells expressing low levels of MALAT-1 is also determined if limiting levels of Sp1, Sp3, and Sp4 influence MALAT-1 expression and function. ChIP assays are used to characterize the binding of Sp1, Sp3, and Sp4 to the MALAT-1 promoter and to confirm the occupation of GC-rich sites by individual Sp transcription factors in pancreatic cancer cells and the loss of these proteins after RNAi (i.e., knockdown of Sp1, Sp3, and Sp4).

Compounds that downregulate SpTFs also decrease MALAT-1 expression in pancreatic cancer cells.

As described above, the mechanisms of drug-induced downregulation of SpTFs are due to activation of transcriptional and degradation (non-transcriptional) pathways, which are tumor type-, cell context-, and drug-dependent. Among the most effective agents that downregulate SpTFs in pancreatic cancer cells are the synthetic triterpenoid anticancer agents methyl 2-cyano-3,12-dioxooleana-1,9-dien-28-oate (CDDO-Me, bartoxolone) and methyl 2-cyano-3,11-dioxooleana-1,12-dien-30-oate (CDODA-Me). Both compounds, as well as the potent 2-$CF_3$ analog of CDODA-Me ($CF_3$DODA-Me), activate ROS in pancreatic cancer cells, which results in downregulation of miR-27a and induction of the Sp-repressor ZBTB10. Moreover, in some cell lines the inventors have observed induction of a second Sp-repressor (ZBTB4) resulting from the downregulation of miR-20a/miR-17-5p.

Figure 15A:
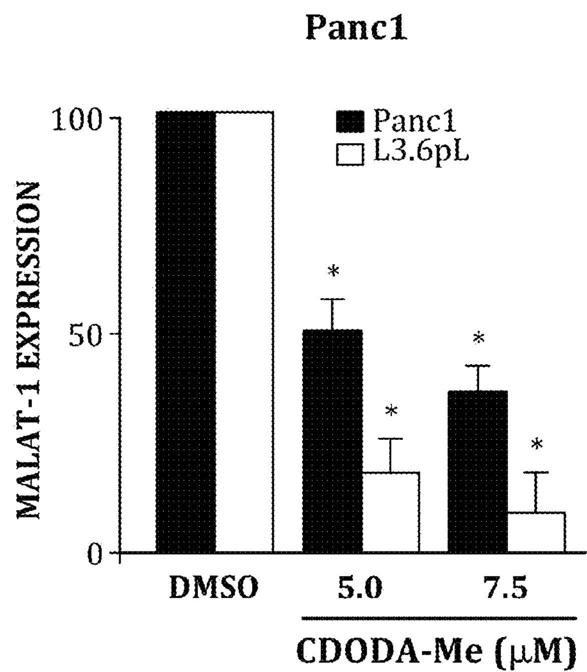
FIG. 15A illustrates the suppression of MALAT-1 expression (RNA abundance) caused by CDODA-Me in Panc1 and L3.6pL cells.
Figure 15B:
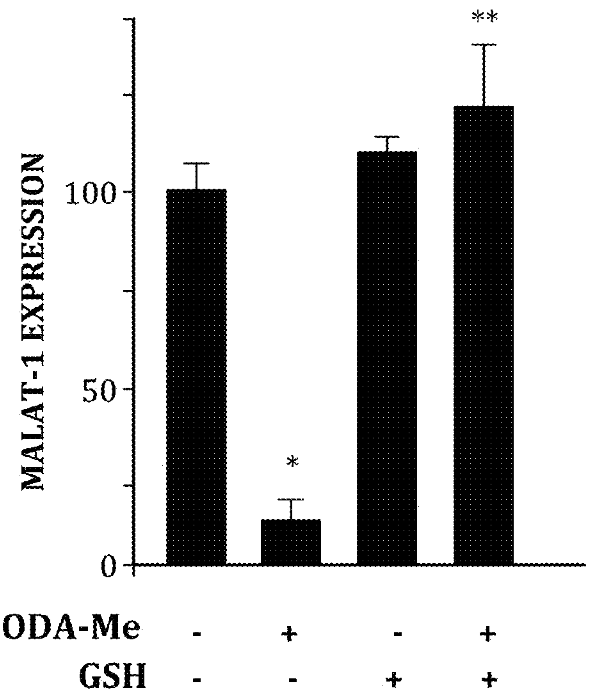
FIG. 15B illustrates the suppression in MALAT-1 expression by $CF_3$DODA-Me, which effect is blocked by GSH. * significant decrease; ** significant reversal.

Accordingly, the inventors investigated the possible regulation of MALAT-1 by drugs known to suppress SpTFs. Results in FIG. 15A show that doses of 5.0 and 7.0 μM CDODA-Me and $CF_3$DODA-Me significantly downregulate MALAT-1 expression in pancreatic Panc1 and L3.6pL cancer cells. Additionally, both compounds were observed to induce ROS (data not shown). Treatment of Panc1 cells with $CF_3$DODA-Me in the presence or absence of glutathione (GSH) shows that the antioxidant inhibits $CF_3$DODA-Me-induced downregulation of MALAT-1 (FIG. 15B), which is consistent with involvement of the ROS pathway. As described above, $CF_3$DODA-Me-mediated downregulation of Sp1, Sp3, and Sp4 is also inhibited by cotreatment with GSH (FIG. 8C), implying involvement of the same pathway.

Further investigations will provide additional insight to the regulatory relationship between SpTFs and MALAT-1. Exemplary studies are described. To study MALAT-1 downregulation, Panc1 and other pancreatic cancer cell lines are treated with 1.0, 2.5, 5.0, and 7.5 μM CDODA-Me or $CF_3$DODA-Me for 6, 12, 18, 24, and 48 hr, and MALAT-1 levels are determined by real time-PCR. Exemplary primer sequences for detection are set forth as SEQ ID NOS:7 and 8. Using optimal concentrations and times, the effects of these compounds on selected HOTAIR-induced or -repressed genes are also determined to further confirm that these compounds downregulate MALAT-1.

Role of ROS and ROS-dependent perturbation of the miR-27a:ZBTB10-Sp and miR-20a/17-5p:ZBTB4-Sp pathways can also be further characterized. Using the same treatment protocol indicated above, the effects of CDODA-Me/$CF_3$DODA-Me on ROS, miR-27a, ZBTB10, Sp1, Sp3, and Sp4 levels are determined, and the effects of antioxidants (catalase, DTT, GSH, NAC) on this pathway and MALAT-1 expression are determined. Using an optimal treatment time and concentration of CDODA-Me and $CF_3$DODA-Me, cells are transfected with miR-27a or miR-20a mimics or siZBTB10/siZBTB4 (knockdown) to reverse the drug-induced downregulation of MALAT-1 and to confirm the role of ROS-miR:ZBTB in mediating the repression of MALAT-1. In addition, the effects of the treatments on binding of Sp proteins and ZBTB10 and ZBTB4 with the GC-rich MALAT-1 promoter are determined in a ChIP assay according to established protocols.

The role of c-Myc in ROS-dependent repression of MALAT-1 can be further characterized as described. The proposed studies coupled with the results established by the inventors support the hypothesized linkage between drug-induced ROS and ROS-mediated effects on miR-ZBTB, which results in repression Sp-TFs and MALAT-1. A recent study (Lee, S. O., et al., "The Nuclear Receptor TR3Regulates mTORC1 Signaling in Lung Cancer Cells Expressing Wild-Type p53," *Oncogene* 31:3265-3276, 2012) demonstrated that ROS($H_2O_2$) induces chromatin shifts and relocalizes methyl transferases/PRC2 from non-GC-rich to GC-rich areas and one of the repressed genes is Myc, which also regulates miR-27a and miR-20a/17-5p (miR-17-92 cluster). It is demonstrated hereinabove that CF3DODA-Me downregulates Myc protein expression in Panc1 cells. See FIG. 10. Moreover, the inventors have observed comparable responses for other ROS inducers (not shown). Therefore, in an exemplary study, knockdown of Myc by RNAi (siMyc) can determine the effects on miR:ZBTB-Sp axis and MALAT-1 expression, and a ChIP assay on the MALAT-1 promoter can be used to confirm this pathway. ROS-induced relocalization of repressor complexes such as PRC2 will directly affect MALAT-1 transcription and a ChIP assay can be used to determine changes in binding of Pol II, methylated histones (H3K27me3), and binding of PRC2 complex members on the GC-rich MALAT-1 promote.

As described, the silencing of Sp1, or all three SpTFs, inhibited cell growth and induced apoptosis, which was comparable to effects observed after knockdown of MALAT-1. Based on these studies, the prospective studies described herein are expected to demonstrate that MALAT-1 is a critical Sp-regulated lncRNA in pancreatic cancer. Further, these studies are predicted to show that drugs such as CDODA-Me and $CF_3$DODA-Me trigger a cascade which involves ROS-dependent disruption of miR-ZBTB complexes followed by ZBTB10/ZBTB4-mediated repression of MALAT-1.

In Vivo Investigations of MALAT-1 in Pancreatic Tumor Growth.

Mouse MALAT-1 (hcn) was identified as an overexpressed RNA in carcinogen-induced liver tumors, and the sequence homology between human and mouse MALAT-1 was conserved. Accordingly, the role of MALAT-1 in pancreatic tumorigenesis can be investigated in both xenografts and transgenic murine models. MALAT-1−/− mice have recently been generated using gene targeting and zinc finger nuclease approaches and, with the exception of some altered changes in gene expression in adult mice, these animals do not exhibit any histological or phenotypic abnormalities. In collaborative studies with the Texas Institute for Genomic Medicine (TIGM) at Texas A&M University, the inventors have used gene-trapped ES cells to generate MALAT-1−/− mice. MALAT-1 expression has not been observed in tissues from these mice, and no phenotypic or histological changes have been detected (data not shown). The MALAT-1−/− mice can be crossed with a transgenic mouse model expressing KRASG12D with a p53 mutation in the pancreas and 100% of these develop pancreatic tumors. In addition, treatment of the transgenic mice with $CF_3$DODA-Me will permit observation of the effects on expression of MALAT-1 and other genes/proteins involved in the miR-ZBTB-Sp-MALAT-1 pathway in pancreatic tumors.

The role MALAT-1 in regulating pancreatic tumor growth: exemplary xenograft or orthotopic studies. Pancreatic cancer cells are transfected with a non-specific small hairpin oligonucleotide and an shMALAT-1 to obtain cells in which MALAT-1 is permanently silenced. These cells can be used for xenograft experiments as described above. Control and MALAT-1-silenced cells are harvested by exposure to trypsin and resuspended in serum-free Hanks' balanced salt solution (HBSS). Viability is assessed by trypan blue exclusion, and only single-cell suspensions exhibiting greater than 95% viability will be used. For subcutaneous tumors, tumor cells ($1\times10^6$ cells) suspended in a volume of 200 μl are implanted subcutaneously in the flank of nude male animals using a 27-gauge needle. Tumors are allowed to grow unperturbed for 10-14 d and when palpable tumors (200 mm3) first appear, mice are randomly assigned to treatment or control groups. Mice are treated (10 per treatment group) with placebo or CF3DODA-Me or CDODA-Me (2, 10, or 20 mg/kg/d) (in corn oil) administered every second day for 4 to 6 weeks (depending on appearance and size of control tumors). L3.6pL cells are used for orthotopic pancreatic tumor studies. Cells are injected directly into the pancreas and tumors are analyzed as previously described in this laboratory. Body, organ, and tumor weights are determined and tissues are used for histopathology.

Tumor sections from animals are prepared for in situ hybridization and immunohistochemical analysis of proteins and in situ hybridization for Sp and Sp-regulated gene products and mRNAs. Western blot analysis of Sp and Sp-regulated genes are determined using tumor lysates. RNA extracted from control and treated tumors is used to confirm expression patterns for identified MALAT-1, ZBTB10, miR-27a and MALAT-1-regulated genes.

Exemplary transgenic animal studies are described herein. Ras mutations are common in human pancreatic ductal adenocarcinomas (PDACs) and oncogenic $Ras^{G12D}$ mouse models coupled with other conditional deletions or mutations of p53, smad4 or TGFβRII. The inventors have demonstrated that MALAT-1 silencing in Panc1 cells affected kinase signaling (see FIGS. 13A and 13B). Accordingly, it is hypothesized that loss of MALAT-1 in the $Ras^{G12D}$ mice containing a p53 mutation will result in a less severe or a delayed development of pancreatic cancer.

The role MALAT-1 in pancreatic tumor development can be addressed with the following exemplary studies. MALAT-1-mice can be crossed with the PdxCre-expressing mice with both KrasG12D and Trp53R172H mutations. 100% of these animals develop pancreatic ductal adenocarcinomas. These double mutant KrasG12D/p53mut mice in which MALAT-1 has been knocked out are predicted to exhibit a delay in tumor occurrence and possibly some decreased severity. After generation of the KrasG12D/p53mut-MALAT-1 knockout mice, the development of pancreatic ductal adenocarcinoma (PDAC) is determined essentially as described (Hingorani, S. R., et al., "Trp53R172H and KrasG12D Cooperate to Promote Chromosomal Instability and Widely Metastatic Pancreatic Ductal Adenocarcinoma in Mice," *Cancer Cell* 7:469-483, 2005). Briefly, the development of cachexia, rapid weight loss or labored breathing and abdominal distension should be carefully monitored, and the animals are sacrificed when these symptoms are observed because these are end-points indicating advanced disease. Pancreatic tumor weights, volumes and histology are determined. Metastasis to the liver, lung, adrenals and peritoneum is determined by histologic examination of each animal essentially accordingly to established procedures. Finally, expression of selected genes including ErbB1 (EGFR), ErbB2 and markers of epithelial to mesenchymal transition (e.g., β-catenin, N-cadherin, ZEB-1, ZEB-2, Snail, Slug, and related genes) is determined.

Inhibition of tumor development/growth by CF3DODA-Me can be addressed. Previous studies have demonstrated that the triterpenoid anticancer agent Bartoxolone (CDDO-Me) increases the survival time of $Kras^{G12D}/p53^{mut}$ mice from 20.5±0.9 wk (controls/unheated) to 24.2±27 wk. In exemplary studies, randomized 4 week old transgenic mice (at least 10 per treatment group) are used. Corn oil control or CF3DODA-Me (10 or 25 mg/kg/d) in corn oil are administered by oral gavage every second day. The animals are monitored and analyzed as outlined in above. Expression of MALAT-1, Sp1, Sp3, Sp4, ZBTB10, ZBTB4, and other selected Sp-regulated gene products are determined by real time PCR and western blots.

Expected Results and Alternative Strategies. Results of xenograft and orthotopic models are expected to demonstrate that knockdown of MALAT-1 in these cells result in a significant loss of their oncogenic potential. A similar approach was used in the studies described above with regard to HOTAIR.

The following is a description of the regulation of HOTTIP (lncRNA) by SpTFs.

Introduction:

It is demonstrated hereinabove that HOTAIR, a lncRNA, is regulated by SpTFs, and that compositions that suppress SpTF expression also suppress HOTAIR expression. Therefore, the inventors investigated the regulation of other lncRNAs by SpTFs.

HOXA transcript at the distal tip (HOTTIP) is an lncRNA that influences activation of 5' HOXA genes.

Figure 16:
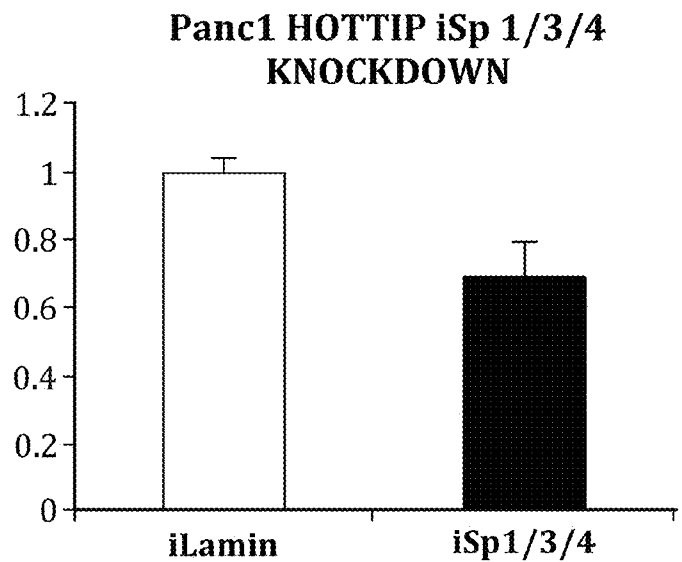
FIG. 16 illustrates the suppression of HOTTIP expression (RNA abundance) in Panc1 caused by RNAi knockdown of Sp1/3/4 TFs with a combined siSp1/3/4.
Figure 17:
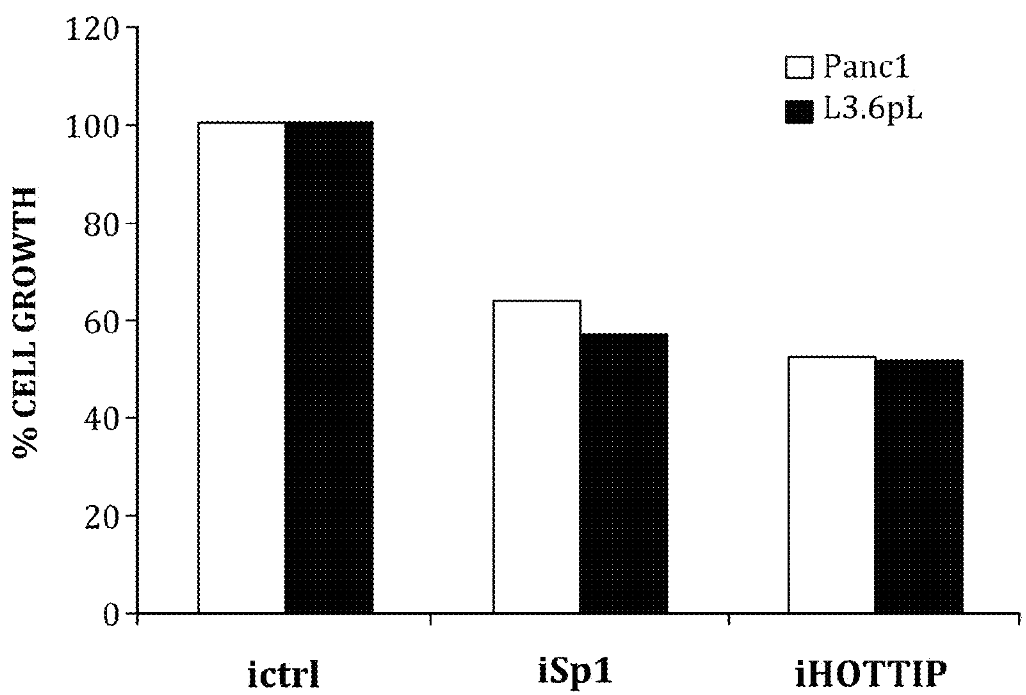
FIG. 17 illustrates the reduction in Panc1 and L3.6pL cell growth caused by RNAi knockdown of Sp1 and HOTTIP, as determined in a cell proliferation assay.
Figure 18A:
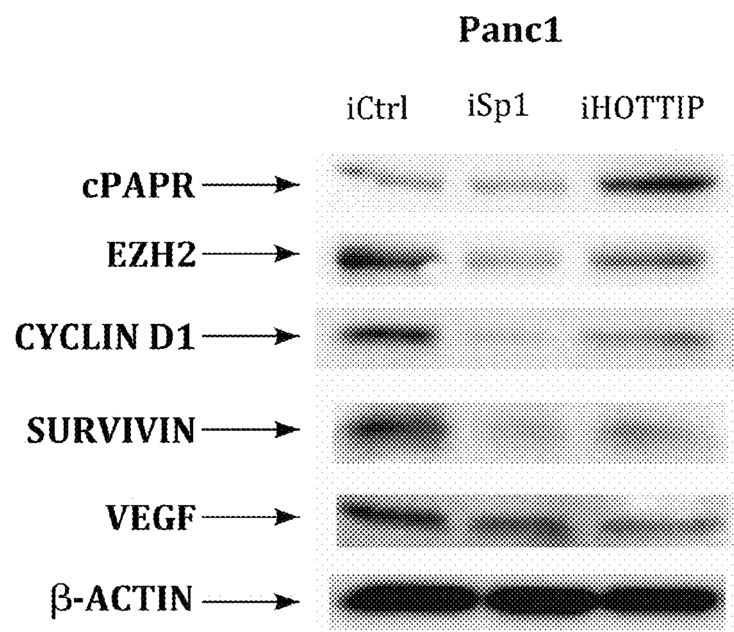
FIGS. 18A and 18B illustrate the regulatory effect of Sp1 and HOTTIP on various genes (cPARP, EZH2, Cyclin D1, surviving, and VEGF) in Panc1 (FIG. 18A) and L3.6pL (FIG. 18B) cells, as determined by RNAi knockout using iSp1 and iHOTTIP.
Figure 18B:
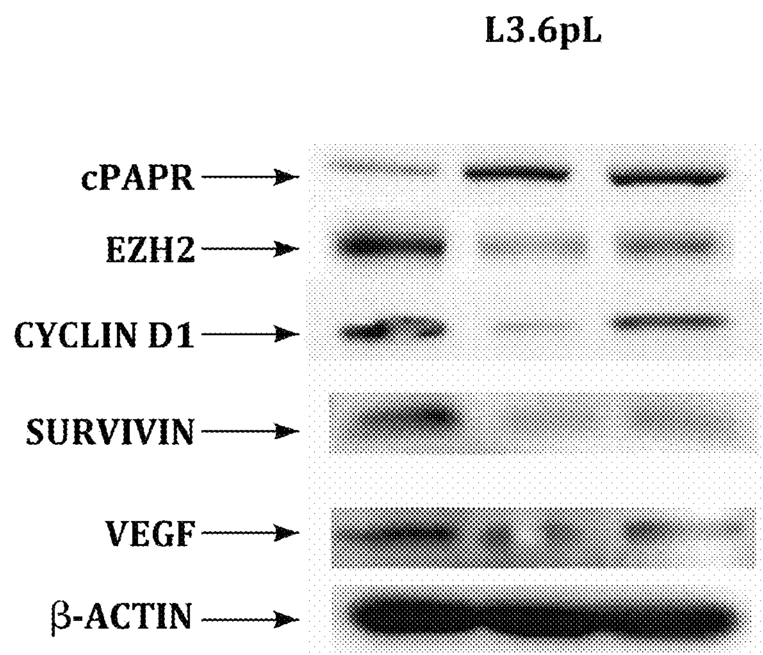
Figure 19A:
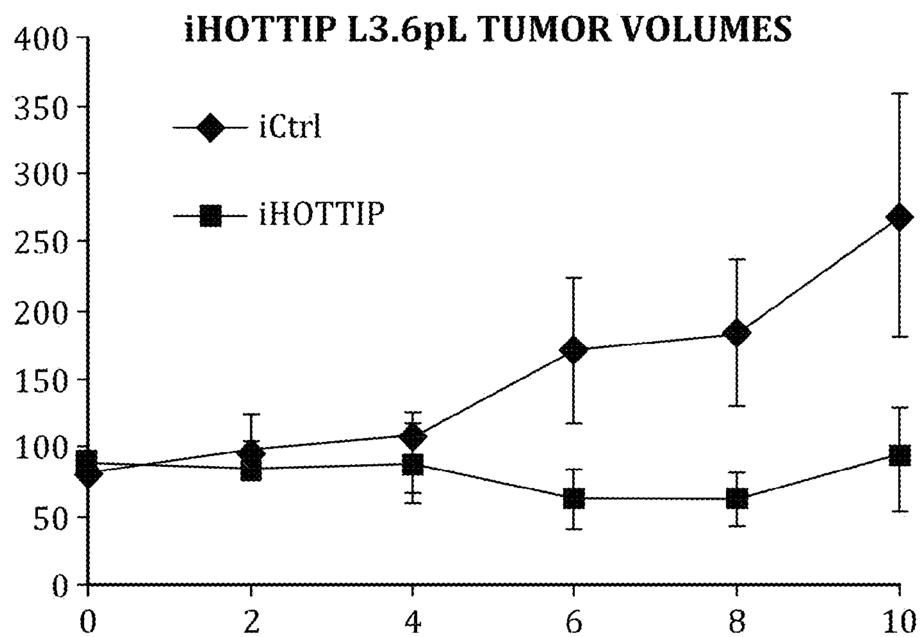
FIGS. 19A and 19B illustrate the inhibition of tumor development in a murine xenograft model using L3.6pL cells cause by knockdown of HOTTIP.
Figure 19B:
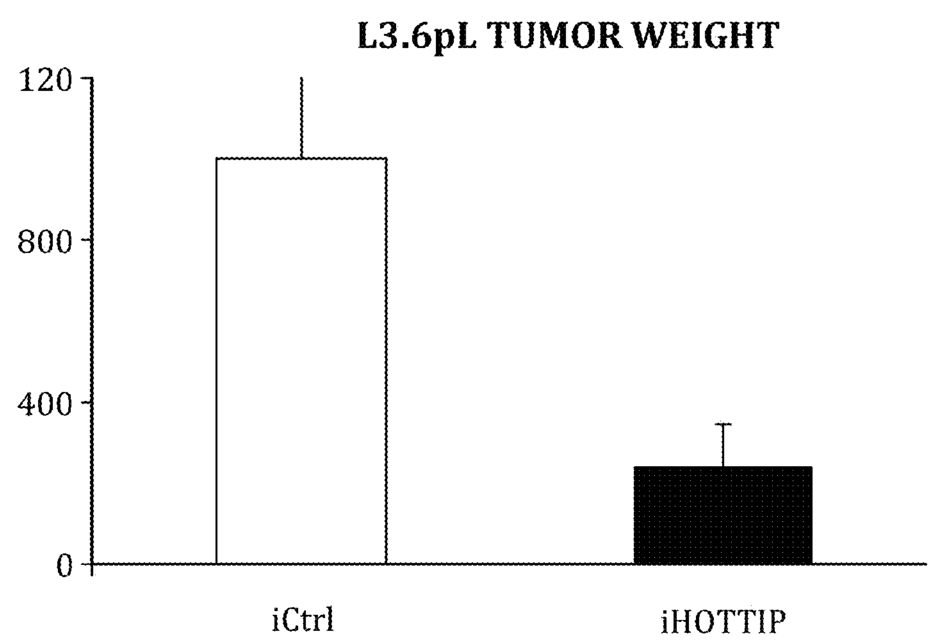

Results and Discussion:

The inventors investigated whether expression of HOTTIP is regulated by SpTFs, as is demonstrated above for HOTAIR. Using a combination of siRNAs for Sp1, Sp3, and Sp4 (iSp1/3/4), abundance of measurable HOTTIP mRNA was reduced in Panc1 cancer cells. See FIG. 16. Further, cell proliferation was assayed for Panc1 and L3.6pL pancreatic cancer cells exposed to siRNA oligonucleotides for control siRNA (iCtrl), Sp1 (siSp1, SEQ ID NO:19), and HOTTIP (siHOTTIP, the sequence of which is set forth herein as SEQ ID NO:9). FIG. 17 demonstrates that both pancreatic cancer cell lines exhibited similar reductions in cell growth with a knockdown of Sp1 and HOTTIP. Similarly, apoptosis assays were performed as described above. Briefly, Panc1 and L3.6pL pancreatic cancer cells were transfected with control siRNAs, siSp1 and siHOTTIP. After an incubation period, the cells were stained with Annexin V. Both Panc1 and L3.6pL cells exhibited increased staining, which is associated with induction of apoptosis, upon knockdown of HOTTIP and Sp1, with staining especially pronounced in Panc-1 cells (not shown). The effect of HOTTIP and Sp1 knockdown on cell migration was assayed using a Boyden chamber assay as described above, indicating that knockdown of each target significantly decreased transwell migration (not shown). The effect of HOTTIP and Sp1 knockdown on expression of various genes relevant to cancer progression and control was also investigated. FIG. 18A demonstrates the effects of RNAi knockdown of Sp1 and HOTTIP in Panc1 cells. As illustrated, knockdown of HOTTIP induced expression of cPARP, a marker for apoptosis, and decreased expression of Sp1-regulated genes EZH2 and Cyclin D1, as well as survivin (a "cancer suppressor") and VEGF (an angiogenic gene). Knockdown of HOTTIP in L3.6pL cells had similar effects, although knockdown of Cyclin D1 was less drastic. Knockdown of Sp1 followed a similar pattern, except it did not induce an increase in cPARP in Panc1 cells and consequence reduction in known Sp-regulated genes EZH2 and Cyclin D1 was more complete in both cell lines. Finally, murine xenograft models were used as generally described in the above descriptions to assess the in vivo effects of HOTTIP on tumor development. L3.6pL cells were transfected with siHOTTIP (or control) and later injected into nude mice. Tumor volumes were assessed over ten days. FIG. 19A demonstrates that knock down of HOTTIP resulted in a significant reduction in tumor volume (i.e., prevented advancing tumor growth) compared to the control cells, with the major differences apparent starting between 4 and 6 days. Mice were sacrificed and tumor weights were determined. FIG. 19B demonstrates that HOTTIP knockdown resulted in approximately a 75% reduction in tumor weight.

These results indicate that HOTTIP and Sp1 coordinately decrease several tumor-suppressor qualities in cells, and their knockdown results in similar responses, such as inhibition of cancer cell growth, induction of apoptosis, and inhibition of migration. HOTTIP, via its interaction with Sp1, is thus a promising target for control or treatment of cancers such as pancreatic cancer.

The following is a description of the regulation of HULC and other lncRNAs by SpTFs in liver and cervical cancer cells.

Introduction:

It is demonstrated hereinabove that HOTAIR, a lncRNA, is regulated by SpTFs, and that compositions that suppress SpTF expression also suppress HOTAIR expression. Therefore, the inventors investigated the regulation of other lncRNAs by SpTFs in cancer cell types other than pancreatic cancer.

Results and Discussion:

The inventors transfected two lines of liver cancer cells (HEPG2 and SK-Hep1) and cervical cancer cells (HeLa) with siRNAs for the Sp1 transcription factor (siSp1) according to standard protocols described herein, to determine whether this TF plays a pro-oncogenic role as observed in other cancer cell types, including pancreatic cancer cells. RNAi knockdown using siSp1 significantly decreased cell proliferation, as expressed as relative percent cell viability, in both liver cancer cell types as well as HeLa cells at both 3 and 5 days post transfection (not shown). Apoptosis assays were performed on SK-Hep1 cells using the Annexin V staining (described above). Briefly, cells were transfected with siSp1, and were subsequently stained with Annexin V, whose uptake (thus staining) is correlated with apoptosis. Knockdown of Sp1 in SK-Hep1 cells resulted in a marked increase in apoptosis (not shown). Furthermore, transwell migration of Hela and SK-Hep1 cells was assayed in a Boyden chamber assay (not shown), indicating a significant decrease in both cell types upon knockdown of Sp1 (not shown). Similarly, Sp1 knockdown was demonstrated to significantly decrease invasion capacity of SK-Hep1 cells (not shown). Using a scratch wound-healing assay, where adherent cells are scraped away from the culture surface and allowed to reestablish adherence over time, it was demonstrated that SK-Hep1 cells are slower to reestablish, i.e., have lower motility, after knockdown of Sp1. These data derived from liver and/or cervical cancer cells are consistent with prior observations regarding the pro-oncogenic role of Sp1 in other cancer cells, indicating the transcription factor's role in regulating cell growth, resisting apoptosis, and promoting migration, invasion and motility.

Figure 20A:
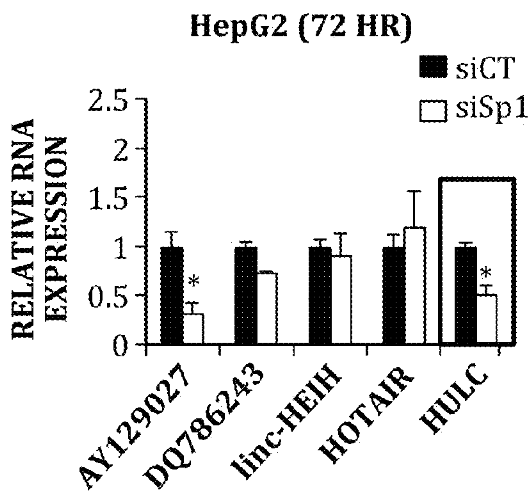
FIGS. 20A-20C illustrate the suppression of lncRNA expression in liver and cervical cancer cells caused by RNAi knockdown of Sp1.
Figure 20B:
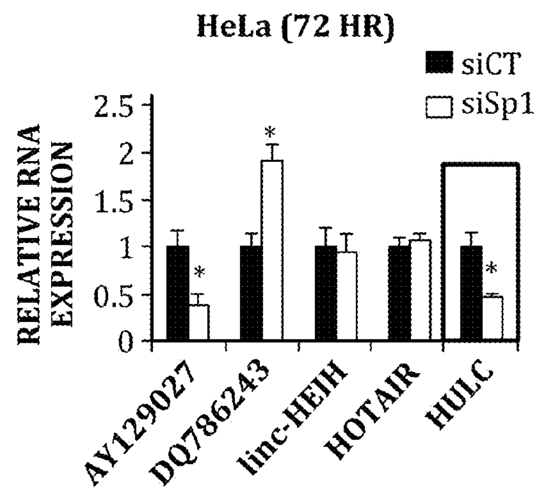
Figure 20C:
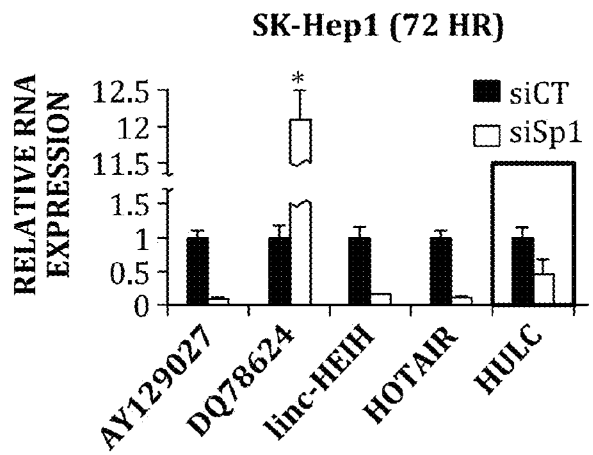

After establishing the pro-oncogenic role of Sp1 in liver and cervical cancer cells, the inventors examined the role of Sp in the expression of various lncRNAs in these cancer cells and the roles of certain lncRNAs in these cancer cells. FIGS. 20A-20C demonstrate that lncRNAs, such as AY129027 (Yang et al., *Hepatology* 54:1679-1689 (2011)), HULC (Panzitt et al., *Gastroenterology* 132: 330-342 (2007)), and linc-HEIH (Yang et al., *Hepatology* 54:1679-1689 (2011)) are decreased when Sp1 is knocked down by RNAi (using siSp1). HULC lncRNA was detected and quantified using forward and reverse oligonucleotide primers whose sequences are set forth herein as SEQ ID NOS:13 and 14, respectively. AY129027 lncRNA was detected and quantified using forward and reverse oligonucleotide primers whose sequences are set forth herein as SEQ ID NOS: 15 and 16, respectively. linc-HEIH lncRNA was detected and quantified using forward and reverse oligonucleotide primers whose sequences are set forth herein as SEQ ID NOS: 17 and 18, respectively. Specifically, FIG. 20A shows that AY129027 and HULC RNA levels significantly declined in HepG2 cells 72 hours after transfection with siSp1. Similarly, FIG. 20B shows that AY129027 and HULC RNA levels significantly declined in HeLa cells 72 hours after transfection with siSp1. Finally, FIG. 20C shows that AY129027, linc-HEIH and HULC RNA levels significantly declined in SK-Hep1 cells 72 hours after transfection with siSp1, in addition to HOTAIR RNA levels.

Figure 21A:
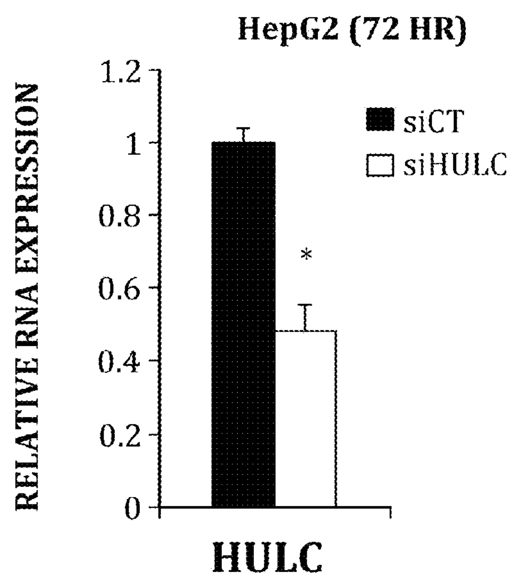
FIGS. 21A-21C illustrate the effective RNAi-based suppression of HULC expression (i.e., reduction of RNA abundance) caused by transfection with siHULC for HepG2 (FIG. 21A), HeLa (FIG. 21B), and SK-(FIG. 21C) cells.
Figure 21B:
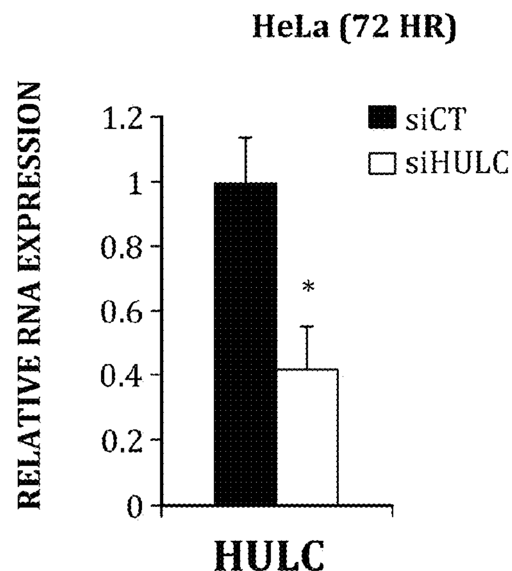
Figure 21C:
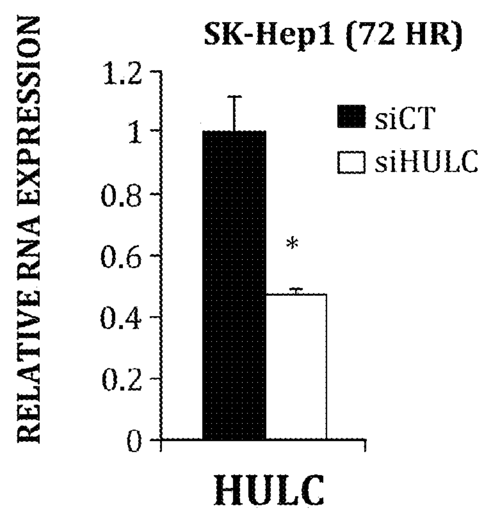
Figure 22A:
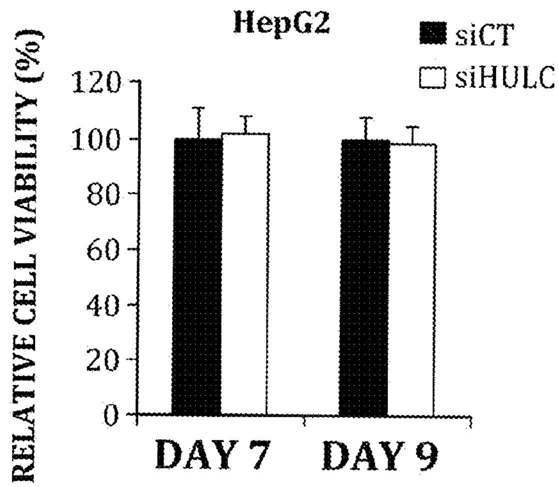
FIGS. 22A-22C illustrate the effect of HULC on cell viability for liver and cervical cancer cells as determined by RNAi knockdown of HULC using siHULC. siHULC was transfected in HepG2 (FIG. 22A), HeLa (FIG. 22B), and SK-Hep1 (FIG. 22C) cells and cell viability was assessed by trypan blue exclusion.
Figure 22B:
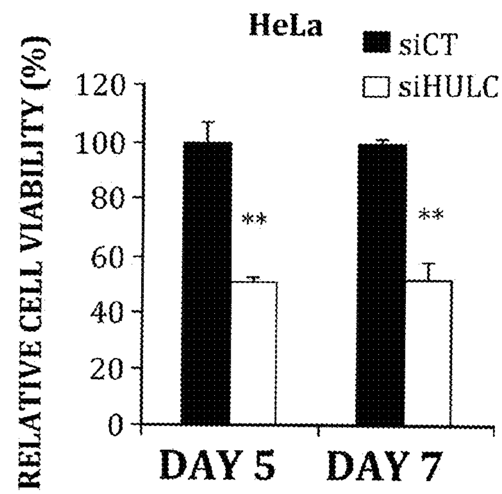
Figure 22C:
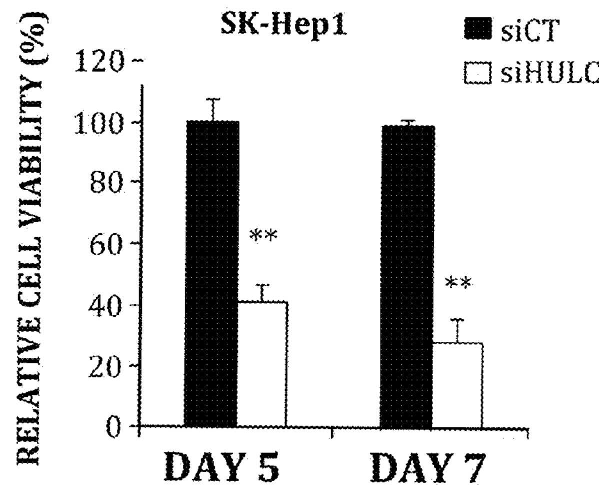
Figure 23A:
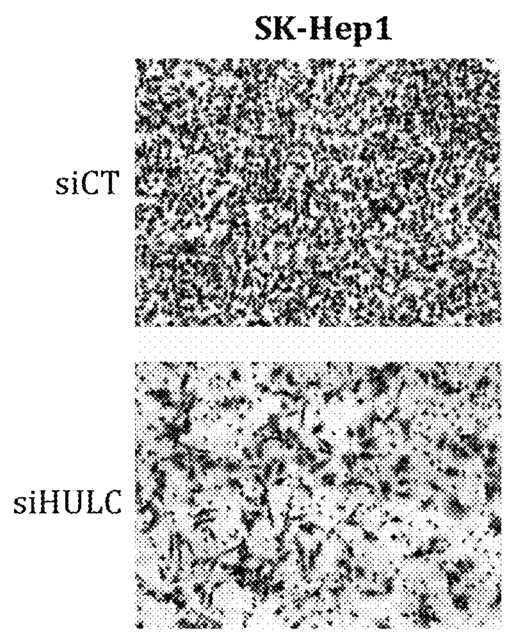
FIGS. 23A and 23B illustrate the effect of HULC knockdown on SK-Hep1 cell invasion/migration, as determined by Boyden chamber cell assays.
Figure 23B:
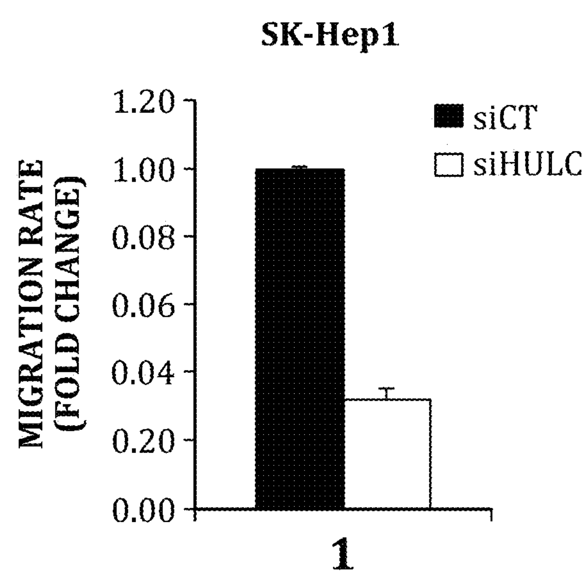

After establishing that Sp1 regulates several lncRNAs in these cancer cells, specific focus was applied on HULC as a model lcnRNA for characterization in liver and cervical cancer cells. As a preliminary matter, FIGS. 21A-21C respectively demonstrate that RNAi using siHULC effectively and significantly decreases HULC lcnRNA levels in HepG2, HeLa, and SK-Hep1 cells by 72 hours post transfection. The sequence of si HULC is set forth herein as SEQ ID NO:12. While HULC knockdown using siHULC did not affect the relative cell viability of HepG2 cells (FIG. 22A), both HeLa and SK-Hep1 cells exhibited significant reductions in cell proliferation at 5 and 7 days post transfection (FIGS. 22A and 22B, respectively). Using the Annexin V staining approach described above, RNAi knockdown of HULC in SK-Hep1 cells using siHULC resulted in a demonstrable increase in apoptosis (not shown). Finally, FIGS. 23A and 23B demonstrate that RNAi knockdown of HULC using siHULC in SK-Hep1 cells, a highly invasive cell line, resulted in a significant decrease in invasion/migration as determined in a Boyden chamber assay.

Figure 24A:
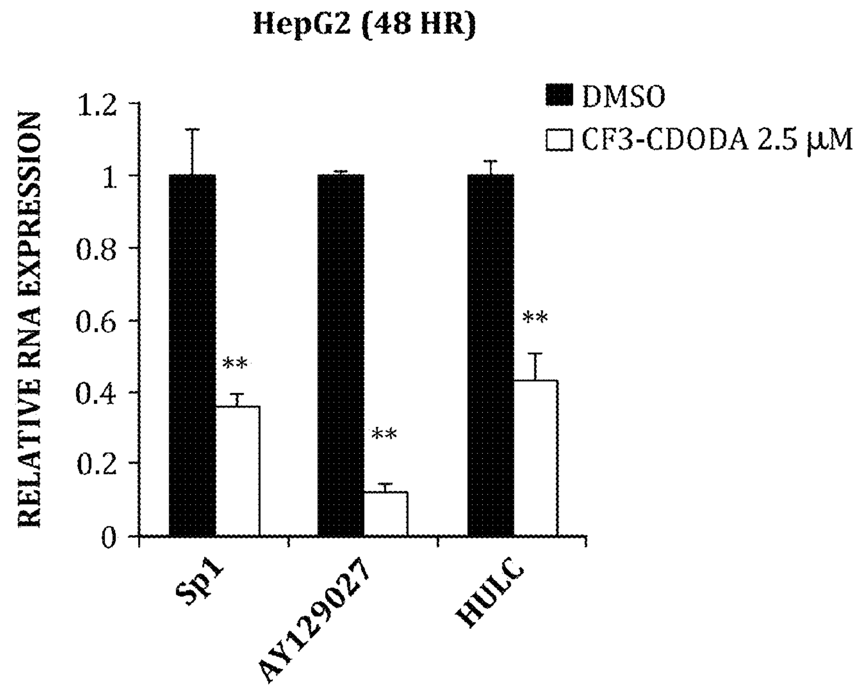
FIGS. 24A and 24B illustrate the suppression of lncRNA expression in liver and cervical cancer cells by drug compounds that suppress Sp1.
Figure 24B:
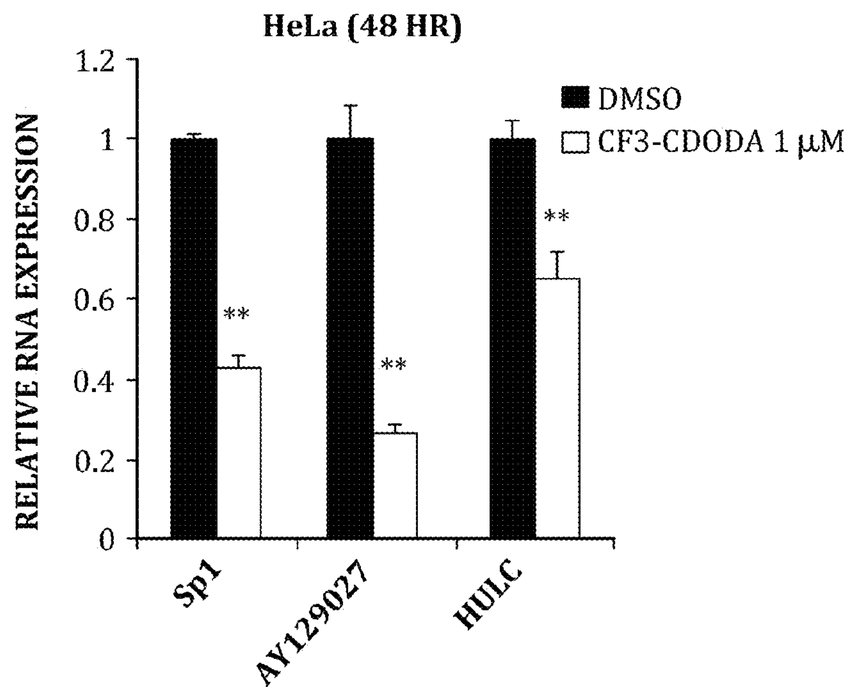
Figure 25A:
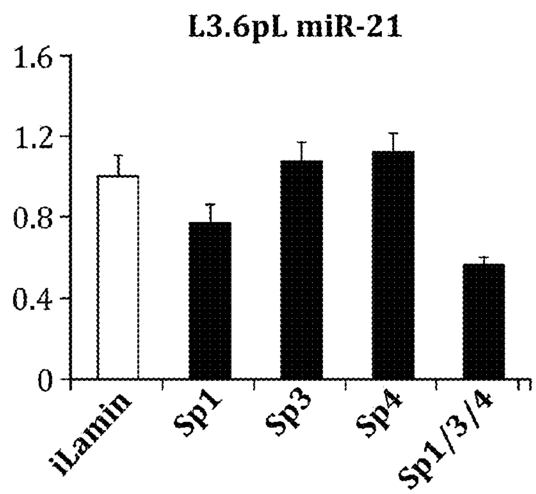
FIGS. 25A-25D illustrate Sp regulation of miRs in L3.6pL and Panc28 cells. L3.6pL (FIGS. 25A and 25B) and Panc28 (FIGS. 25C and 25D) cells were transfected with iSp1, iSp3, iSp4 or iSp1/3/4 and oncogenic miR-21 and miR-181b levels were determined by real time PCR.
Figure 25B:
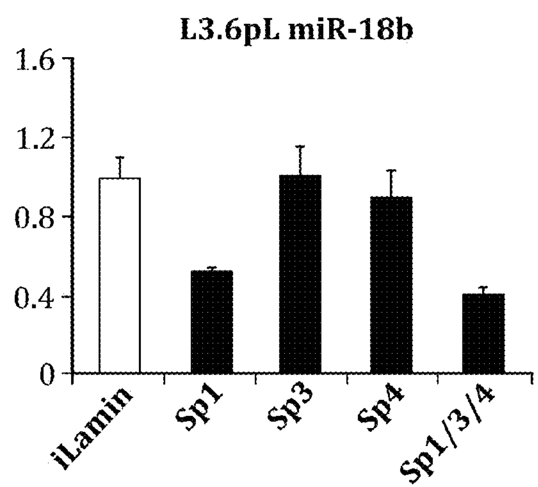
Figure 25C:
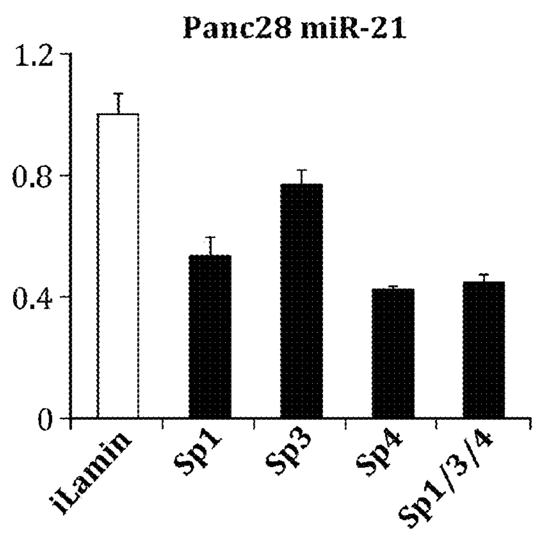
Figure 25D:
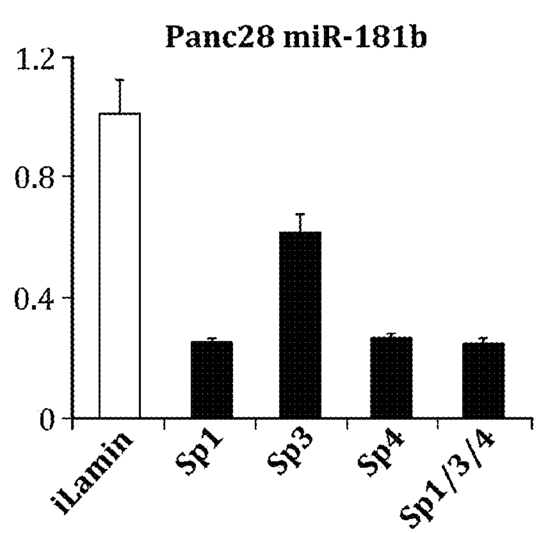

Drugs known to suppress SpTFs were also tested for their ability to cause suppression of HULC lncRNA in liver and cervical cancer cells. FIG. 24A demonstrates that application of $CF_3$DODA, an established Sp-targeting compound (see discussion above), significantly decreased Sp1, AY129027 and HULC expression levels in HepG2 and HeLa cells as determined 48 hrs after exposure.

In conclusion, it is demonstrated that the SpTF Sp1 maintains its pro-oncogenic characteristics in liver and cervical cancer cells. Moreover Sp1 regulates the expression of multiple lncRNAs in these cells, as determined by RNAi knockdown assays. One representative lncRNA, HULC, is demonstrated to promoter tumorigenic characteristics, such as invasion, apoptosis suppression, and invasion, as determined by RNAi knockout. Finally, it is established that drugs suppressing Sp1 activity expression also suppress HULC expression. This demonstrates that Sp1 and additional pro-oncogenic lncRNAs coordinately decrease several tumor-suppressor qualities in cells, and their knockdown results in similar responses, such as inhibition of cancer cell growth, induction of apoptosis, and inhibition of migration, in a variety of cancer cells. Thus, via their interactions with Sp1, pro-oncogenic lncRNAs are promising targets for control or treatment a variety of cancers.

The following is a description of the regulation of oncogenic MiR expression by SpTFs.

Introduction:

It is demonstrated above that numerous oncogenic lncRNAs are regulated by SpTFs, and thus, serve as targets for drugs effective to downregulate SpTFs. MicroRNAs (miR) are another class of ncRNAs. Many miRs are oncogenic and are overexpressed in different tumor types. Oncogenic miR-17, miR-20a, miR-106b, miR-93, and miR-106a are members of the oncogenic miR-17-92, miR-106a-363, and miR-106b-25 clusters. The role of SpTFs in regulating the expression of miR was investigated.

Methods:

siRNAs for Sp1, Sp3, Sp4 and LMN (Lamin) were purchased from Sigma-Aldrich.

Panc28 and L3.6pL pancreatic cancer cell lines were seeded ($6\times10^4$ per well) in 6-well plates in DMEM:Ham's F-12 medium supplemented with 2.5% charcoal-stripped FBS without antibiotic and left to attach for 1 d. Single and triple Sp siRNA knockdown (iSp1, iSp3, iSp4) along with iLamin as control was performed using LipofectAMINE™2000 transfection reagent as per the manufacturer's protocol to attain 100 nM concentration of siRNA in the media. Cells were left with the transfection mixture for 24-48 hrs before changing to fresh 2.5% DMEM-F12 media. Cells were harvested after 60-72 hrs for protein, mRNA or miRNA. miRNA was extracted using mirVana™ miRNA extraction kit (Applied Biosystems) according to manufacturer's protocol and was used to assess expression of various non-coding RNAs using different primers and determined by real-time PCR.

Figure 9D:
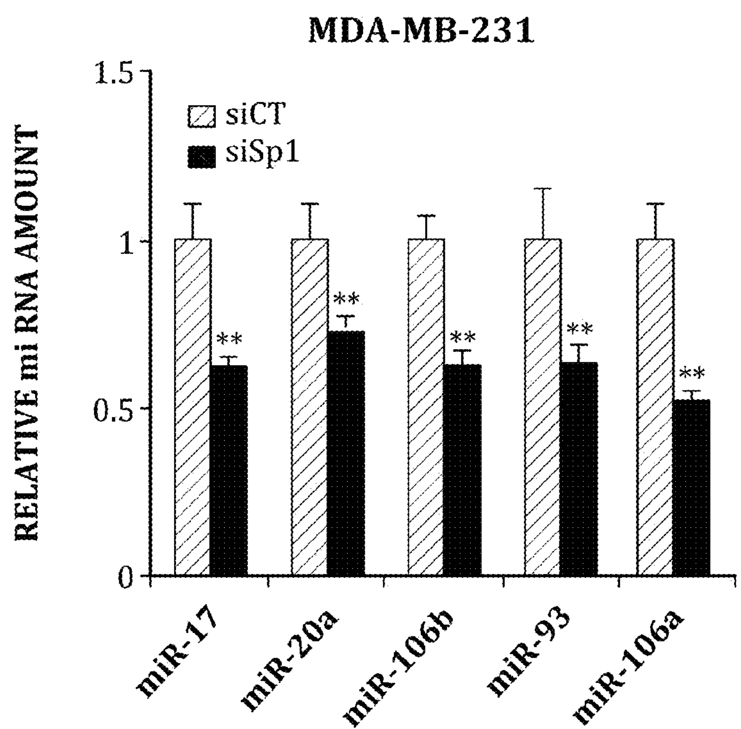

Results and Discussion:

Knockdown of Sp1 also significantly decreased their expression in breast cancer cells (FIG. 9D). MiR-21 and miR-181b have previously been characterized as oncogenic miRs that play an important role in tumor development and growth (*Cancer Res* 70:4528 (2010); *Clin Exp Metastasis* 28:27 (2011); *Oncogene* 29:1787 (2010)). Results illustrated in FIGS. 25A-25D demonstrate that knockdown of Sp1 (iSp1), Sp3 (iSp3), Sp4 (iSp4), and their combination (iSp1/

3/4) decrease expression of oncogenic miR-21 and miR-181b in Panc28 and L3.6pL pancreatic cancer cells.

These results demonstrate that the oncogenic small ncRNAs (i.e., miRs) are also regulated by SpTFs, and therefore, are also targets for drugs that downregulate SpTFs.

While the preferred embodiment of the invention has been illustrated and described, it will be appreciated that various changes can be made therein without departing from the spirit and scope of the invention.

The emodiments of the invention in which an exclusive property or privilege is claimed are defined as follows:

1. A method of inhibiting growth of a cancer cell characterized by overexpression of at least one specificity protein (Sp)-regulated non-coding RNA (ncRNA), compromising reducing the expression or activity of the at least one specificity protein (Sp)-regulated non-coding RNA (ncRNA) by contacting the cell with an effective amount of a specificity protein transcription factor (SpTF) agent that downregulates or represses activity of Sp1, Sp3, or Sp4 wherein the cell is derived from a solid tumor.

2. The method of claim 1, wherein the cancer cell is selected from the group consisting of a breast cancer cell, a pancreatic cancer cell, a liver cancer cell, a lung cancer cell, a prostate cancer cell, a follicular lymphoma cancer cell, and a bladder cancer cell.

3. The method of claim 1, wherein the overexpression of the at least one Sp-regulated ncRNA in the cancer cell can be determined by comparing the expression level in the cancer cell to a reference standard.

4. The method of claim 1, wherein comparing the expression level in the cancer cell to a reference standard comprises comparing the expression level of the at least one Sp-regulated ncRNA to the expression level of the at least one Sp-regulated ncRNA in a noncancerous cell derived from the same tissue.

5. The method of claim 1, wherein the at least one Sp-regulated ncRNA is a long non-coding RNA (lncRNA).

6. The method of claim 5, wherein the IncRNA is selected from the group consisting of HOTAIR, HOTAIRM, HOTTIP, MALAT-1, linc-HEIH, HULC, and AY12907.

7. The method of claim 1, wherein the at least one SpTF is Sp1, Sp3, Sp4 or other Sp/KLF transcription factor.

8. The method of claim 1, wherein the SpTF agent comprises:

(i) a phytochemical or derivative that induces reactive oxygen species (ROS) or phosphatase activity;

(ii) a naturally-occurring or synthetic triterpenoid;

(iii) a non-steroidal anti-inflammatory drug (NSAID);

(iv) an antisense microRNA oligonucleotide;

(v) an agent that causes overexpression of ZBTB10, ZBTB4, or related transcriptional repressor, or that induces proteasome/caspase-dependent degradation of Sp transcription factors;

(vi) a thiazolidinedione;

(vii) a nitro-aspirin;

(viii) an isothiocyanate;

(ix) aspirin;

(x) arsenic trioxide;

(xi) metformin;

(xii) silibinin; or (xiii) a cannabinoid.

9. The method of claim 8, wherein the triterpenoid is methyl 2-cyano-3,12-dioxooleana-1,9-dien-28-oate or methyl 2-cyano-3,11-dioxo-18β-olean-1,12-dien-30-oate.

10. The method of claim 1, further comprising contacting the cell with one or more small interfering RNA (siRNA) molecules that hybridize with the mRNA encoding an SpTF under physiological or cell-culture conditions.

11. The method of claim 1, wherein the cell is in vivo in a subject.

12. The method of claim 1, wherein the cell is in vitro.

13. The method of claim 12, wherein the cell is derived from or comprised in a sample obtained from a subject haying a cell proliferative disease or suspected of having a cell proliferative disease.

14. A method of inhibiting growth of a cancer cell characterized by overexpression of at least one specificity protein (Sp)-regulated non-coding RNA (ncRNA), comprising reducing the expression or activity of the at least one specificity protein (Sp)-regulated non-coding RNA (ncRNA) by contacting the cell with an effective amount of a specificity protein transcription factor (SpTF) agent that downregulates or represses activity of Sp1, Sp3, or Sp4, wherein the cell is a pancreatic cancer cell, a breast cancer cell, a cervical cancer cell, a prostate cancer cell, bladder cancer cell, or a rhabdomyosarcoma cell.

* * * * *

```
SEQUENCE LISTING

<160> NUMBER OF SEQ ID NOS: 39

<210> SEQ ID NO 1
<211> LENGTH: 23
<212> TYPE: DNA
<213> ORGANISM: Artificial sequence
<220> FEATURE:
<223> OTHER INFORMATION: Synthetic

<400> SEQUENCE: 1

ggtagaaaaa gcaaccacga agc                                              23


<210> SEQ ID NO 2
<211> LENGTH: 25
<212> TYPE: DNA
<213> ORGANISM: Artificial sequence
<220> FEATURE:
<223> OTHER INFORMATION: Synthetic

<400> SEQUENCE: 2

acataaacct ctgtctgtga gtgcc                                            25


<210> SEQ ID NO 3
<211> LENGTH: 18
<212> TYPE: DNA
<213> ORGANISM: Artificial sequence
<220> FEATURE:
<223> OTHER INFORMATION: Synthetic

<400> SEQUENCE: 3

cccaccgttc aatgaaag                                                    18


<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4

gtttcaaaca cccacatttc                                                  20


<210> SEQ ID NO 5
<211> LENGTH: 18
<212> TYPE: RNA
<213> ORGANISM: Artificial sequence
<220> FEATURE:
<223> OTHER INFORMATION: Synthetic

<400> SEQUENCE: 5

ggcaauagag gcccuuaa                                                    18


<210> SEQ ID NO 6
<211> LENGTH: 19
<212> TYPE: RNA
<213> ORGANISM: Artificial sequence
<220> FEATURE:
<223> OTHER INFORMATION: Synthetic

<400> SEQUENCE: 6
```

```
gaauuccggu gaugcgagu                                                 19


<210> SEQ ID NO 7
<211> LENGTH: 24
<212> TYPE: DNA
<213> ORGANISM: Artificial sequence
<220> FEATURE:
<223> OTHER INFORMATION: Synthetic

<400> SEQUENCE: 7

agctgtcctt ataggctggc catt                                           24


<210> SEQ ID NO 8
<211> LENGTH: 24
<212> TYPE: DNA
<213> ORGANISM: Artificial sequence
<220> FEATURE:
<223> OTHER INFORMATION: Synthetic

<400> SEQUENCE: 8

tgtttacact gctctgggtc tgct                                           24


<210> SEQ ID NO 9
<211> LENGTH: 21
<212> TYPE: RNA
<213> ORGANISM: Artificial sequence
<220> FEATURE:
<223> OTHER INFORMATION: Synthetic

<400> SEQUENCE: 9

gcacagagau aauggcaaau u                                              21


<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10

cctaaagcca cgcttctttg                                                20


<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11

tgcaggctgg agatcctact                                                20


<210> SEQ ID NO 12
<211> LENGTH: 19
<212> TYPE: RNA
<213> ORGANISM: Artificial sequence
<220> FEATURE:
<223> OTHER INFORMATION: Synthetic

<400> SEQUENCE: 12

ggaagaaacu cugaaguaa                                                 19


<210> SEQ ID NO 13
<211> LENGTH: 21
<212> TYPE: DNA
<213> ORGANISM: Artificial sequence
```

<220> FEATURE:
<223> OTHER INFORMATION: Synthetic

<400> SEQUENCE: 13
atctgcaagc caggaagagt c 21

<210> SEQ ID NO 14
<211> LENGTH: 22
<212> TYPE: DNA
<213> ORGANISM: Artificial sequence
<220> FEATURE:
<223> OTHER INFORMATION: Synthetic

<400> SEQUENCE: 14
cttgcttgat gctttggtct gt 22

<210> SEQ ID NO 15
<211> LENGTH: 20
<212> TYPE: DNA
<213> ORGANISM: Artificial sequence
<220> FEATURE:
<223> OTHER INFORMATION: Synthetic

<400> SEQUENCE: 15
tggaatgaag gcagggctaa 20

<210> SEQ ID NO 16
<211> LENGTH: 22
<212> TYPE: DNA
<213> ORGANISM: Artificial sequence
<220> FEATURE:
<223> OTHER INFORMATION: Synthetic

<400> SEQUENCE: 16
ctcttcttac aaggacgcca gt 22

<210> SEQ ID NO 17
<211> LENGTH: 19
<212> TYPE: DNA
<213> ORGANISM: Artificial sequence
<220> FEATURE:
<223> OTHER INFORMATION: Synthetic

<400> SEQUENCE: 17
cctcttgtgc ccctttctt 19

<210> SEQ ID NO 18
<211> LENGTH: 19
<212> TYPE: DNA
<213> ORGANISM: Artificial sequence
<220> FEATURE:
<223> OTHER INFORMATION: Synthetic

<400> SEQUENCE: 18
atggcttctc gcatcctat 19

<210> SEQ ID NO 19
<211> LENGTH: 19
<212> TYPE: RNA
<213> ORGANISM: Artificial sequence
<220> FEATURE:
<223> OTHER INFORMATION: Synthetic

<400> SEQUENCE: 19
cuacuacuac caccagcaa 19

<210> SEQ ID NO 20
<211> LENGTH: 23
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: Hybrid DNA/RNA

<400> SEQUENCE: 20
gcggcaggug gagccuucac utt 23

<210> SEQ ID NO 21
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: Hybrid DNA/RNA

<400> SEQUENCE: 21
gcagugacac auuagugagc tt 22

<210> SEQ ID NO 22
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: Hybrid DNA/RNA

<400> SEQUENCE: 22
ccacaccaag ucguguucat t 21

<210> SEQ ID NO 23
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: Hybrid DNA/RNA

<400> SEQUENCE: 23
ugaacacgac uuggugtggt t 21

<210> SEQ ID NO 24
<211> LENGTH: 19
<212> TYPE: DNA
<213> ORGANISM: Artificial sequence
<220> FEATURE:
<223> OTHER INFORMATION: Synthetic

<400> SEQUENCE: 24
gggcaagaac tcaggacgg 19

<210> SEQ ID NO 25
<211> LENGTH: 21

<212> TYPE: DNA
<213> ORGANISM: Artificial sequence
<220> FEATURE:
<223> OTHER INFORMATION: Synthetic

<400> SEQUENCE: 25
tctggagtct tcggagtgca a 21

<210> SEQ ID NO 26
<211> LENGTH: 20
<212> TYPE: DNA
<213> ORGANISM: Artificial sequence
<220> FEATURE:
<223> OTHER INFORMATION: Synthetic

<400> SEQUENCE: 26
tatgtggccg atgggaacct 20

<210> SEQ ID NO 27
<211> LENGTH: 20
<212> TYPE: DNA
<213> ORGANISM: Artificial sequence
<220> FEATURE:
<223> OTHER INFORMATION: Synthetic

<400> SEQUENCE: 27
agggtgggtt gacgttctca 20

<210> SEQ ID NO 28
<211> LENGTH: 21
<212> TYPE: DNA
<213> ORGANISM: Artificial sequence
<220> FEATURE:
<223> OTHER INFORMATION: Synthetic

<400> SEQUENCE: 28
tgtccaaggt ggtaaagggt g 21

<210> SEQ ID NO 29
<211> LENGTH: 21
<212> TYPE: DNA
<213> ORGANISM: Artificial sequence
<220> FEATURE:
<223> OTHER INFORMATION: Synthetic

<400> SEQUENCE: 29
ccggcgattt aactgatcct g 21

<210> SEQ ID NO 30
<211> LENGTH: 21
<212> TYPE: DNA
<213> ORGANISM: Artificial sequence
<220> FEATURE:
<223> OTHER INFORMATION: Synthetic

<400> SEQUENCE: 30
gtttccgaag tggacatcgc a 21

<210> SEQ ID NO 31
<211> LENGTH: 23
<212> TYPE: DNA
<213> ORGANISM: Artificial sequence
<220> FEATURE:
<223> OTHER INFORMATION: Synthetic

<400> SEQUENCE: 31
ccattcagta atagagggtg gga 23

<210> SEQ ID NO 32
<211> LENGTH: 20
<212> TYPE: DNA
<213> ORGANISM: Artificial sequence
<220> FEATURE:
<223> OTHER INFORMATION: Synthetic

<400> SEQUENCE: 32
tcgcctactc cgtgaagtct 20

<210> SEQ ID NO 33
<211> LENGTH: 20
<212> TYPE: DNA
<213> ORGANISM: Artificial sequence
<220> FEATURE:
<223> OTHER INFORMATION: Synthetic

<400> SEQUENCE: 33
atgaggatgc ccagaatcag 20

<210> SEQ ID NO 34
<211> LENGTH: 20
<212> TYPE: DNA
<213> ORGANISM: Artificial sequence
<220> FEATURE:
<223> OTHER INFORMATION: Synthetic

<400> SEQUENCE: 34
caccctgcac catatcctct 20

<210> SEQ ID NO 35
<211> LENGTH: 20
<212> TYPE: DNA
<213> ORGANISM: Artificial sequence
<220> FEATURE:
<223> OTHER INFORMATION: Synthetic

<400> SEQUENCE: 35
cactggcaac acaattcagg 20

<210> SEQ ID NO 36
<211> LENGTH: 20
<212> TYPE: DNA
<213> ORGANISM: Artificial sequence
<220> FEATURE:
<223> OTHER INFORMATION: Synthetic

<400> SEQUENCE: 36
ctgctgaagg actgcaagtg 20

<210> SEQ ID NO 37
<211> LENGTH: 20
<212> TYPE: DNA
<213> ORGANISM: Artificial sequence
<220> FEATURE:
<223> OTHER INFORMATION: Synthetic

<400> SEQUENCE: 37
gaggatatgg tgcagggtgt 20

<210> SEQ ID NO 38
<211> LENGTH: 20
<212> TYPE: DNA
<213> ORGANISM: Artificial sequence -continued

```
<220> FEATURE:
<223> OTHER INFORMATION: Synthetic

<400> SEQUENCE: 38

ggagcaccct gcttagactg                                                20


<210> SEQ ID NO 39
<211> LENGTH: 20
<212> TYPE: DNA
<213> ORGANISM: Artificial sequence
<220> FEATURE:
<223> OTHER INFORMATION: Synthetic

<400> SEQUENCE: 39

gggcctcagt atcctcttcc                                                20
```